(12) United States Patent
Bailey et al.

(10) Patent No.: US 12,269,635 B2
(45) Date of Patent: Apr. 8, 2025

(54) PACKAGING SYSTEM FOR PHARMACEUTICAL DISPENSER AND ASSOCIATED METHOD

(71) Applicant: Remedi Technology Holdings, LLC, Towson, MD (US)

(72) Inventors: Jeffrey S. Bailey, Cumming, GA (US); Bobby O. Archer, Lebanon, MO (US); Kimberly Hawkes, Powell, OH (US)

(73) Assignee: Remedi Technology Holdings, LLC, Towson, MD (US)

( * ) Notice: Subject to any disclaimer, the term of this patent is extended or adjusted under 35 U.S.C. 154(b) by 0 days.

(21) Appl. No.: 18/385,215

(22) Filed: Oct. 30, 2023

(65) Prior Publication Data

US 2024/0208681 A1     Jun. 27, 2024

Related U.S. Application Data

(63) Continuation of application No. 18/170,169, filed on Feb. 16, 2023, now Pat. No. 11,834,214, which is a
(Continued)

(51) Int. Cl.
| | |
|---|---|
| *B65G 47/90* | (2006.01) |
| *B25J 15/00* | (2006.01) |
| *B25J 15/02* | (2006.01) |
| *B25J 15/08* | (2006.01) |
| *B65B 5/10* | (2006.01) |

(Continued)

(52) U.S. Cl.
CPC .......... *B65B 5/105* (2013.01); *B25J 15/0014* (2013.01); *B25J 15/0253* (2013.01); *B65B 35/36* (2013.01); *B65B 35/54* (2013.01); *B65G 47/08* (2013.01); *B65G 47/80* (2013.01); *B65G 47/90* (2013.01); *G07F 17/0092* (2013.01);
(Continued)

(58) Field of Classification Search
CPC .......... B65B 5/10; B65B 5/105; B65B 35/36; B65B 35/54; B65G 47/08; B65G 47/28; B65G 47/80; B65G 47/90; B25J 15/08; B25J 15/0014; B25J 15/0253; G07F 17/0092
USPC ......................................................... 53/473
See application file for complete search history.

(56) References Cited

U.S. PATENT DOCUMENTS

| | | |
|---|---|---|
| 655,241 A | 1/1901 | Ludington |
| 797,121 A | 8/1905 | Keller |

(Continued)

FOREIGN PATENT DOCUMENTS

| | | |
|---|---|---|
| CN | 101891023 A | 11/2010 |
| EP | 0608623 A1 | 8/1994 |

(Continued)

OTHER PUBLICATIONS

Office Action issued Apr. 5, 2017 in Australian Patent Application No. 2016202529.
(Continued)

*Primary Examiner* — Douglas A Hess
(74) *Attorney, Agent, or Firm* — Oblon, McClelland, Maier & Neustadt, L.L.P.

(57) ABSTRACT

A package insert module that includes a turntable configured to rotate about a central post and an insert assembly mounted on the turntable and including a finger arrangement configured to offload a plurality of packages arranged in an array on a nest.

7 Claims, 62 Drawing Sheets

Related U.S. Application Data continuation of application No. 16/815,916, filed on Mar. 11, 2020, now Pat. No. 11,603,224, which is a continuation of application No. 15/891,826, filed on Feb. 8, 2018, now Pat. No. 10,618,748, which is a continuation of application No. 13/659,545, filed on Oct. 24, 2012, now abandoned.

(60) Provisional application No. 61/550,787, filed on Oct. 24, 2011.

(51) Int. Cl.
| | | |
|---|---|---|
| *B65B 35/36* | (2006.01) | |
| *B65B 35/54* | (2006.01) | |
| *B65G 47/08* | (2006.01) | |
| *B65G 47/80* | (2006.01) | |
| *G07F 17/00* | (2006.01) | |
| *G16H 20/13* | (2018.01) | |
| *B65G 47/28* | (2006.01) | |
| *B65G 47/51* | (2006.01) | |

(52) U.S. Cl.
CPC ............ *G16H 20/13* (2018.01); *B65G 47/28* (2013.01); *B65G 47/5113* (2013.01); *B65G 2812/02613* (2013.01)

(56) References Cited

U.S. PATENT DOCUMENTS

| | | |
|---|---|---|
| 1,458,701 A | 6/1923 | Haas |
| 2,778,478 A | 1/1957 | Brook |
| 3,283,471 A | 11/1966 | Thurston |
| 3,589,094 A | 6/1971 | Pearson |
| 3,701,297 A | 10/1972 | Kovic |
| 3,760,966 A | 9/1973 | Jones, Jr. |
| 3,809,227 A | 5/1974 | Begemann |
| 4,086,745 A | 5/1978 | Caudle |
| 4,219,300 A | 8/1980 | McMillan |
| 4,247,241 A | 1/1981 | Warren |
| 4,573,863 A | 3/1986 | Picotte |
| 4,700,941 A | 10/1987 | Shill |
| 4,705,470 A | 11/1987 | Penta |
| 4,718,216 A | 1/1988 | Focke |
| 4,887,414 A | 12/1989 | Arena |
| 4,974,392 A | 12/1990 | Mondini |
| 4,984,963 A | 1/1991 | Bon |
| 5,007,785 A | 4/1991 | Van de Schoot |
| 5,081,816 A | 1/1992 | Cardinali |
| 5,156,279 A | 10/1992 | Draghetti |
| 5,191,964 A | 3/1993 | Spisak |
| 5,215,427 A | 6/1993 | Olsthoom |
| 5,273,484 A | 12/1993 | Roger et al. |
| 5,323,587 A | 6/1994 | Amaranti |
| 5,357,734 A | 10/1994 | Focke |
| 5,456,056 A | 10/1995 | Kelly |
| 5,456,058 A | 10/1995 | Ziegler |
| 5,475,965 A | 12/1995 | Mondini |
| 5,484,256 A | 1/1996 | Claassen |
| 5,488,815 A | 2/1996 | Abrams |
| 5,546,734 A | 8/1996 | Moncrief et al. |
| 5,623,816 A | 4/1997 | Edwards |
| 5,666,789 A | 9/1997 | Ziegler |
| 5,775,067 A | 7/1998 | Hawley |
| 5,797,515 A | 8/1998 | Liff et al. |
| 5,802,803 A | 9/1998 | Kitagawa |
| 5,827,039 A | 10/1998 | Gammerier |
| 5,911,557 A | 6/1999 | Gammerier |
| 5,937,620 A | 8/1999 | Chalendar |
| 5,957,517 A | 9/1999 | Chen |
| 6,047,527 A | 4/2000 | Pazdernik |
| 6,058,679 A | 5/2000 | Ziegler |
| 6,082,797 A | 7/2000 | Antonette |
| 6,170,634 B1 | 1/2001 | Jaquet |
| 6,205,748 B1 * | 3/2001 | Daniele ............... B65B 61/28 53/118 |
| 6,516,938 B1 | 2/2003 | Paselsky |
| 6,711,878 B1 | 3/2004 | Paselsky et al. |
| 6,722,101 B2 | 4/2004 | Hartness et al. |
| 6,837,360 B2 | 1/2005 | Schoeneck |
| 6,936,318 B2 | 8/2005 | Dent |
| 6,942,087 B2 | 9/2005 | Meyer |
| 7,018,163 B2 | 3/2006 | Beavers |
| 7,306,423 B2 | 12/2007 | Ogawa |
| 7,392,894 B2 | 7/2008 | Jacob |
| 7,401,828 B2 | 7/2008 | Yang |
| 7,549,265 B2 | 6/2009 | Grabowski |
| 7,726,096 B2 | 6/2010 | Guttinger et al. |
| 7,751,939 B2 | 7/2010 | Cho |
| 7,806,250 B2 | 10/2010 | Ford |
| 7,967,354 B2 | 6/2011 | Faulkner |
| 8,151,802 B2 | 4/2012 | Boldrini |
| 8,668,073 B2 | 3/2014 | Petrovic |
| 8,695,779 B2 * | 4/2014 | Hawkes ............... B25J 15/0014 198/803.14 |
| 8,777,551 B1 | 7/2014 | Widder |
| 8,807,912 B2 | 8/2014 | Liebheit |
| 9,604,741 B2 | 3/2017 | Drechsler |
| 10,160,066 B2 | 12/2018 | Yang |
| 10,414,528 B2 | 9/2019 | Ford |
| 10,442,635 B2 | 10/2019 | Gehin |
| 11,021,288 B2 | 6/2021 | Enderie |
| 11,053,086 B2 | 7/2021 | Ziegler |
| 11,270,371 B2 | 3/2022 | Ramirez |
| 11,511,946 B2 | 11/2022 | Gehin |
| 2002/0170278 A1 | 11/2002 | Hofmann et al. |
| 2003/0099536 A1 | 5/2003 | Monti-Giuseppe |
| 2003/0183466 A1 | 10/2003 | Axel |
| 2003/0192287 A1 | 10/2003 | VanAlstine |
| 2004/0011005 A1 | 1/2004 | Daoust |
| 2004/0040262 A1 | 3/2004 | Palumbo |
| 2004/0040975 A1 | 3/2004 | Hunter et al. |
| 2005/0066628 A1 | 5/2005 | Cerutti |
| 2005/0235613 A1 | 10/2005 | Malini |
| 2006/0000688 A1 | 1/2006 | Monti |
| 2006/0108198 A1 | 5/2006 | Guidetti |
| 2006/0182609 A1 | 8/2006 | Guerra |
| 2006/0288665 A1 | 12/2006 | Imao |
| 2007/0186511 A1 | 8/2007 | Hultberg |
| 2008/0023293 A1 | 1/2008 | Uratani |
| 2008/0066433 A1 | 3/2008 | Takaoka |
| 2008/0131238 A1 | 6/2008 | Lutz |
| 2008/0138187 A1 | 6/2008 | Christ |
| 2009/0013641 A1 | 1/2009 | Prakken |
| 2009/0320417 A1 | 12/2009 | Gilmore |
| 2010/0172724 A1 | 7/2010 | Hawkes |
| 2010/0176145 A1 | 7/2010 | Hawkes et al. |
| 2011/0005171 A1 | 1/2011 | Woerz |
| 2011/0167771 A1 | 7/2011 | Till |
| 2011/0222999 A1 | 9/2011 | Kubota |
| 2012/0013138 A1 | 1/2012 | Ickert |
| 2013/0043103 A1 | 2/2013 | Maier et al. |
| 2014/0037402 A1 | 2/2014 | Ickert |

FOREIGN PATENT DOCUMENTS

| | | |
|---|---|---|
| EP | 0808623 A1 | 8/1994 |
| EP | 1 241 095 A1 | 9/2002 |
| EP | 2 771 243 B1 | 7/2016 |
| EP | 3 100 958 B1 | 4/2018 |
| GB | 1268377 | 4/1972 |
| GB | 1269377 | 4/1972 |
| JP | 62285272 | 12/1987 |
| JP | 3649336 | 5/2005 |
| WO | WO 90/02686 A1 | 3/1990 |
| WO | WO 90/02688 A1 | 3/1990 |

(56) References Cited

FOREIGN PATENT DOCUMENTS

WO     WO 2010/077151 A1     7/2010
WO     WO 2011/033481 A2     3/2011

OTHER PUBLICATIONS

Office Action Issued Mar. 20, 2017 in Australian Patent Application No. 2016202530.
European Search Report Appln. No. 16175478.1 dated Sep. 20, 2016.
Office Action issued Jun. 28, 2016 in Mexican Patent Application No. MX/a/2014/004929 (with English language translation).
Office Action issued Mar. 31, 2016 in Australian Patent Application No. 2012328971.
Combined Office Action and Search Report Issued Jul. 3, 2015 in Chinese Patent Application No. 201280062254.5 (with English Translation of Category of Cited Documents).
Extended European Search Report issued Feb. 25, 2015 in Patent Application No. 12843759.7.
International Search Report and Written Opinion of the International Searching Authority Issued Mar. 4, 2013 in PCT/US2012/061643.
Office Action issued Mar. 14, 2018 in Canadian Patent Application No. 2,853,250.
Office Action issued Mar. 31, 2016 In Australian Patent Application No. 2012326971.
European Search Report Appln No. 16175479.1 dated Sep. 20, 2016.
Chinese Office Action issued on Feb. 12, 2019 in Patent Appln. No. 2018-10236695.2 (with English Translation).
Office Action issued Aug. 10, 2018 in Chinese Patent Appln. No. 206-10236695.2. (7 pages).
Canadian Office Action issued on Jan. 30, 2019 in Canadian Patent Appln No. 3,018,688 (6 pages).
Office Action issued Mar. 20, 2019 in Korean Patent Appln. No. 10-2014-7013525.
Extended European Search Report Issued May 14, 2018 in Patent Appln. No. 18164081.4, citing European Reference 1241095 A1 and WO 2011/033461 A2, cited on sheets 1 and 2 submitted herewith.
Mexican Office Action Issued on Sep. 12, 2018 in Patent Appln. No. MX/a/2017/003252 (with English Translation) citing EP 3100958B1, cited on sheet 1 submitted herewith.
Offics Action issued Mar. 20, 2017 in Australian Patent Application No. 2016202530.
Canadian Office Action issued on Jan. 7, 2021 in Canadian Patent Application No. 3,060,165, 4 pages.
Office Action issued Aug. 2, 2021 in corresponding Canadian Patent Application No. 3,060,165; 4 pages.
Canadian Office Action issued Feb. 7, 2022 in Canadian Patent Application No. 3,060,165, 3 pages.
US 2023/0191543 A1, Feied. et al., Jun. 22 (Year 2023).

\* cited by examiner

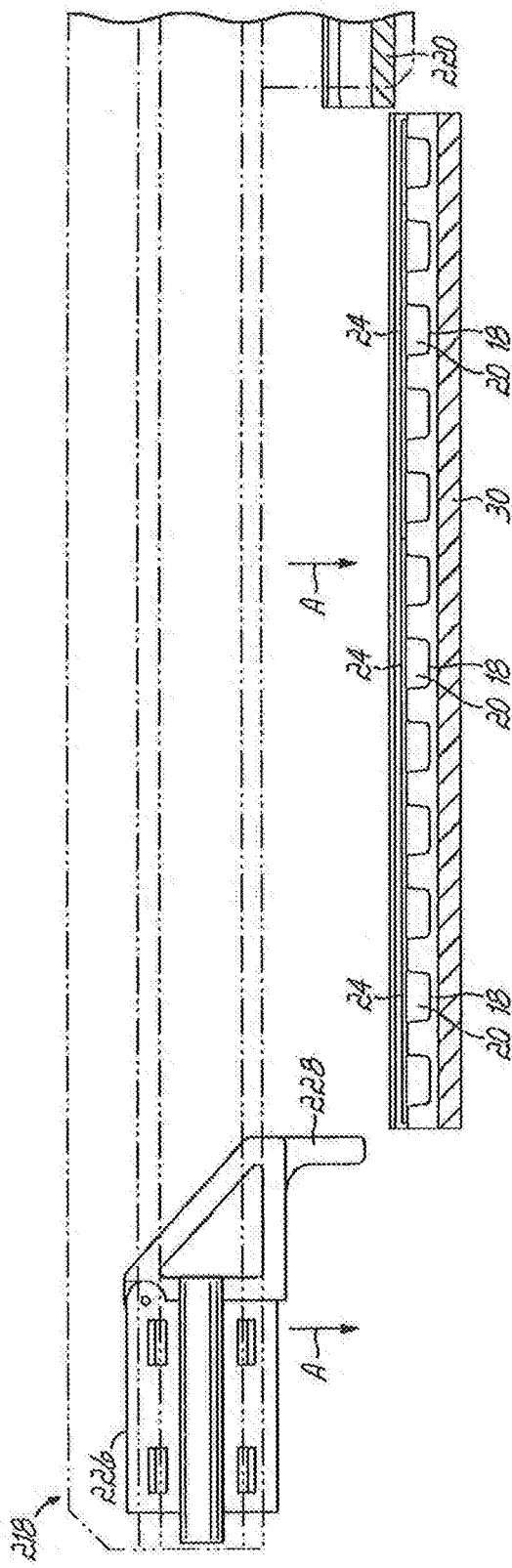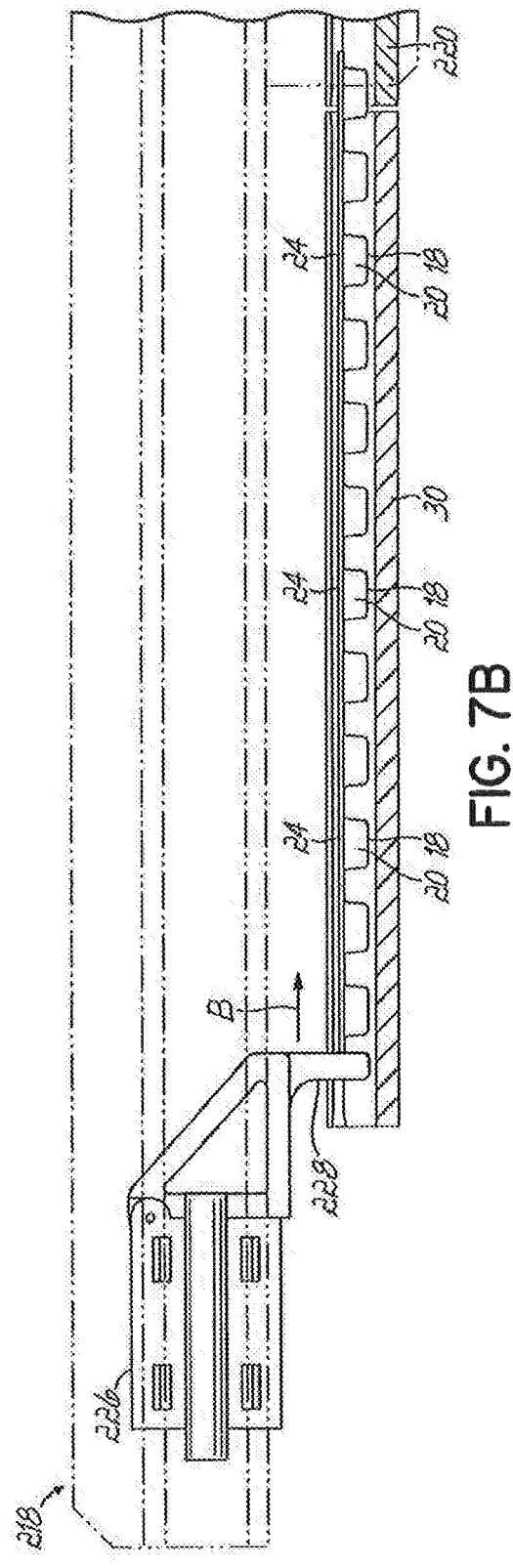

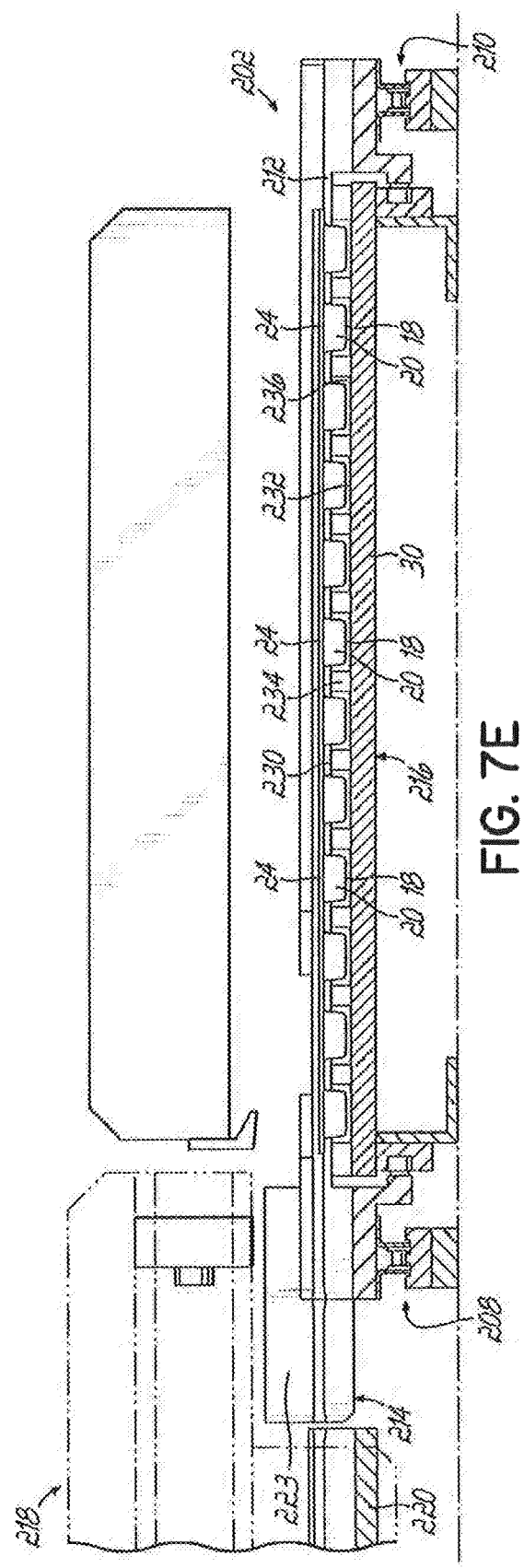

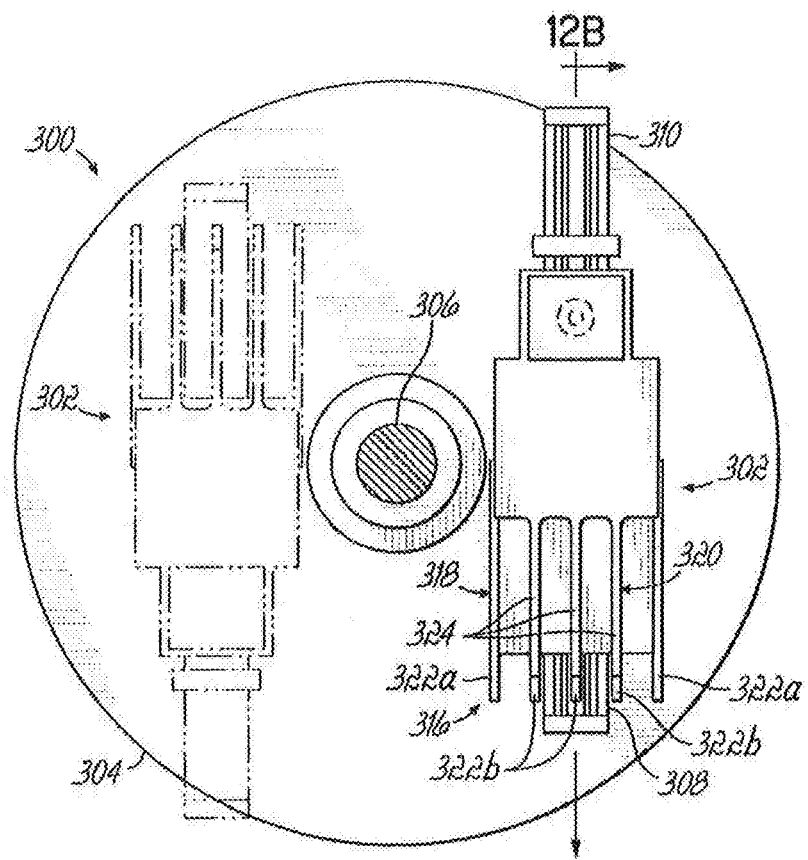
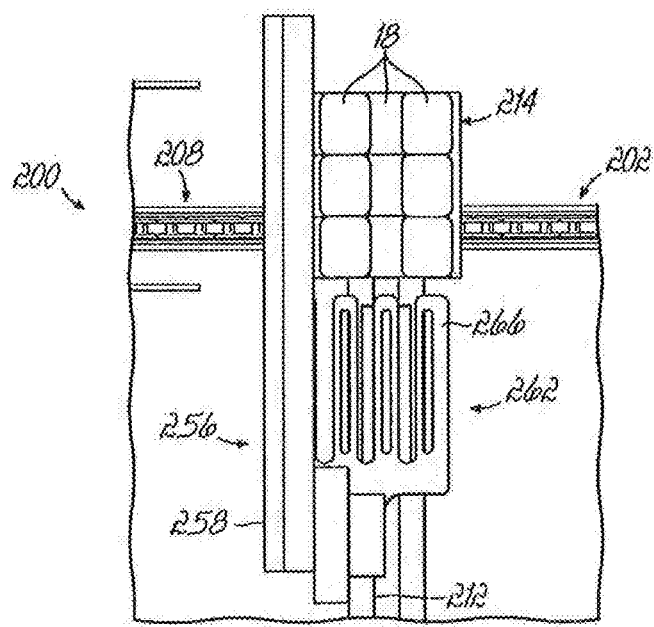
FIG. 12A

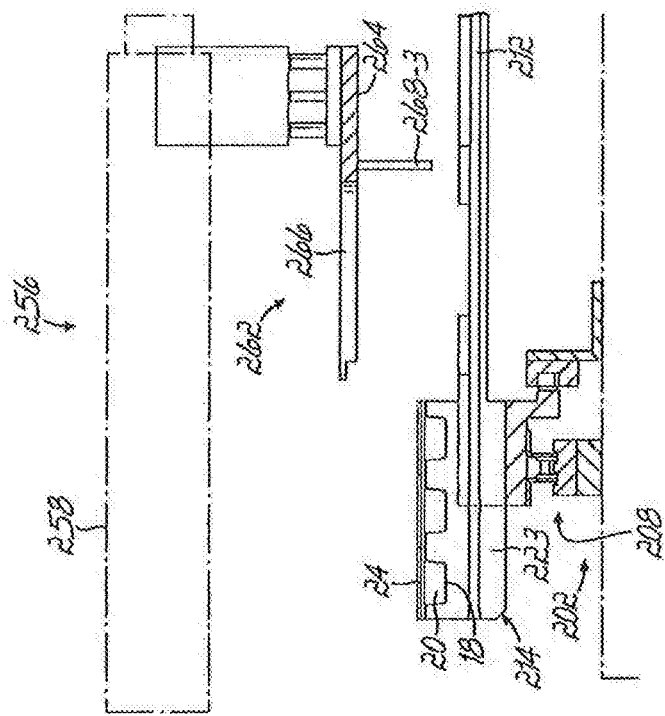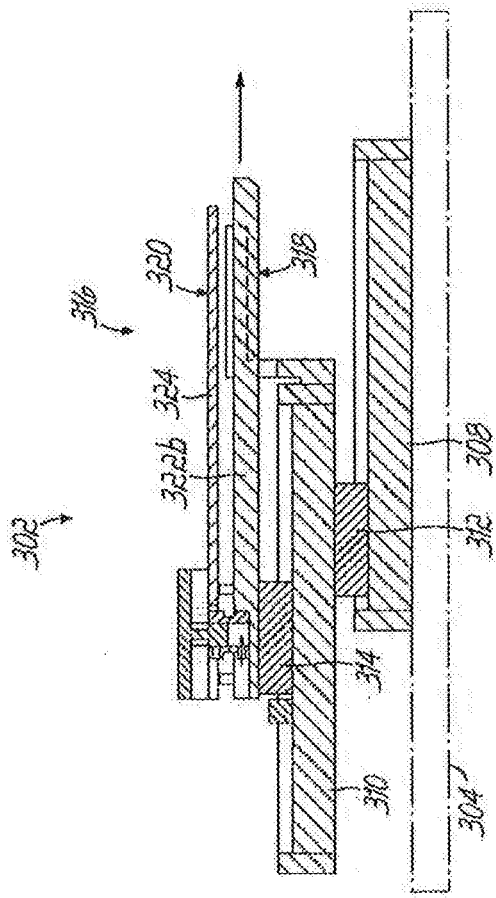
FIG. 12B

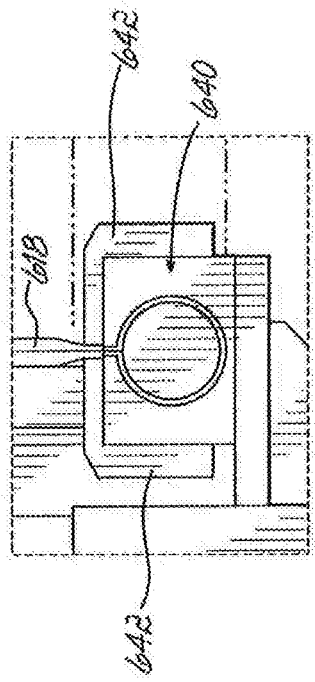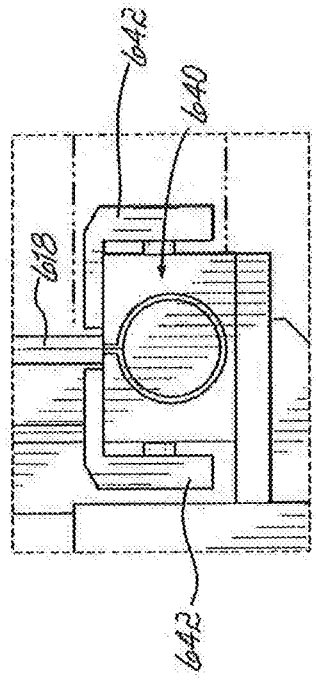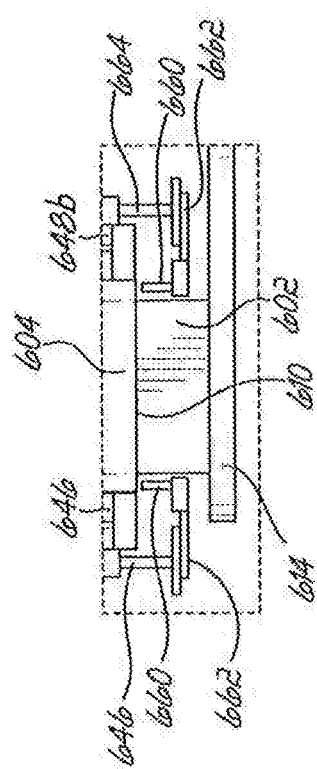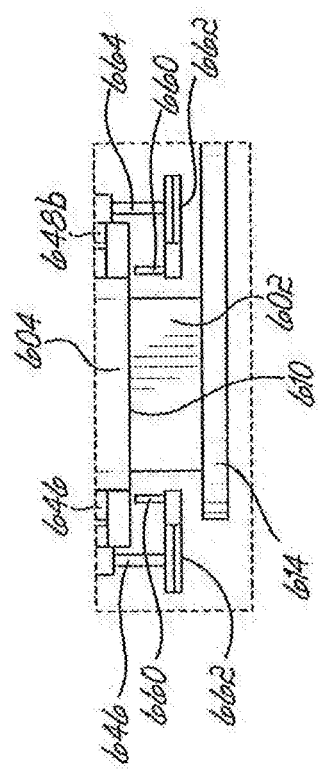

PACKAGING SYSTEM FOR PHARMACEUTICAL DISPENSER AND ASSOCIATED METHOD

CROSS-REFERENCE TO RELATED APPLICATIONS

This application is a continuation of U.S. Ser. No. 18/170,169, filed Feb. 16, 2023, allowed, which is a continuation of U.S. Ser. No. 16/815,916, filed Mar. 11, 2020, now U.S. Pat. No. 11,603,224, which is a continuation of U.S. Ser. No. 15/891,826, filed Feb. 8, 2018, now U.S. Pat. No. 10,618,748, which is a continuation of U.S. Ser. No. 13/659,545 filed Oct. 24, 2012, which claims priority under 35 U.S.C. § 119(e) to U.S. Application No. 61/550,787, filed Oct. 24, 2011, the contents of each of these applications are incorporated herein by reference in their entirety.

BACKGROUND OF THE INVENTION

Field of the Invention

This invention is related to those disclosed in U.S. patent application Ser. No. 09/995,907, filed Nov. 28, 2001; U.S. patent application Ser. No. 11/962,210, filed Dec. 21, 2007; U.S. Provisional Patent Application Ser. No. 60/883,419, filed Jan. 4, 2007; International Application No. PCT/US07/87905, filed Dec. 18, 2007 and published as WO 2008/085673; U.S. Provisional Patent Application Ser. No. 61/120,209, filed Dec. 5, 2008; U.S. patent application Ser. No. 12/559,630, filed Sep. 15, 2009 and published as U.S. 2010/0176145; U.S. patent application Ser. No. 12/559,601, filed Sep. 15, 2009, and published as U.S. 2010/0172724; U.S. patent application Ser. No. 12/617,075, filed Nov. 12, 2009 and published as U.S. 2010/0174552; International Application No. PCT/US2009/066756, filed on Dec. 4, 2009 and published as WO 2010/065845; and each of these prior applications is hereby incorporated herein by reference in its entirety.

This invention relates generally to systems and associated methods for packaging pharmaceutical products for delivery to the patient and, more particularly, to automated dispensing and packaging systems and associated methods for delivering pharmaceutical products to individual patients in health care facilities.

Hospitals, long term care and other health care facilities distribute and administer pharmaceutical products to patients in individual doses numerous times per day. Pharmaceutical products such as prescription medications, nutritional supplements and the like are often stored in bulk by pharmacies and are repackaged into containers of multiple doses based on individual prescriptions for retail or outpatient distribution. For inpatient or in-facility distribution, pharmacies also often repackage bulk pharmaceuticals into "unit of use" or "unit dose" packages, for example, multiple blister packs that are connected together in a strip that contain multiple single doses of the pharmaceutical product.

The traditional method for distributing individual dosage units of pharmaceutical products to patients begins with the generation of a patient order by a physician for particular medications. The patient order is delivered to the pharmacy. There, the process of interpreting the patient order, pulling the specified medication or supplements from the drug storage areas, packaging the medication or supplements, and labeling the package is routinely done manually by pharmacy support personnel. After a final check by the facility pharmacist, the packaged individual dosage units are ready for distribution. In large facilities, the packages containing the patient's order are forwarded to individual nursing units where nursing staffers distribute and administer them to the patients.

There are several disadvantages associated with the traditional method of distributing individual dosage units of pharmaceutical products. To begin with, the process is labor and cost intensive. Many separate labor steps are required to fill a single patient order. In large facilities servicing hundreds of patients each day, the staffing requirements to rapidly process patient orders are substantial. In addition, with so many human inputs required in the existing process, there may also be a risk of human error.

As an attempt to address at least some of the issues with respect to staffing requirements and human error, a variety of automated medication dispensing systems have been developed. The current landscape for automated medication dispensing is dominated by a 30-day system utilizing either "bingo cards" or unit doses supplied in 30-day box. The known systems provide a 30-day or other multi-day supply for each patient pass-time for each prescription on a relatively long term basis. In the event the patient is discharged or the treatment is changed, the unused portion of the 30-day supply cannot be cost effectively reused even though the product may be labeled appropriately. The labor cost required to reintroduce the pharmaceutical products back into the distribution system and to maintain the integrity and traceability of manufacturer and expiration data exceeds the value of the pharmaceutical products, even if the substantial restocking fees are paid by the healthcare system. As a result, such unused pharmaceutical products are returned to the pharmacy for disposal. This disposal of unused pharmaceutical products is a significant waste of those resources as well as a detriment to the environment.

A variety of pharmaceutical dispensing systems have been used, some of which are described in the various patent applications noted above. While many such systems can select and accumulate the various medications and supplements for the patients in a LTC or similar facility, most known dispensing systems do not adequately package the dispensed medications and supplements for proper and efficient transfer to, storage at or distribution by the LTC facility healthcare workers. The ability to track, package and verify the dispensed medications and supplements in an efficient, reliable and predictable manner according to the specific needs, desires and preferences of the LTC facility is lacking in most such systems.

Hence, there is a continuing need to provide a system and overall methodology for packaging medication orders for individual patients in health care facilities.

SUMMARY OF THE INVENTION

This invention has many aspects and embodiments generally directed to a process or method and associated system and sub-systems to provide a turnkey solution for dispensing and packaging medications and nutritional supplements to be taken administered in health care settings, including but not limited to long term care (LTC) and assisted living settings.

The process according to one embodiment of this invention includes packaging unit doses and ultimately individually packaged medpass bags for each patient on a 24-hour schedule. Additionally, inventory management is automated and the various safeguards and measures built into this system increase patient safety eliminate waste and increase labor efficiency by reducing and/or minimizing the disposal of unused medications and supplements.

A dispenser for the automated filling and packaging of individual medpass patient orders is utilized. The dispenser provides an automated solution to the efficient and timely preparation of medpass orders handled in LTC and assisted living settings by filling individual medpass orders for each patient. These orders are assembled in a bag of unit dose medications and supplements and individual bags are combined together. The dispenser may be of any design according to this invention, although one such dispenser is disclosed in the patent applications noted above and incorporated herein. The medications and supplements are dispensed according to physicians' orders and placed in packs which are then packed in a tote and delivered to the LTC for distribution. At each step in the process, the unit dose medications and supplements are tracked via a bar code scanner and the status of each unit dose medication is cataloged and regularly updated in the pharmacy information management system (PIMS) database.

The design of the overall system and its individual components allows for physical control of each unit dose package from start to finish without any unit dose package "free fall" in the system. This process is automated and does not rely upon manual sorting. The medpass bags are consolidated into the final shipping container and do not require manual sorting and packing thereby solving many of the problems associated with prior art solutions.

The various safeguards and measures built into the system of this invention include unit dose scanning at various steps as well as personal inspections, as needed, to increase patient safety, eliminate waste and increase labor efficiency by reducing and/or minimizing the disposal of unused pharmaceutical products.

One objective of this system and methodology is to avoid the need for disposal of prescriptions medications and nutritional supplements thereby attacking the waste and inefficiency issues at their source. This invention in one embodiment is a packaging system for prescriptions, medication and nutritional supplements. Positive control of each unit dose package is maintained throughout the entire process. In other words, gravity feed and the random nature of medications freefalling through the system is avoided according to one aspect of this invention.

The individual pharmaceutical products are packaged in a primary package referred to as unit dose packages and multiple such unit dose packages are dispensed for each medpass order. Individual medpass orders for each patient are assembled in a med pass bag as a secondary package of unit dose pharmaceutical products and individual med pass bags are stacked together. The staked bags are then packed in a travel pack as a tertiary package and delivered to the LTC for distribution. At each step in the process, the unit dose pharmaceutical products are tracked via a bar code scanner and the status of each unit dose is cataloged and regularly updated in the information management system database.

The various embodiments of this invention provide primary (i.e., unit dose packages), secondary (i.e., medpass bags) and tertiary packaging (i.e., travel packs containing one or more medpass bags) for unit doses of medications. One aspect of this invention is a dispensing collation table which in one embodiment is an automated assembly that re-orients a linear row of up to twelve unit dose packages into a shingled, four by three array. The resulting matrix is a flat, nested, compact structure that allows for robust vision verification and simplified loading into a secondary package or medpass bag.

Another aspect of this invention includes vision inspection systems which are utilized to inspect the unit dose array noted above prior to and after secondary packaging. Prior to packaging, a 2D barcode on each unit dose blister package contained in the array is inspected and verified against an order database. Post packaging, a second vision system is utilized to verify that the correct number of unit dose packages is present in the med pass bag to ensure none were lost in the packaging process. All images from both inspections are saved in electronic storage medium where they can easily be retrieved and viewed by operations personnel. Any unit dose packages or medpass bags not meeting inspection requirements are automatically removed from the system and scheduled for re-processing. The system is also able to detect unit dose package presence, even if the barcode cannot be read.

Another aspect of this invention is the secondary package, also known as the 'med-pass' bag which has various advantageous design features including:

a) The front of the bag in one embodiment is an opaque material such as white LDPE, white HDPE or another such material so that on demand printing can be utilized to print specific order items such as patient name, room number, medpass time and medications contained within the bag.

b) The back of the bag in one embodiment is a clear, translucent, transparent or non-opaque material such as LDPE, HDPE or another material which enables both human and machine vision to view the specific labels of each unit dose medication contained within the bag.

c) Double sided tape in one embodiment is utilized between the two LDPE bag layers to facilitate reclosing of the bag if all medications are not administered at the same time.

d) Three tear perforation lines in one embodiment are punched, slit, or otherwise weakened across the bag to facilitate multiple methods of use:

l. A first top perforation allows for tearing open of the bag above the double-sided tape line (item c above) so that the bag can be resealed.

n. A second top perforation provides a convenient method of separating all patient information contained at the top of the bag from the listing of medications found on the rest of the bag. This feature satisfies HIPAA regulations. After HIPAA regulations have been satisfied, all other materials can be handled as normal waste without a shredding requirement.

m. A bottom perforation allows the bag to be opened at the bottom so all medications can be removed if the reclosable feature is not to be used.

e) The invention in one embodiment utilizes technology to form pouches on line.

f) Resident, facility and medication information in one embodiment is printed in specific locations on the white LDPE to enable efficient storage in the cart, and to allow the nurse to quickly find the resident medications at a given administration time. Further, the printing on the bag can be ordered in alphabetical order to assist with verification against the Medication Administration record.

g) Printing on the medpass bag and unit dose blisters offers verifiable three-way medication checks.

h) Medpass bags can be printed with unique bag identification to verify the correct medications are loaded and the bag subsequently tracked through the dispensing process.

The addition of double sided tape to the interior of the medpass bag according to another aspect of this invention solves the problem of providing a reclosable bag to end users. In addition, the clear back of the medpass bag (in combination with the unit dose package orientation noted herein) provides a clear window for visual inspection of unit dose package content labels. Med pass bag forming on line permits use of a wider variety of materials at a significantly reduced cost and improved delivery time.

Another aspect of this invention is the tertiary package which is a sealed clear LDPE material travel pack that can hold from one to thirty secondary packages (medpass bags). The tertiary packages or travel packs are of variable length to accommodate any number of medpass bags needed for that medication cart. The clear material allows visual inspection of the contents without opening the sealed pack. Additionally, the pack is perforated in such a manner to allow both ease of opening and a re-closable feature utilizing a print and apply label that is affixed over the perforation area. The pack is disposable such that return to the pharmacy is not required.

The methodology to load the medpass bags into the tertiary package permits a significant packaging density thereby reducing both delivery costs and permitting increased storage quantities in the medication carts at the LTC facilities.

Prior art systems utilized a mechanism to drop loose unit dose packages into the secondary package or med pass bag. This method produced unpredictable results due to the random nature of how the unit dose packages are settled into the medpass bag as well as a bag thickness several inches thick. Further, due to the random orientation of unit dose packages, only 8 shallow unit dose packages (or 6 deep) could be loaded into a single medpass bag. The system of this invention orients all unit dose packages and allows loading in a controlled, predictable manner. This invention permits any mixture of shallow/deep unit dose packages up to 12 per medpass bag.

Prior art for unit dose vision inspection for such systems consisted of a complex array of three vision systems prior to packaging. A post packaging inspection was not possible due to a lack of predictable orientation of the unit dose packages. This invention utilizes one simplified vision system prior to packaging to inspect the 2D barcodes of each unit dose package. In addition, a post packaging camera utilizes a novel method of counting the number of unit dose packages in the sealed medpass bag as a quality inspection.

Prior art systems of this type consisted of a fixed volume, opaque corrugated box. This invention utilizes a clear travel pack that provides for simple inspection of the contents. It also greatly increases packing density since it can be sealed at variable lengths dependent on the number of secondary packages contained within. Prior art systems required return, cleaning and reuse of such packaging, but this invention ensures product is not accidentally discarded or returned.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIGS. 7A-7E are cross-sectional sequential views taken along line 7A-7A of FIG. 4 showing unit dose packages being transferred from a main conveyor of the dispensing system into the collation module according to one embodiment of this invention;

FIG. 12A is a top plan view of the arrangement shown in FIG. 12 with portions of the components removed for clarity;

FIG. 12B is a cross-sectional view taken along line 12B-121 of FIG. 12A;

FIGS. 39A and 39B are sequential views of the enlarged section 39 shown in FIG. 38;

FIGS. 40A and 40B are sequential views of the enlarged section 40 shown in FIG. 38;

DETAILED DESCRIPTION OF THE INVENTION

Figure 1:
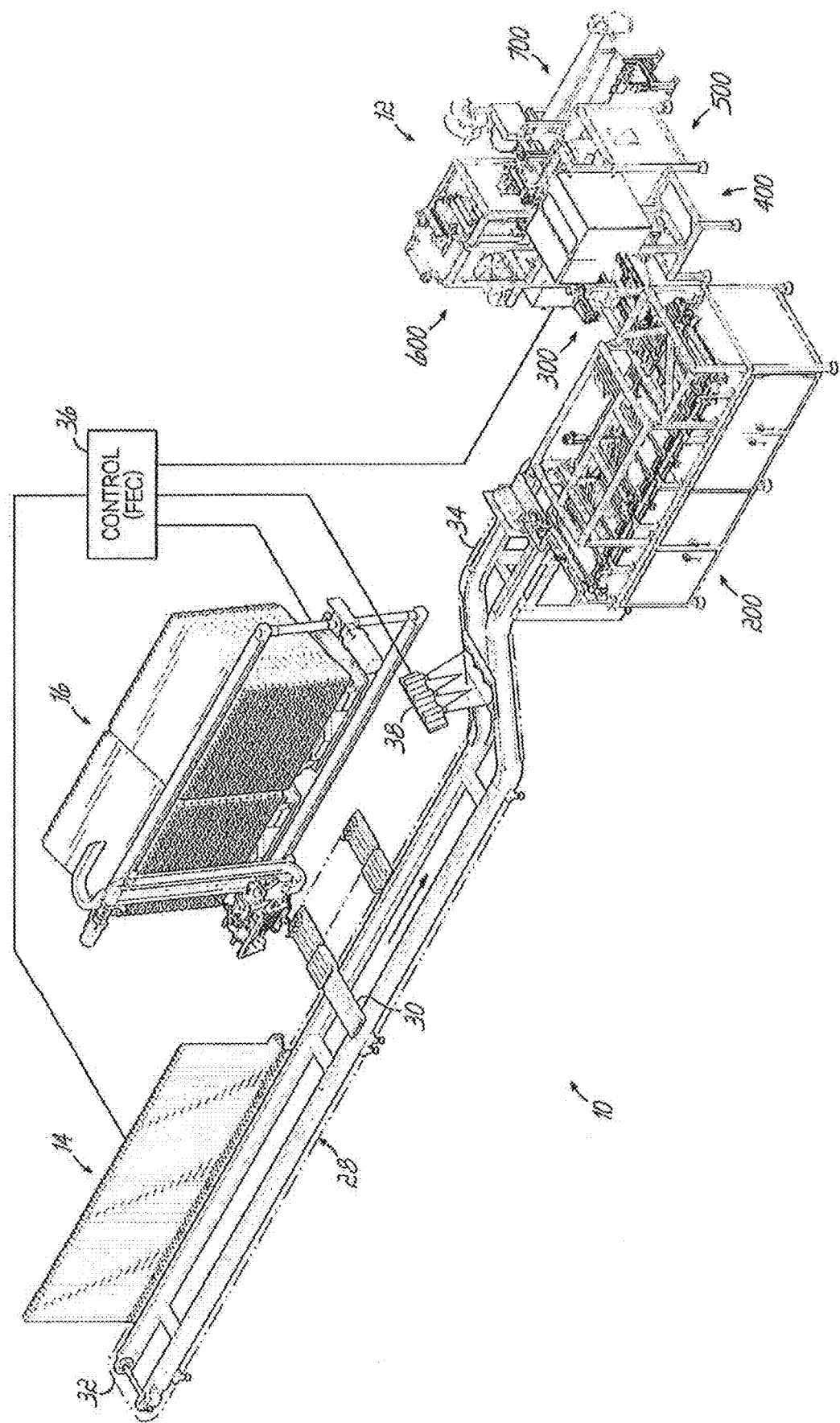
FIG. 1 is a perspective view of a pharmaceutical dispensing and packaging system according to one embodiment of this invention.

A dispensing system 10 according to one embodiment is shown in FIG. 1 and is configured to store and dispense individually packaged and labeled doses of medications/supplements, and to assemble the dispensed medications/supplements into individual medication orders, such as time-pass medication orders to be delivered to a long-term care (LTC) facility, for example. The dispensing system 10 shown and described herein is one example of such a system that can be utilized in conjunction with a packaging system 12 as shown and described herein. The dispensing system 10 of one embodiment is divided into distinct modules that are dedicated to dispensing the medications/supplements based on the demand, or order frequency, of those items. In the exemplary embodiment shown, a first module 14 is configured to dispense medications/supplements having a relatively high-demand or order frequency, and a second module 16 of the dispensing system 10 is configured to store and dispense medications/supplements having a relatively lower demand or medium order frequency.

In the dispensing system 10 embodiment shown and described herein, the medications/supplements are provided in unit dose packages 18 sized to receive an individual dose of a particular medication/supplement, commonly referred to as a blister pack. With reference to FIGS. 16A-D, an exemplary unit dose package 18 includes a base portion 20 defining a cavity for receiving the individual dose of the medication/supplement 22, and a generally planar closure panel 24 disposed over an open end of the base portion 20. The peripheral dimensions of the blister capsule base portion 20 of the unit dose packages are smaller than the perimeter dimensions of the upper, generally planar closure panel 24 of the packages 18. The packages 18 may be provided with information 26 related to the medication/supplement 22 contained in the packages 18, such as the name of the medication/supplement 22, the manufacturer, the date manufactured, the lot number, and/or other information. In the embodiment shown, information 26 is provided on the closure panel 24 and includes machine-readable information, such as a bar-code or QR code, which may be used to facilitate the automated storing, inspecting, tracking, dispensing, and packaging of orders.

With continued reference to FIG. 1, the dispensing system 10 of one embodiment further includes an endless main conveyor 28 with a number of carriers 30 that move past the first, high-demand module 14 and the second, low-demand module 16 to collect ordered medications/supplements and carry them to a designated downstream location for further processing and packaging. In the embodiment shown, a first, upstream end 32 of the main conveyor 28 is positioned adjacent the high-demand module 14. The carriers 30 are moved along the main conveyor 28 past the high-demand module 14 and the low-demand module 16 toward a second, downstream end 34 where the medications/supplements are packaged in the packaging system 12 into boxes, cartons or totes for delivery to the LTC facility. Each carrier 30 defines a dedicated or designated space on the main conveyor 28 for a particular order.

The main conveyor 28 thereafter carries the carriers 30 to the packaging system 12 for final packaging and assembly of the patient orders. During processing of the packages 18, the dispensing and packaging systems 10, 12 are each configured to maintain positive control of the medications/supplements 22 and packages 18 such that no medication/supplement 22 is allowed to "free fall" during the dispensing and packaging processes.

After the unit dose packages 18 of medications/supplements 22 for an order have been transferred from the modules 14, 16 to the assigned carrier or carriers 30 on the main conveyor 28, the carriers 30 continue along the main conveyor 28 to the packaging system 12 for subsequent processing into appropriate containers for delivery to the one or more LTC facilities. A camera station with at least one sensor 38 may be positioned downstream of the low-demand module 16 and upstream of the packaging system 12 to verify the medications/supplements 22 in the carriers 30 via the bar code 26 on each unit dose package 18 in the carrier 30.

The dispensing system 10 further includes a control 36 configured to receive orders for medications/supplements and to process the orders for delivery to a LTC facility. Orders may be electronically received by the control 36 from one or more LTC facilities, such as by transmission over a network, or by any other suitable method. Alternatively, orders can be input directly into the control 36 via an appropriate interface, such as a keyboard or other suitable devices. The control 36 identifies which medications/supplements 22 are required from the high-demand module 14 and the low-demand module 16 to fill each order. In one embodiment, the orders corresponding to each medication pass to be administered to a particular patient for that particular day are processed by the control 36 such that the unit dose packages 18 of medications/supplements 22 for each medication pass to be administered to the patient are assembled together, and the medpass bags are then grouped together in totes for delivery to the LTC facility.

The control 36 assigns one or more carriers 30 to receive the unit dose packages 18 of medications/supplements 22 for each order. The control 36 then controls the movement of the carriers 30 on the main conveyor 28 through the high-demand module 14 and the low-demand module 16 to receive the unit dose packages 18. The control 36 may be coupled to an order entry database and via a web service the orders are passed to the dispensing system 10 one at a time. Alternatively, multiple orders may be passed at a time, for example, ten orders passed at a time. As such, the remaining, subsequent orders are buffered in the database.

In another embodiment, the dispensing system 10 may be configured to receive and process short turn-around time orders ("stat orders") that are received separately from the periodically received orders from the LTC facilities. The control 36 integrates the stat orders into the orders being processed and may direct the assembled stat order to a separate location for subsequent handling. The control 36 may also be configured to receive signals from various sensors associated with the dispensing system 10 and packaging system 12 to facilitate managing operation of the systems 10, 12.

One aspect of the dispensing and packaging systems 10, 12 of this invention is the structure and process for maintaining positive control (i.e., no free-fall or gravity induced movement of the unit dose packages 18) through the dispensing and packaging operations. This aspect minimizes mishandled, lost, errant or jammed packages 18 in the filling of patient orders.

Labor savings and safety of the systems have been previously identified herein. However, the fact that the control 36 may compare the unit dose package barcode 26 to the prescription order and the medpass bag barcode compared to the carrier ID (and therefore back to the prescription order) at the time of prescription fill is an advantage. This feature is the basis for eliminating the need for added nurse or other practitioner checks often required in manual and other automated dispensing systems (the first being at order entry and the second being at conversion from bulk to unit dose in the prepack operation). The methods of cross-checking the unit dose packages 18, the med pass bag and travel pack back to the original order are a beneficial aspect of this invention.

The dispensing system 10 has been designed to be able to dispense unit dose packaged vials through the medium mover module 16. The unit dose packages 18 for vials would be the same width as other medications or supplements, just longer and possibly deeper.

The dispensing system 10 is very modular. That is to say, if the application or utilization of the system were to go into a new area (acute care, for example) and fewer medications/supplements are required in the medium mover module 16 and more in the high mover module 14 were needed, the design modification of the dispensing system 10 is very easily accomplished. It is a very flexible system design.

The medium mover module 16 angled dispense tubes utilize cylindrical weights of a very specific weight and design to roll through the angled tubes ensuring a constant pressure against the back of the stack of unit dose packages 18, thus keeping the first package to be picked parallel with the pick face.

Some embodiments of the dispensing system 10 included a feature that would allow the placement of miscellaneous single doses into the system, which would then be read and picked for distribution. This is a good feature for 'ultra slow' movers and could be designed to be even more compact with various embodiments of the dispensing system 10.

Figure 2:
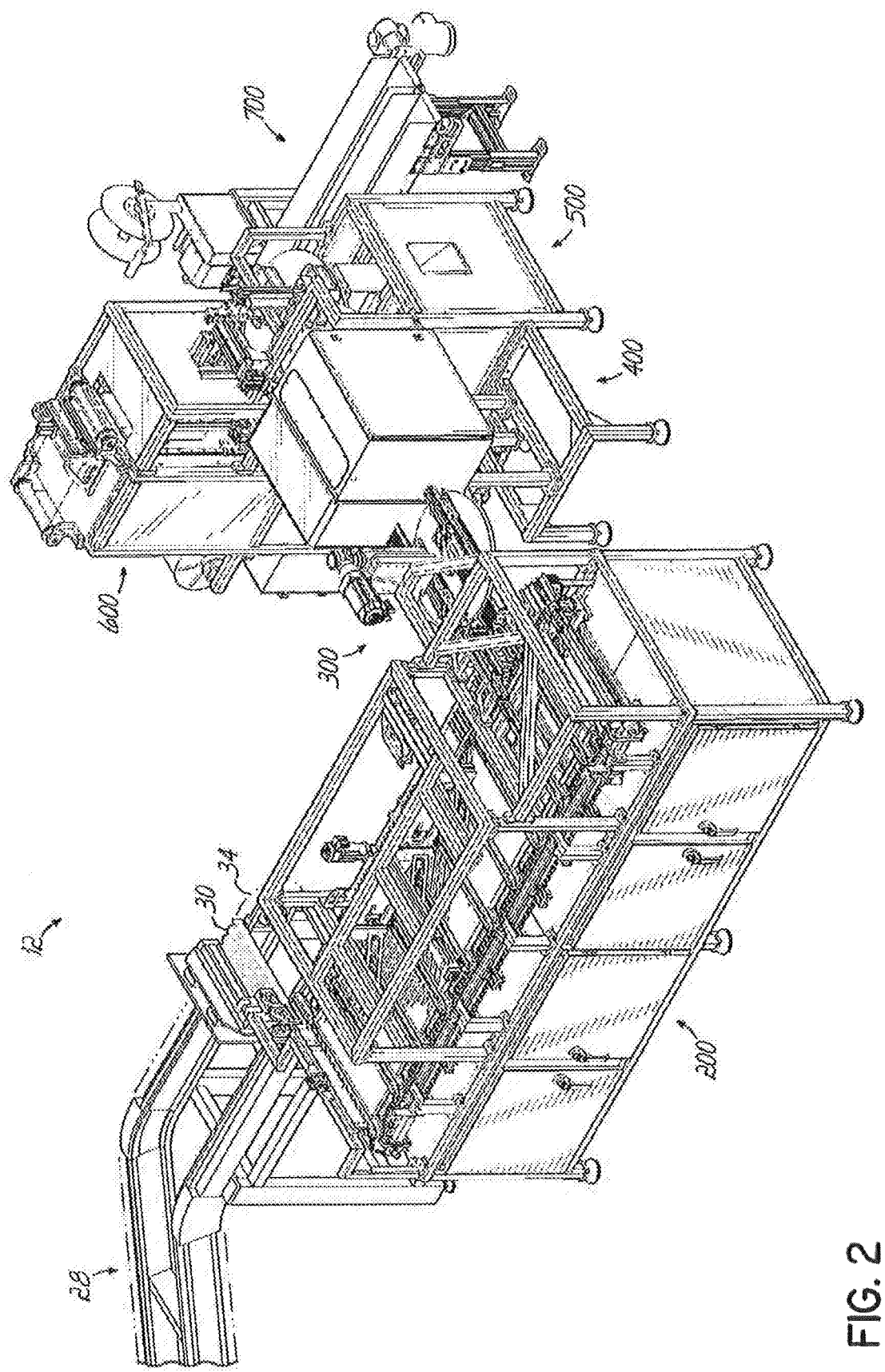
FIG. 2 shows an enlarged perspective view of a packaging system according to one embodiment of this invention for use with the pharmaceutical dispensing system.

Referring to FIG. 2, the packaging system 12 is shown in perspective view and is located at the downstream end 34 of the main conveyor 28. The unit dose packages 18 for each of the med pass orders are delivered to the packaging system 12 on one or more carriers 30 on the main conveyor 28. The unit dose packages 18 are linearly aligned and arranged on the carrier 30 and may have anywhere from one through twelve unit dose packages 18 on each carrier 30 according to one embodiment of this invention.

As a brief overview and further introduction of the packaging system 12, the unit dose packages 18 are off-loaded from the carriers 30 on the main conveyor 28 to a collation module 200 in which the unit dose packages 18 are initially processed on a collation table conveyor traversing relative to a collation table to be arranged in a 4×3 array on a unit dose package nest.

The array of unit dose packages are extracted from the collation module 200 while being maintained in the array and inserted into a med pass bag in a unit dose insert module 300. The medpass bag is formed from upper and lower plies of material in a med pass bag formation module 400. The array of unit dose packages are transferred from the collation module 200 into the med pass bag being formed by the med pass bag formation module 400 by a unit dose insert module 300. The medpass bag formation module 400 forms the med pass bags around the sequentially delivered arrays of unit dose packages 18 and severs each medpass bag with the unit dose package array therein from upstream medpass bags. Each medpass bag is then delivered to a bag accumulation module 500 which collects all the medpass bags for a given patient, for example, and assembles them in a heat staked bundle. Up to four or more med pass bags may be heat staked together. The stacked medpass bags are then inserted into a travel pack loading module 600 which forms the travel packs and seals the accumulated medpass bags therein. A label printer and offload conveyor module 700 prints a label and applies it to the sealed travel pack which is then deposited onto an offload conveyor. The offload conveyor includes two parallel tracks, one for normal orders and one for stat or special urgent orders. The offload conveyor deposits the labeled travel packs into a tote or other receptacle for delivery to the long term care facility.

Figure 3:
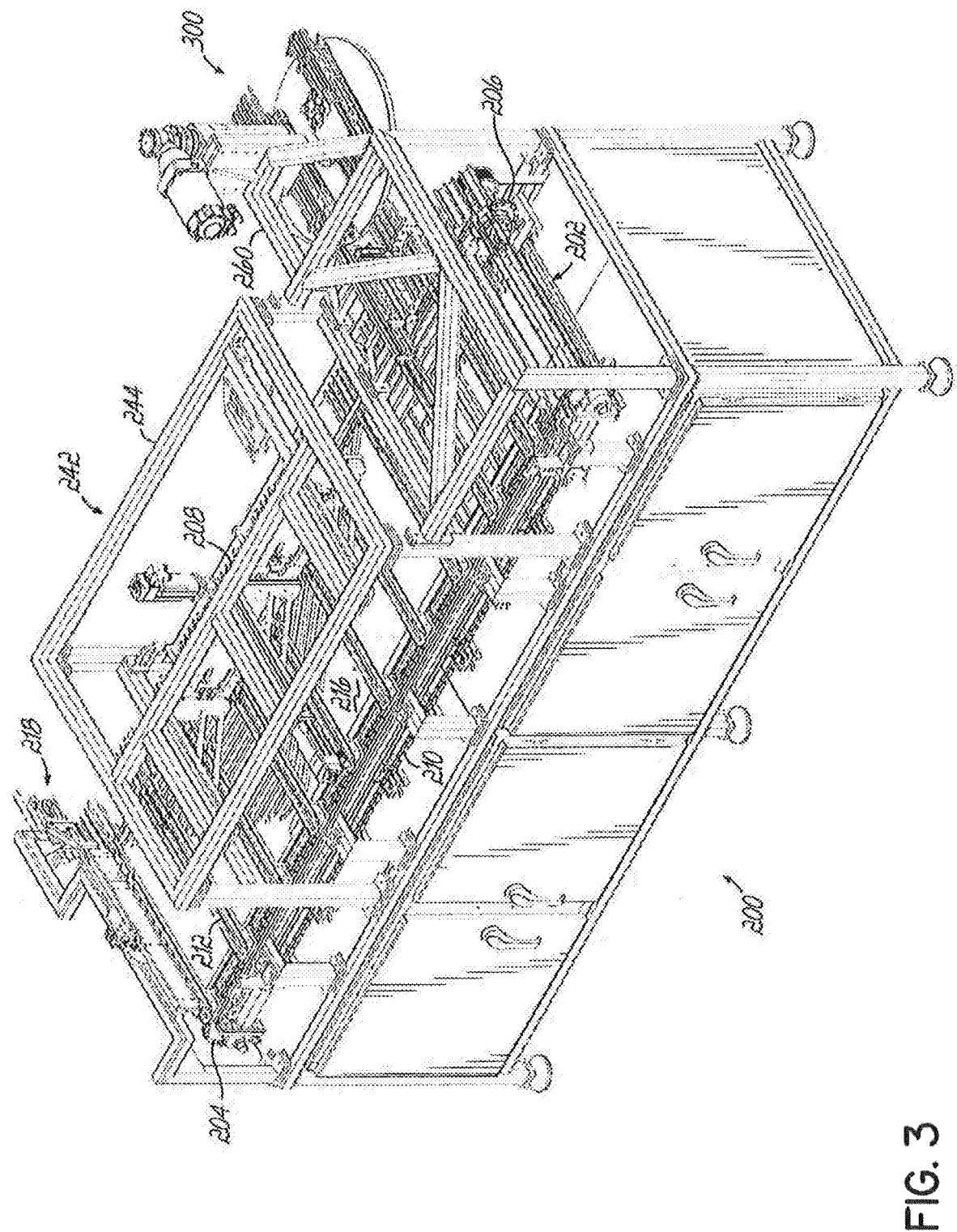
FIG. 3 is a perspective view of a collation module of the packaging system according to one embodiment of this invention.
Figure 4:
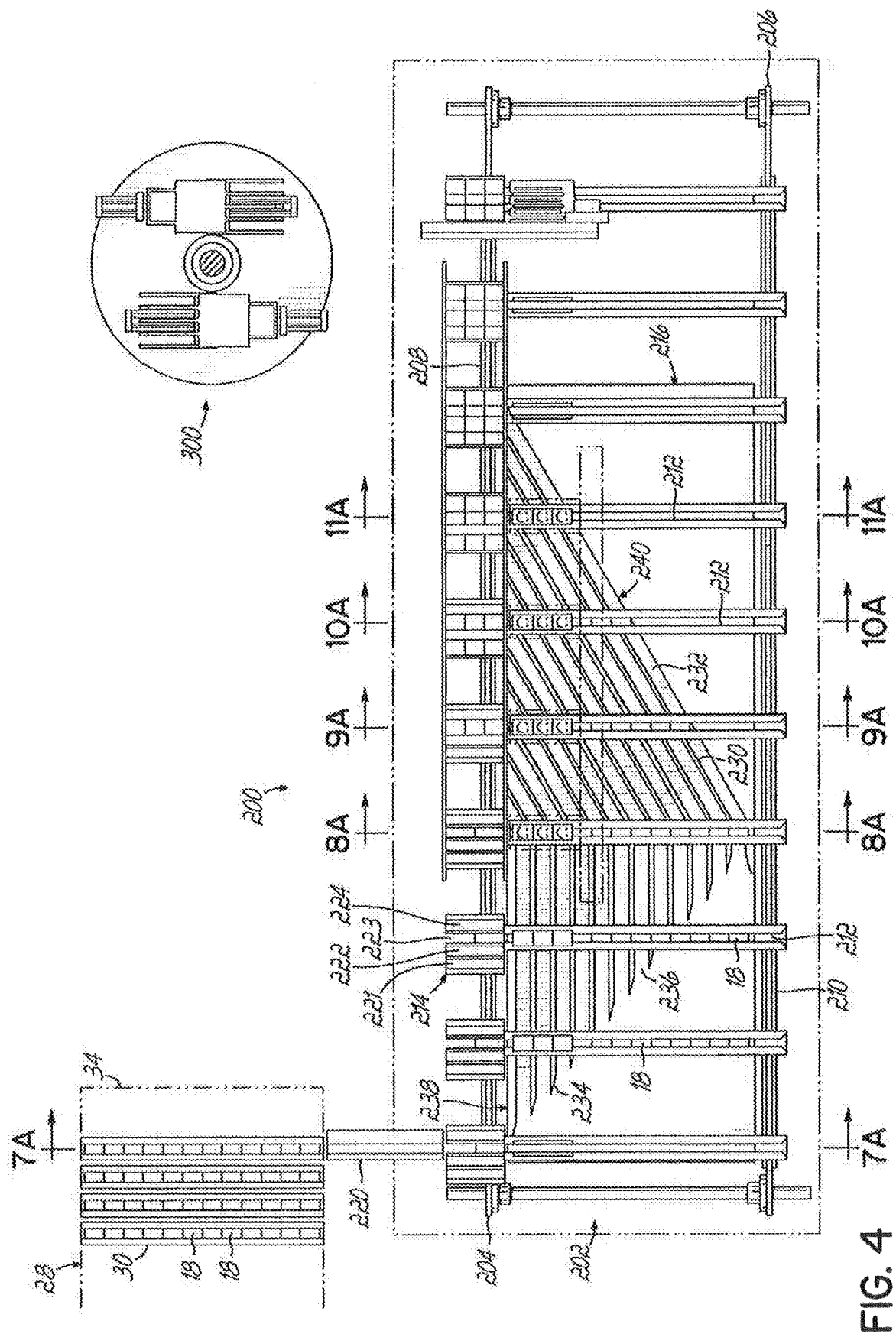
FIG. 4 is a top view partially broken away of the collation module of FIG. 3.
Figure 5:
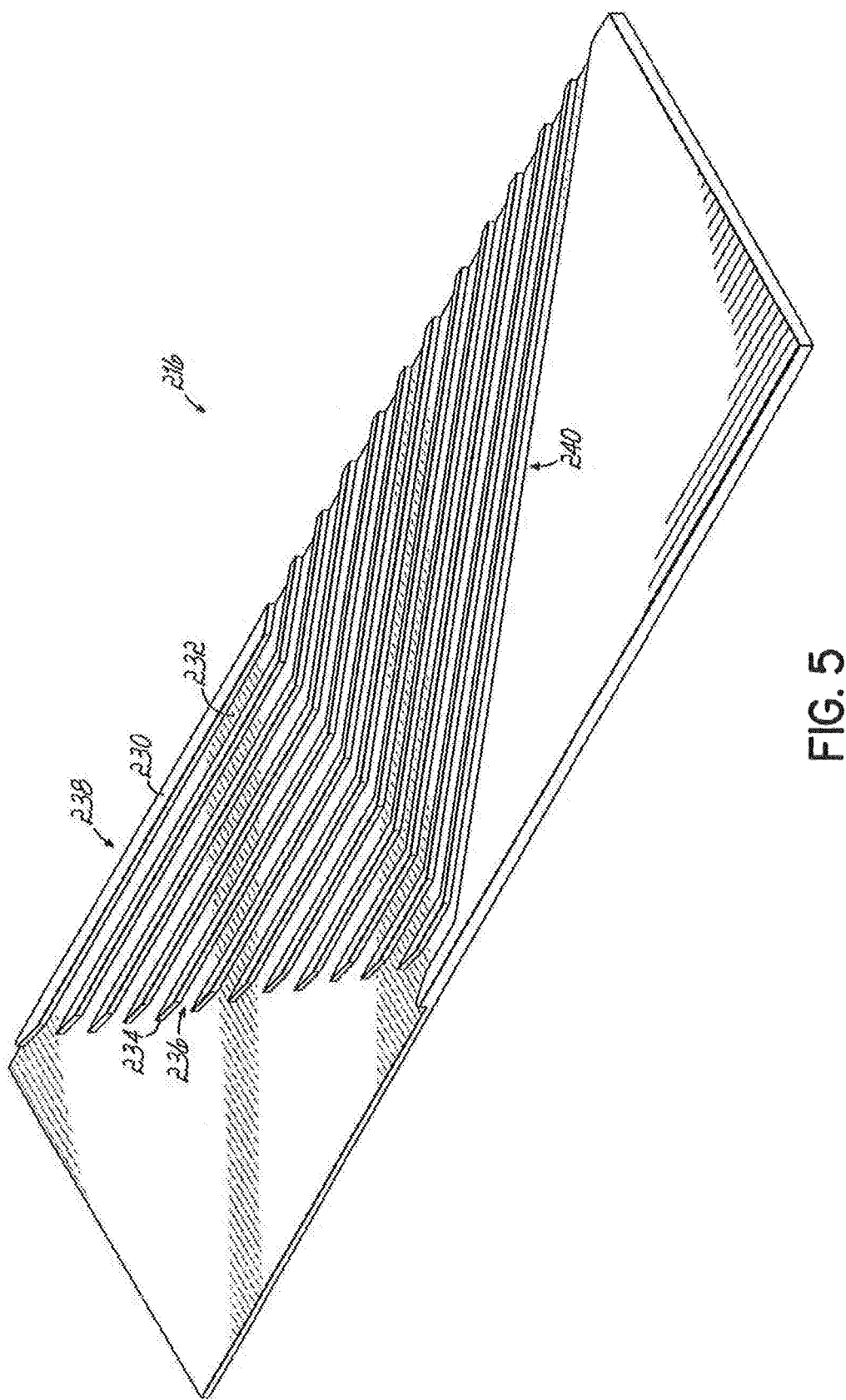
FIG. 5 is a perspective view of one embodiment of a collation table utilized in the collation module.

Referring to FIGS. 2A-7E, portions of the collation module 200 will be described. The collation module 200 includes a collation conveyor 202 which traverses between an upstream end 204 adjacent to the downstream end of the main conveyor 28 and a downstream end 206 adjacent to the unit dose package insert module 300. The collation conveyor 202 has a first or near lateral side 208 adjacent the unit dose insert module 300 and a second, or far lateral side 210 and includes a number of spaced channels 212 extending laterally between the sides 208, 210 of the conveyor 202. Each channel 212 is mounted to a unit dose package nest 214 at the near side edge 208 of the collation conveyor 202 adjacent to the main conveyor 28. The channels 212 and associated nests 214 traverse in an endless path from the upstream end 204 of the conveyor 202 toward the downstream end 206 of the conveyor 202 atop a collation table 216 (FIG. 5). The channels 212 on the collation conveyor 202 are adapted to receive and hold the unit dose packages 18 arranged in a linear array just as in the carriers 30 on the main conveyor 28. The linear arrangement of unit dose packages 18 are transferred from the individual carriers 30 on the main conveyor 28 by a shuttle assembly 218 that pushes the linear arrangement of unit dose packages 18 from each carrier 30 on the main conveyor 28 toward the channels 212 on the collation conveyor 202. The shuttle assembly 218 is shown in FIGS. 3 and 7A-7E. A transfer channel 220 is positioned between the downstream end of the main conveyor 28 and the upstream end 204 of the collation conveyor 202 and is in alignment with the travel path of the shuttle assembly 218 so as to provide a transitional path between the two conveyors.

Each nest 214 on the collation conveyor 202 includes four parallel slots 221, 222, 223, 224 referred to as the first, second, third and fourth slots from the upstream end of the nest 214 toward the downstream end of the nest 214. According to one embodiment of this invention, the third slot 223 on each nest 214 is a bottomless slot and is aligned with the transfer channel 220 and the carrier 30 on the main conveyor 28 as well as the channel 212 on the collation conveyor 202. As such, the shuttle assembly 218 pushes the unit dose packages 18 from each individual carrier 30 on the main conveyor 28 through the transfer channel 220 and the third slot 223 on the nest 214 so as to position the unit dose packages 18 on the associated channel 212 of the collation conveyor 202. This operation will now be described in more detail with respect to FIGS. 7A-7E.

Figure 7C:
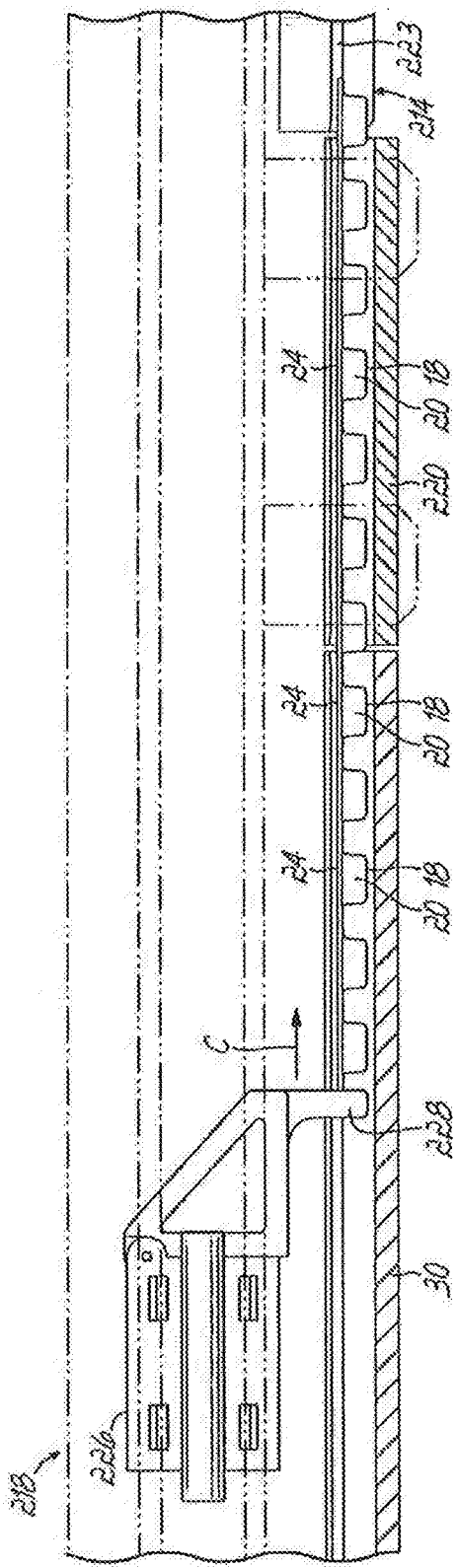

As shown in FIG. 7A, the unit dose packages 18 are positioned on the carrier 30 shown in cross-section in FIGS. 7A-7E and when the carrier 30 is aligned with the transfer channel 220, a pusher 226 on the shuttle assembly 218 moves into position. As shown by arrow A in FIG. 7A, the shuttle assembly 218 and the transfer channel 220 move vertically downward so that the transfer channel 220 is vertically and horizontally aligned with the carrier 30 on the main conveyor 28. Likewise, the pusher 226 is mounted on the shuttle assembly 218 and a downwardly extending pusher bar 228 moves in the direction of arrow B along with the shuttle assembly 218 so as to be positioned on an outer edge of the unit dose packages 18 as shown in FIG. 7B. Once the transfer channel 220 and the pusher 226 are aligned with the unit dose packages 18 and the carrier 30 on the main conveyor 28, the pusher bar 228 translates laterally in the direction of arrow B as shown in FIG. 7B to thereby push the unit dose packages 18 off of the carrier 30 toward the transfer channel 220. Continued movement of the pusher 226 continues to move the unit dose packages 18 off of the carrier 30 and onto and through the transfer channel 220 as shown in FIG. 7C by arrow C. Once the unit dose packages 18 are pushed entirely of the carrier 30 of the main conveyor 28 and the transfer channel 220 to be positioned on the channel 212 on the collation conveyor 202, the pusher 226 translates vertically upward in the direction of arrow D in FIG. 7D and returns longitudinally to the position as shown in FIG. 7A for a subsequent transfer operation on subsequent unit dose packages 18 residing on subsequent carriers 30 of the main conveyor 28.

Figure 7D:
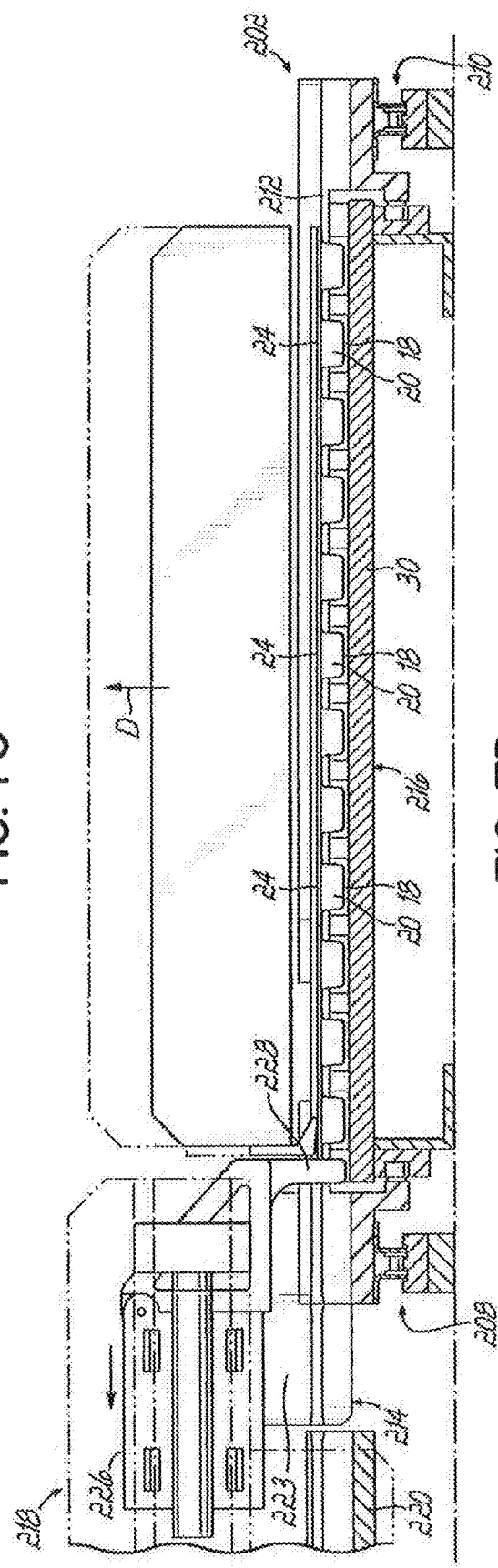

After the unit dose packages 18 pass through the transfer channel 220, they are pushed through the third slot 223 on the nest 214 as shown in FIGS. 7C and 7D by the pusher bar 228 until they reside on the associated channel 212 of the collation conveyor 202. As can be seen in FIG. 7D, the unit dose packages 18 are arranged in a linear array of up to twelve packages 18 extending across the channel 212 on the collation conveyor 202. The packages 18 are positioned adjacent to the near or first lateral side 208 of the collation conveyor 202 adjacent the associated nest 214. The unit dose packages 18 are suspended and supported on the channel 212 by the upper generally planar panel 24 of the package 18 just as they were on the carriers 30 of the main conveyor 28.

The collation table 216 is supported between the upper track of the collation conveyor 202 and the lower return track of the conveyor 202 as shown generally in FIGS. 3 and 4. Referring to FIGS. 4 and 5, the collation table 216 has an upper surface with a number of upwardly projecting ribs 230. The series of ribs 230 form a series of grooves 232 between each adjacent pair of the ribs 230. An upstream end of each rib 230 has a generally angled point 234 which forms a mouth 236 of the groove 232. Each rib 230 includes a generally longitudinal section 238 adjacent the upstream end of the collation table 216 and an angled section 240 adjacent a downstream end of the table 216. The angled section 240 is directed toward the near side 208 of the collation conveyor 202. The ribs 230 form twelve grooves 232 corresponding to the maximum number of unit dose packages 18 housed on each carrier 30 of the main conveyor 28 and on each of the channels 212 of the collation conveyor 202 according to one embodiment of this invention. The upstream ends of the longitudinal sections 238 of the ribs 230 are staggered from the near lateral side 208 of the collation conveyor 202 adjacent the nest 214 to the opposite far side 210 of the conveyor 202 as shown particularly in FIGS. 4 and 5. Each groove 232 is open at the upstream mouth 236 of the groove 232 and at the downstream discharge end of the groove 232 adjacent the near lateral side 208 of the collation conveyor 202.

Once again, consistent with the design concept of each system 10, 12, a transfer of the unit dose packages 18 from the main conveyor 28 to the channels 212 on the collation conveyor 202 maintains positive control of each unit dose package 18 without allowing any of the unit dose packages 18 to free-fall throughout the transfer process.

It will be appreciated by those of ordinary skill in the art that while twelve unit dose packages 18 are shown in each carrier 30 and the associated channel 212 on the collation module 200, any number less or more than twelve may be present on each carrier 30, channel 212 or med pass order according to various embodiments of this invention. The following description is for twelve packages 18 on each carrier 30 and channel 212, although fewer or more packages 18 may be present within the scope of this invention. The unit dose packages 18 are positioned adjacent the near lateral side 208 of the collation conveyor 202 and suspended in the channels 212 over the collation table 216 with the blister portion 20 of each unit dose package 18 projecting downwardly from the channel 212 as shown most clearly in FIG. 8A. As the conveyor 202 and channels 212 move the unit dose packages 18 from the upstream end of the collation table 216 in a downstream direction, the blister portion 20 of each unit dose package 18 is fed into one of the grooves 232 on the collation table 216. The unit dose packages 18-1, 18-2, 18-3 in the first, second and third positions in the channel 212 adjacent the lateral near side 208 of the collation table are sequentially fed into the first, second and third respective grooves 232-1, 232-2, 232-3 on the collation table 216 via the mouth 236 of the aligned groove and the angled arrangement shown in FIG. 4. For clarity, the first unit dose package is identified as 18-1, the second as 18-2 and so on while the associated groove is identified as 232-1, the second groove as 232-2 and so on. As the channel 212 progresses downstream on the collation conveyor 202, the individual unit dose packages 18 are each fed into one of the grooves 232 on the collation table 216 formed by the adjacent ribs 230 and initially into the longitudinal section 238 of the groves 232. As the channel 212 moves with the collation conveyor 202 in the downstream direction, each of the unit dose packages 18 present in the channel 212 is seated within one of the aligned grooves 232.

Figure 6:
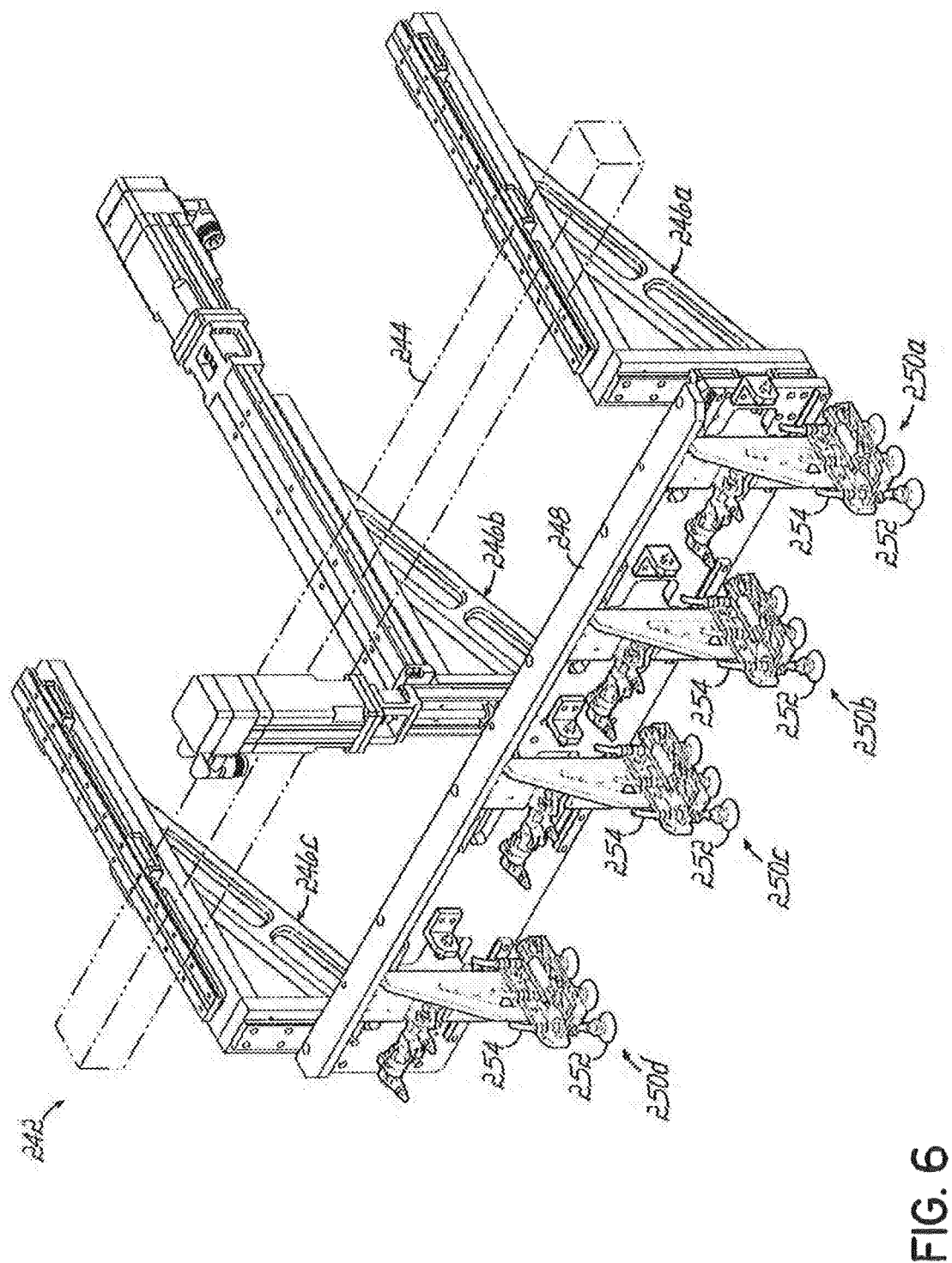
FIG. 6 is a perspective view of a picker system as part of the collation module according to one embodiment of this invention.

The collation module 200 includes a picker system 242 suspended over the collation table 216 for transferring the unit dose packages 18 from the collation table 216 to the nest 214 associated with the respective channel 212. The picker system 242 is shown particularly in FIG. 6 and can also be seen in FIG. 3. The picker system 242 is mounted above the collation table 216 and collation conveyor on 202 an upper frame 244 as shown in FIG. 3. The picker system 242 includes three support frame members 246a, 246b, 246c which are mounted to the upper frame 244 above the collation table 216. A longitudinally extending picker mount bar 248 is supported on the three support frame members as shown in FIG. 6. A series of four picker sub-assemblies 250a, 205b, 250c, 250d are mounted on the mount bar 248 and each picker sub-assembly has three pneumatically actuated pickers 252a, 252b, 252c directed downwardly toward the collation table 216. The picker sub-assemblies are spaced on the mount bar 248, are identical to each other and are identified as first, second, third and fourth sub-assemblies 250a, 250b, 250c, 250d herein. The first picker sub-assembly 250a is upstream from the remaining sub-assemblies and the second picker sub-assembly 250b is upstream from the third and fourth picker sub-assemblies.

Figure 8A:
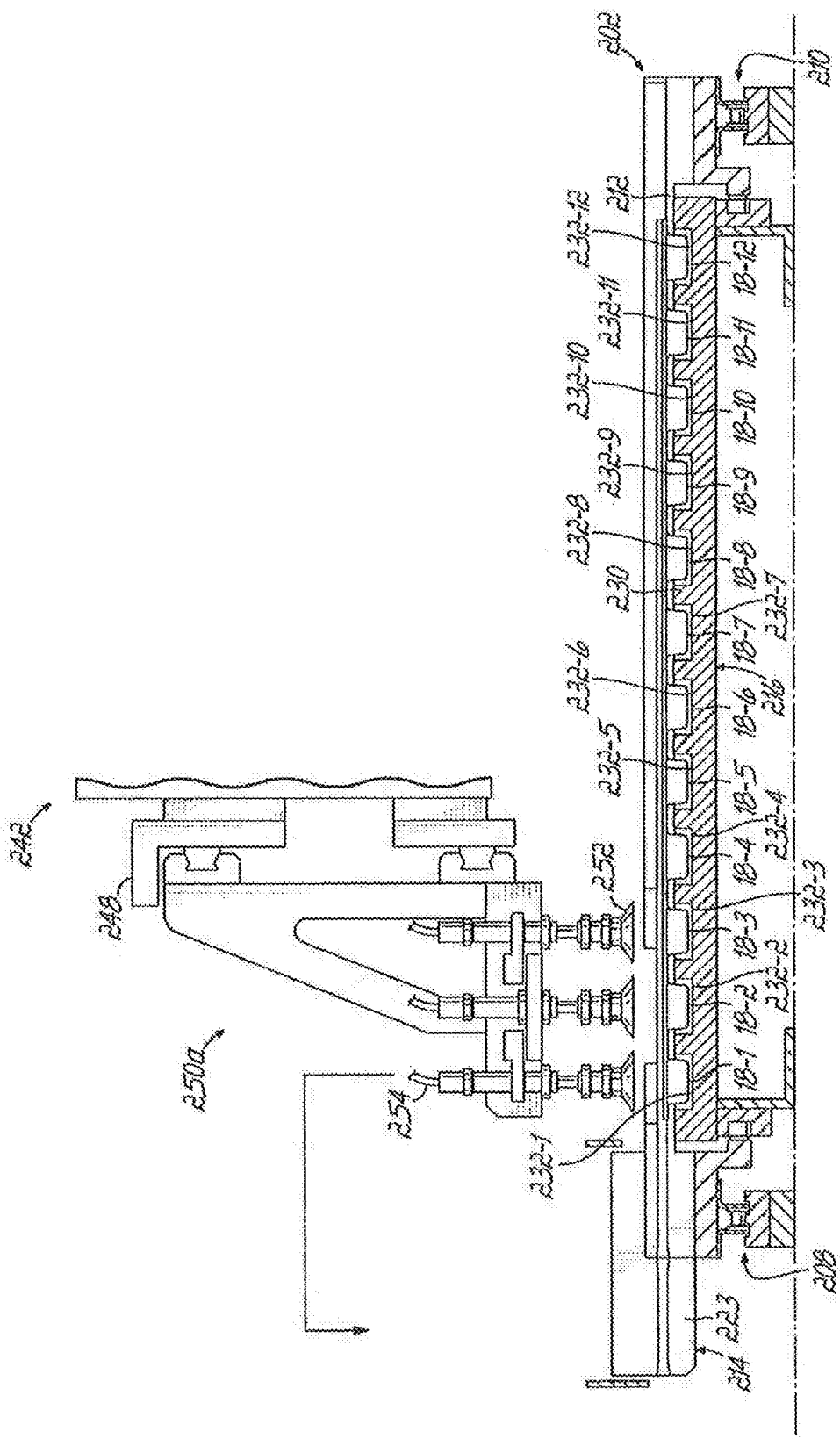
FIGS. 8A-8C are cross-sectional sequential views taken line 8A-8A of FIG. 4 showing a first portion of the picker system transferring a number of unit dose packages from the collation table to a unit dose package nest.
Figure 8B:
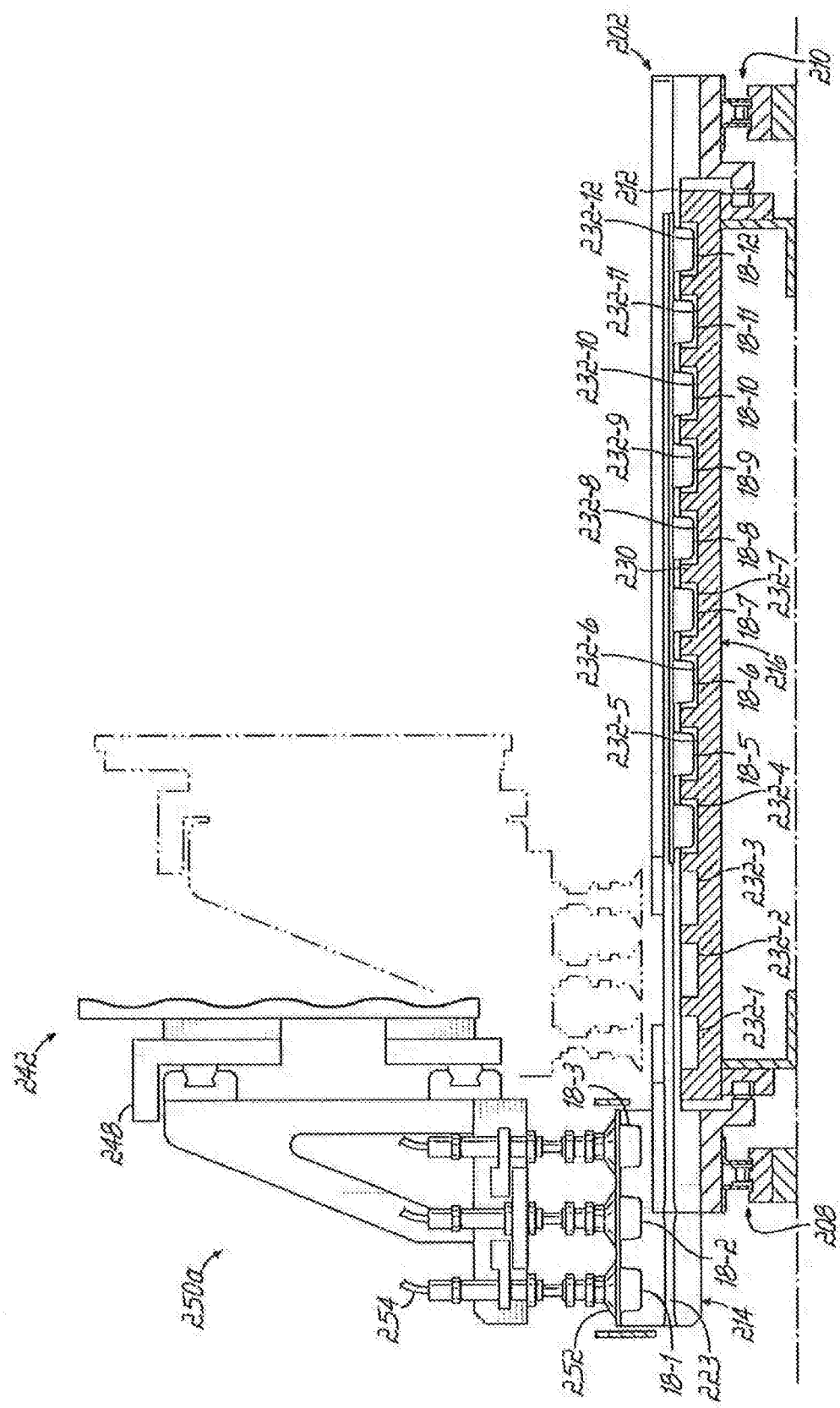
Figure 8C:
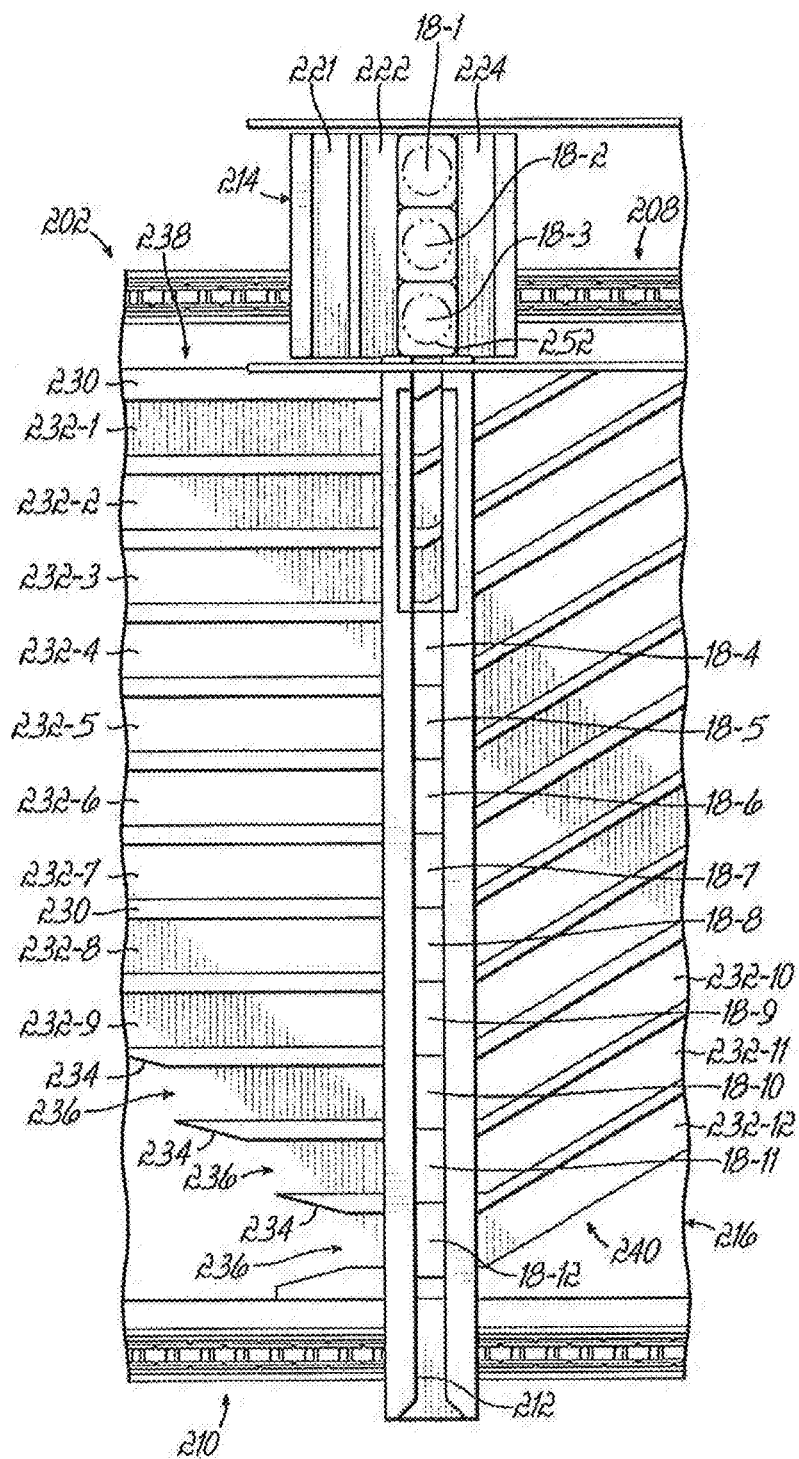
Figure 9A:
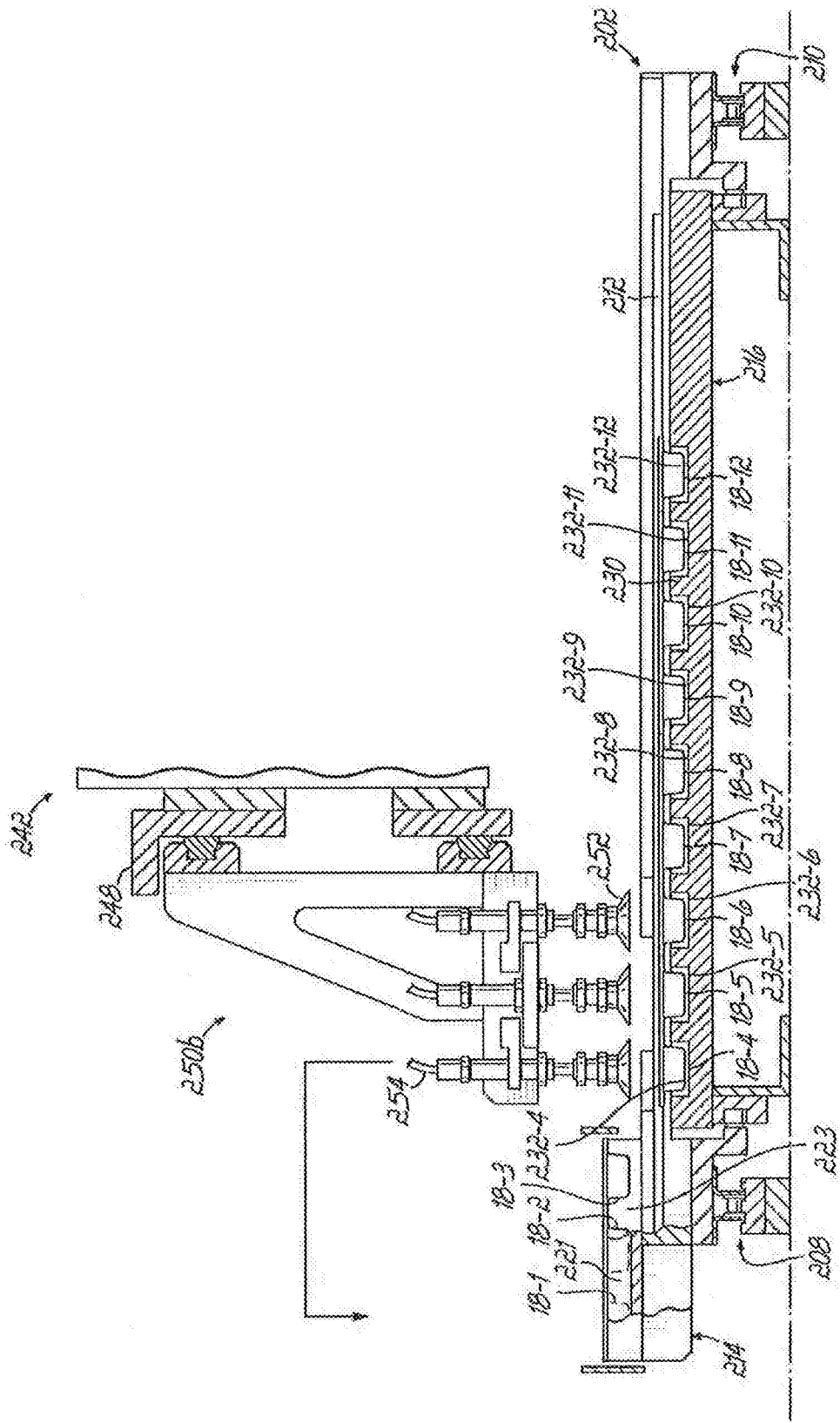
FIGS. 9A-9C are cross-sectional sequential views taken along line 9A-9A of FIG. 4 showing a second portion of the picker system transferring a number of unit dose packages from the collation table to the unit dose package nest.
Figure 9B:
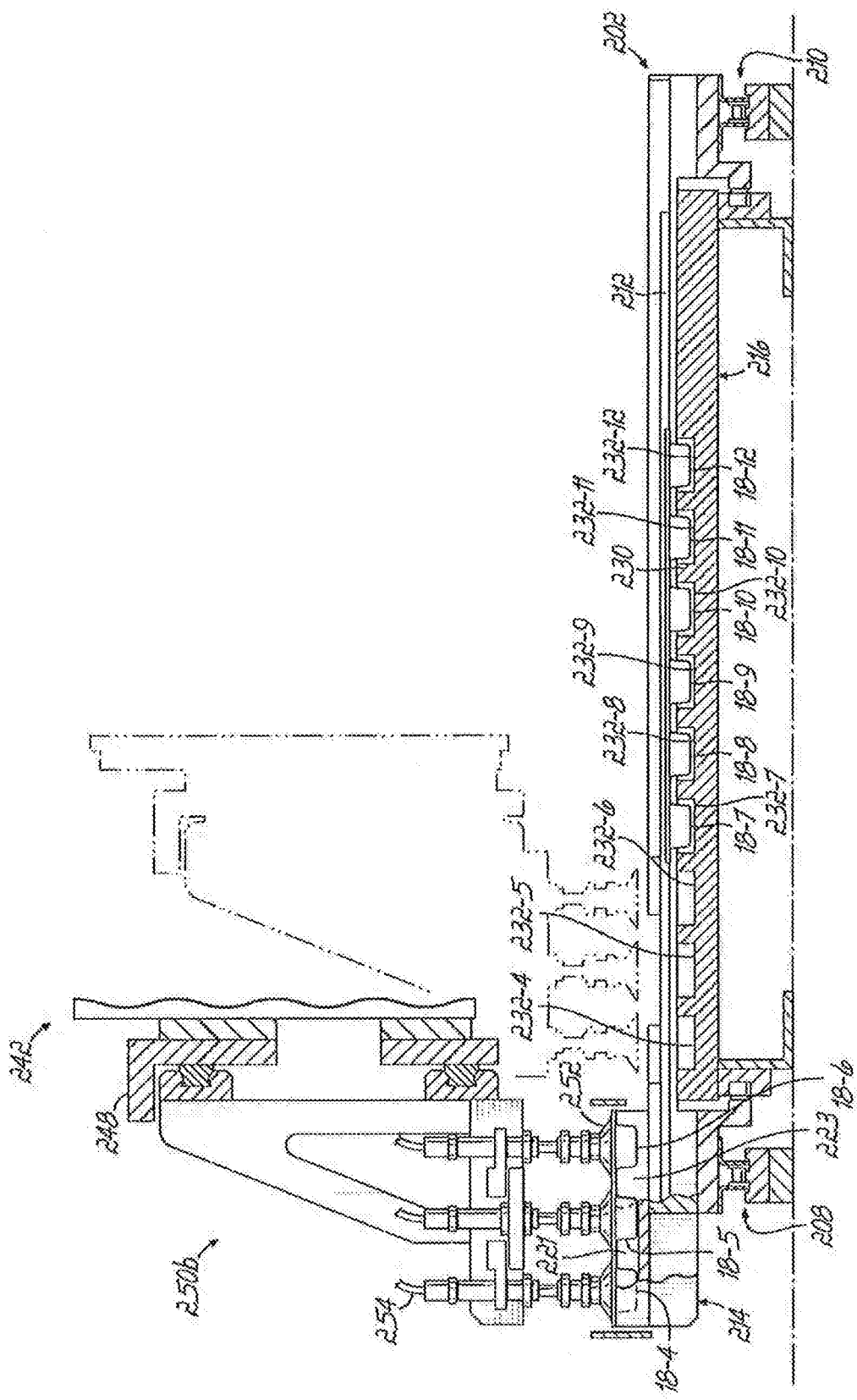
Figure 9C:
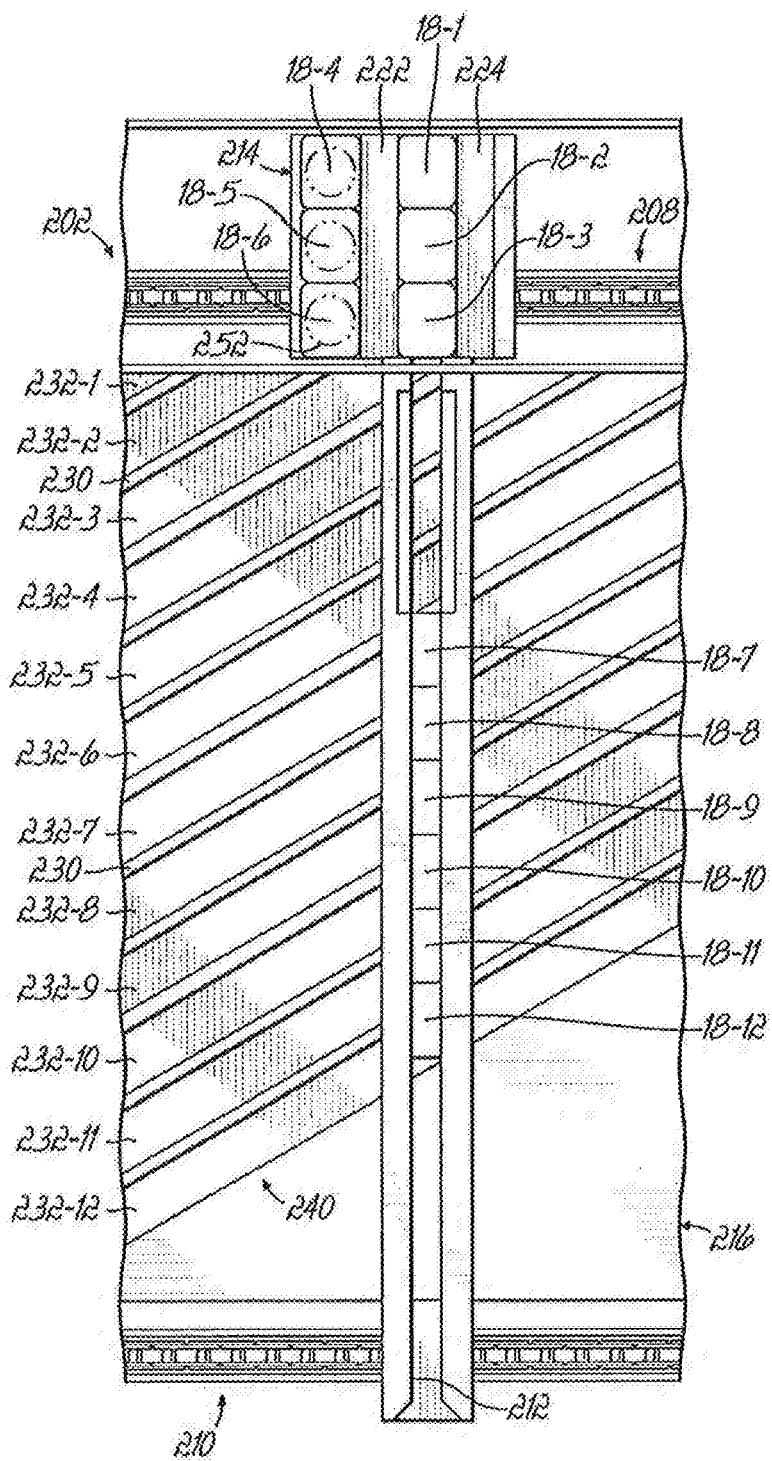
Figure 9D:
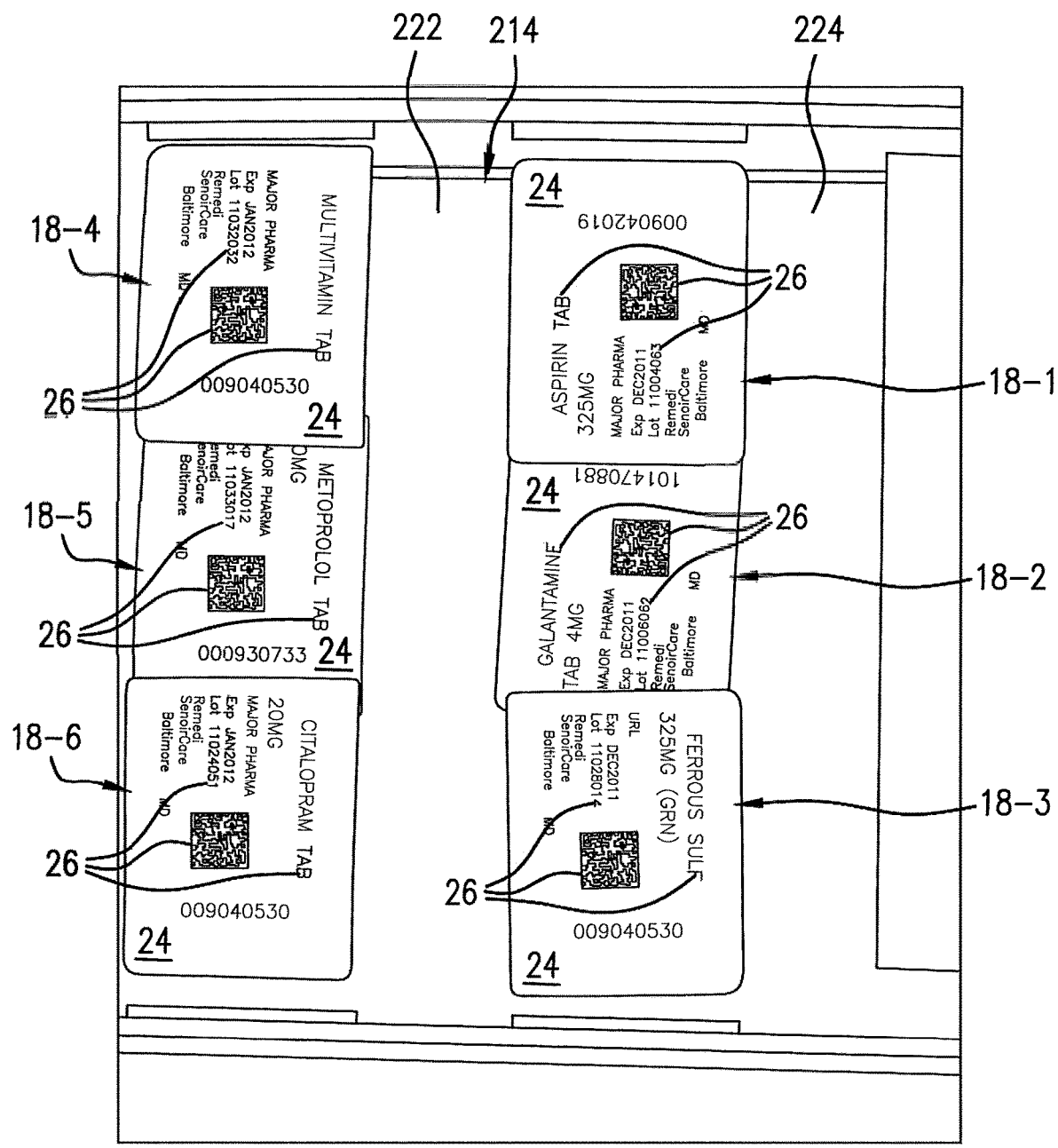
FIG. 9D is a print of a vision inspection picture of the unit dose packages seated in the nest during processing similar to the relevant portion of FIG. 9C.

The first picker sub-assembly 250a is positioned to retrieve the first three unit dose packages 18-1, 18-2, 18-3 adjacent the near lateral side 208 of the collation table 216 as shown in FIGS. 8A-8C. Each of the pickers 252 extend downwardly to contact the upper panel of respective unit dose packages 18 aligned therewith as shown in FIG. 8. A suction tube 254 connected to each picker 252 creates a suction to pneumatically pull the unit dose package 18 upwardly to be held by the picker 252 as shown in FIG. 8B. Once the first, second and third unit dose packages 18-1, 18-2, 18-3 are retrieved by the first picker sub-assembly 250a, the first picker sub-assembly 250a retracts upwardly and extends laterally toward the nest 214 as shown in FIG. 8A. The first picker sub-assembly 250a then moves downwardly with the unit dose packages 18-1, 18-2, 18-3 firmly held by the pickers 252 until the unit dose packages are positioned over the third slot 223 on the nest 214 as shown in FIG. 8C. At that time, the unit dose packages 18 are pneumatically released from the pickers 252 and deposited into the third slot 223 on the nest 214 as shown in FIG. 8C. After release of the unit dose packages 18, the first picker sub-assembly 250a retracts once again for subsequent operations on a following channel 212 on the collation conveyor 202. After the first three unit dose packages 18-1, 18-2, 18-3 are deposited by the first picker sub-assembly 250a into the third slot 223 on the nest 214, the channel 212 advances downstream toward the position identified by line 9A-9A in FIG. 4. The fourth, fifth and sixth unit dose packages 18-4, 18-5, 18-6 in the channel 212 are guided in the associated grooves 232-4, 232-5, 232-6 by the respective ribs in the angled section 240 of the collation table 216 so that they are positioned adjacent to the near lateral side 208 of the table as shown in FIGS. 4 and 9A. The collation conveyor 202 then pauses while the second picker sub-assembly 250b moves into position to retrieve the fourth, fifth and sixth unit dose packages 18-4, 18-5, 18-6 for transfer from the channel 212 on the collation table 216 to the associated nest 214 as shown in FIGS. 9A-9B. As shown in FIG. 9C, the fourth, fifth and sixth unit dose packages 18-4, 18-5, 18-6 are deposited in the first slot 221 on the nest 214 and released by the second picker sub-assembly 250b. A photograph of the unit dose packages 18 in the first and third slots 221, 223 on the nest 214 is shown in FIG. 9D.

Figure 10A:
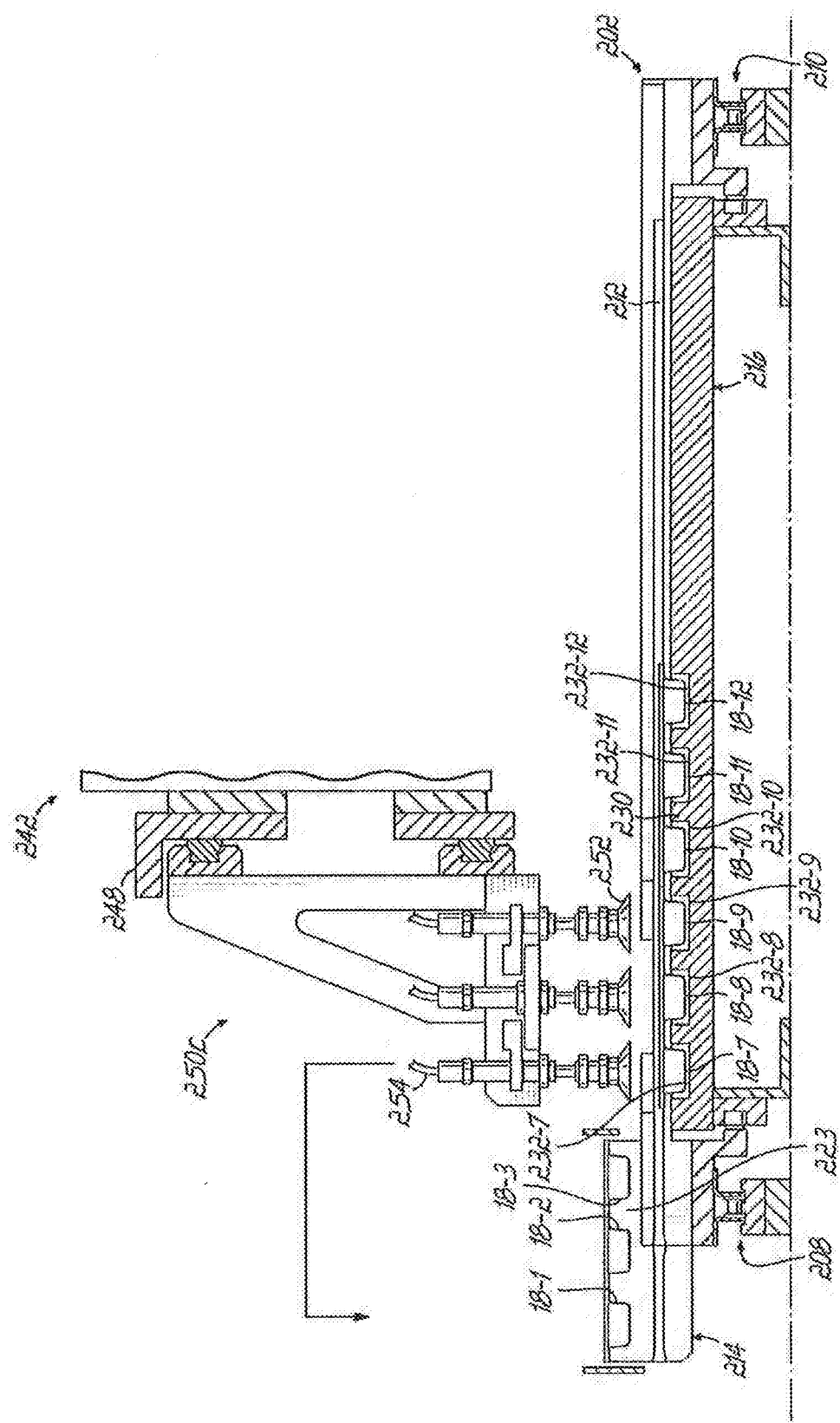
FIGS. 10A-10C are cross-sectional sequential views taken line 10A-10A of FIG. 4 showing a third portion of the picker system transferring a number of unit dose packages from the collation table to the unit dose package nest.
Figure 10B:
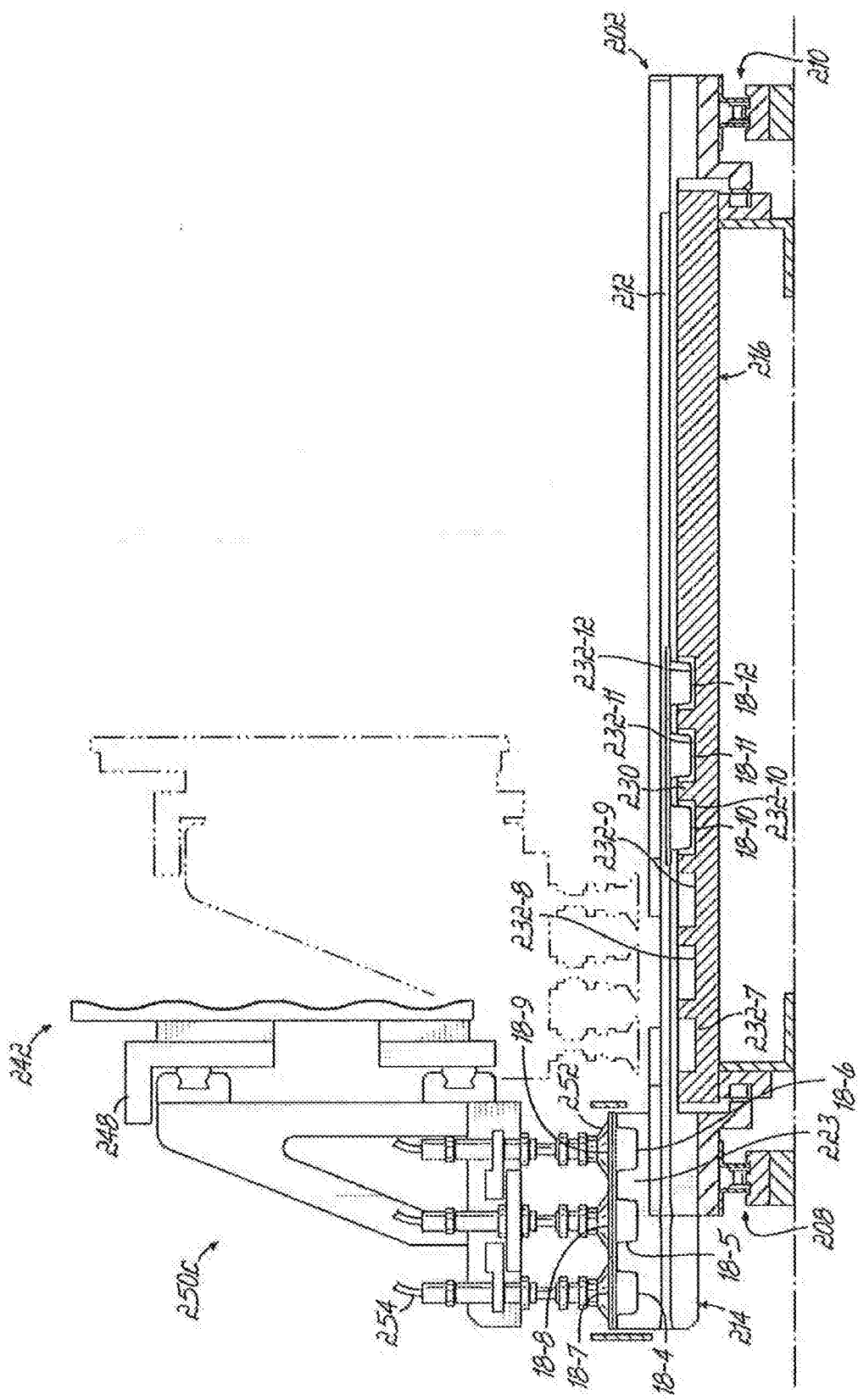
Figure 10C:
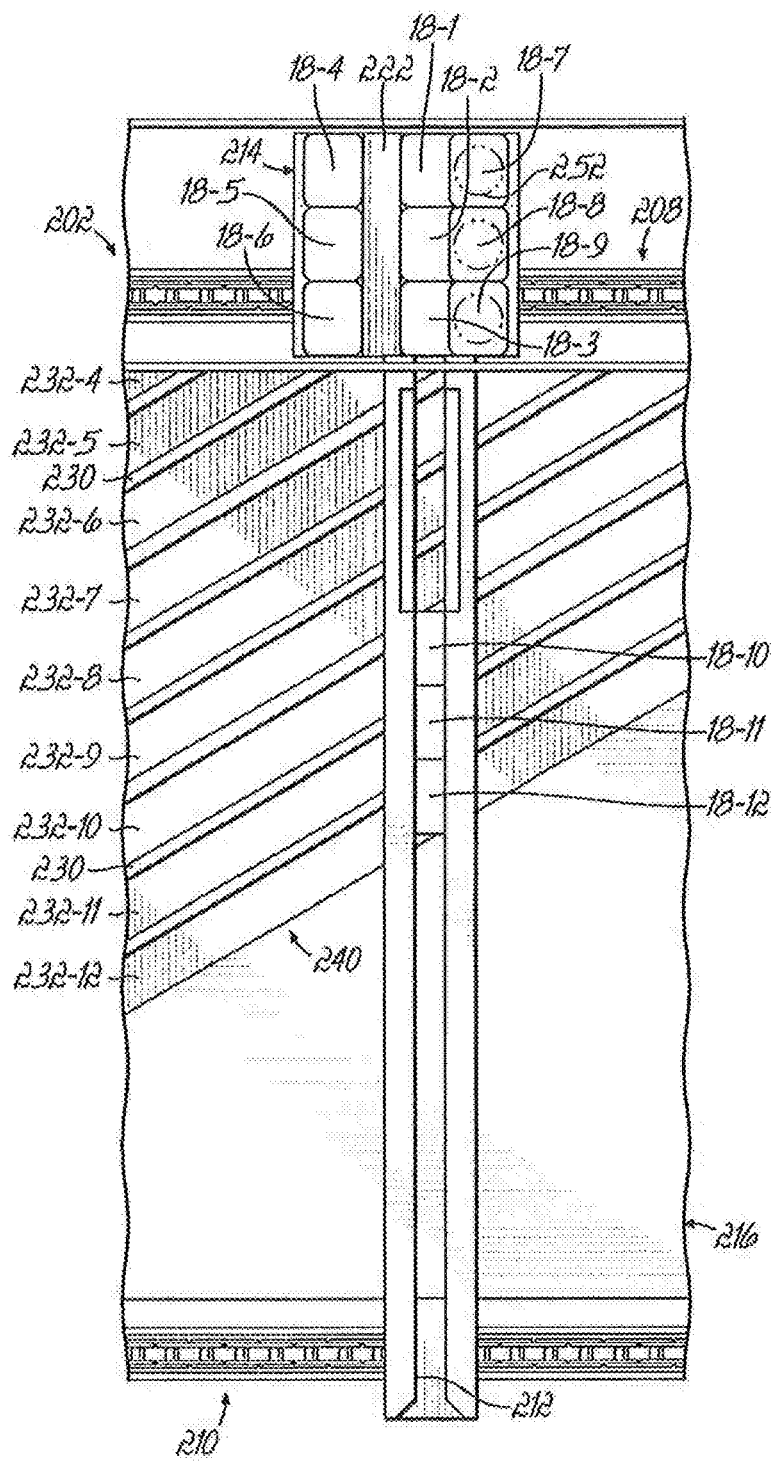

After the fourth, fifth and sixth unit dose packages 18-4, 18-5, 18-6 are deposited into the nest 214, the channel 212 on the collation conveyor 202 indexes or advances downstream until it is aligned with line 10A-10A of FIG. 4. Once again, as the channel 212 advances downstream, the remaining unit dose packages 18 in the channel 212 are guided by the angled section 240 of the associated ribs 230 on the collation table 216 so that they are shifted toward the near lateral side 208 of the collation table. The seventh, eighth and ninth unit dose packages 18-7, 18-8, 18-9 are then positioned adjacent the near lateral side 208 as shown in FIG. 10A so that the third picker sub-assembly 250c may extract them from the channel 212 on the collation table 216 and deposit them into the fourth slot 224 on the nest 214 as shown in FIGS. 10A-10C. The unit dose packages 18-7, 18-8, 18-9 are positioned on the nest 214 so that the adjacent edges of the panel 24 of the unit dose packages overlap the panels 24 of the unit dose packages 18-1, 18-2, 18-3 in the third slot 223 on the nest 214 as shown in FIG. 10C thereby creating a shingled or overlapping arrangement between the unit dose packages 18 of the third and fourth slots 223, 224 in the nest 214.

Figure 11A:
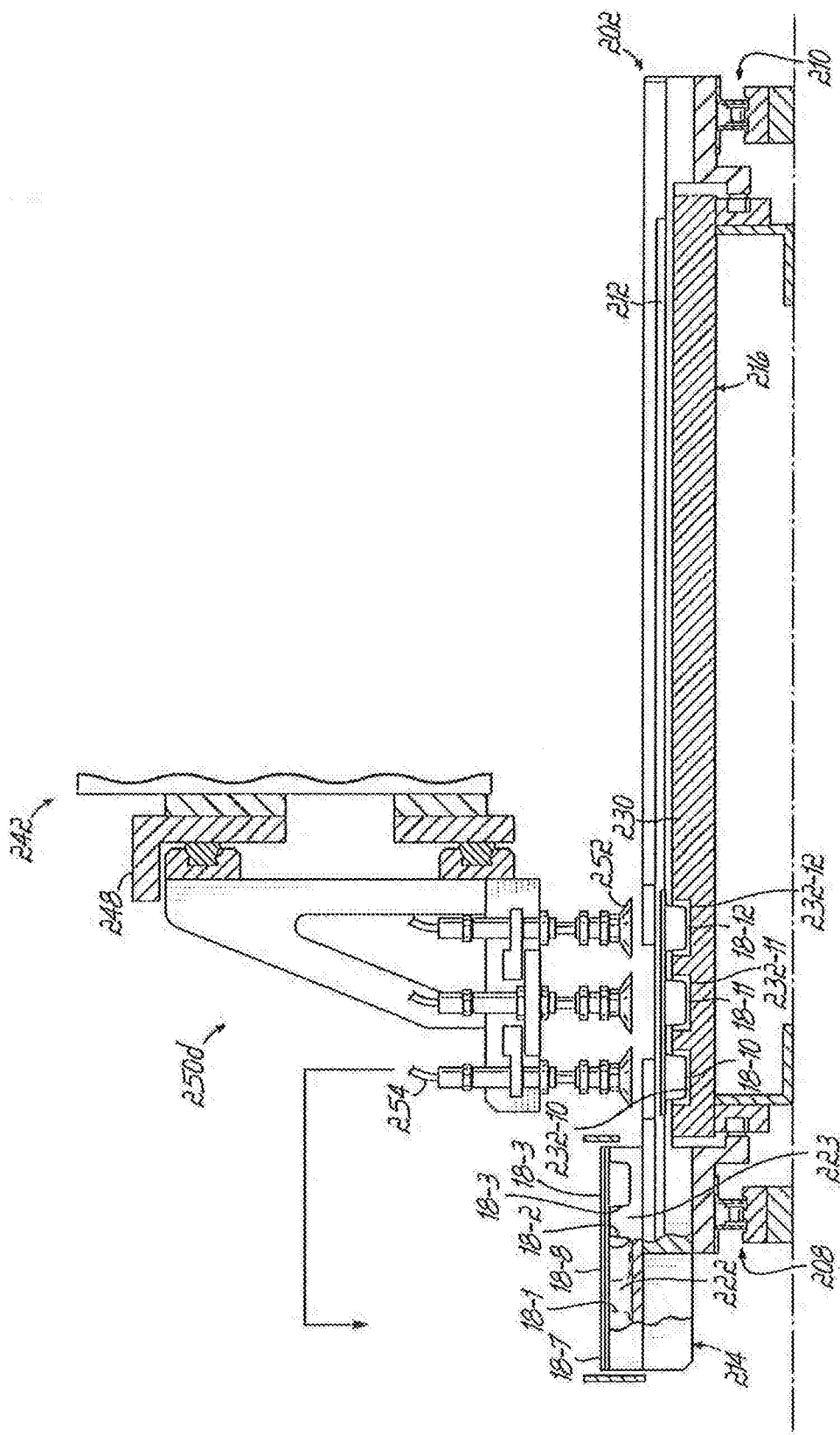
FIGS. 11A-11C are cross-sectional sequential views taken along line 11A-11A of FIG. 4 showing a fourth portion of the picker system transferring a final set of unit dose packages from the collation table to the unit dose package nest.
Figure 11B:
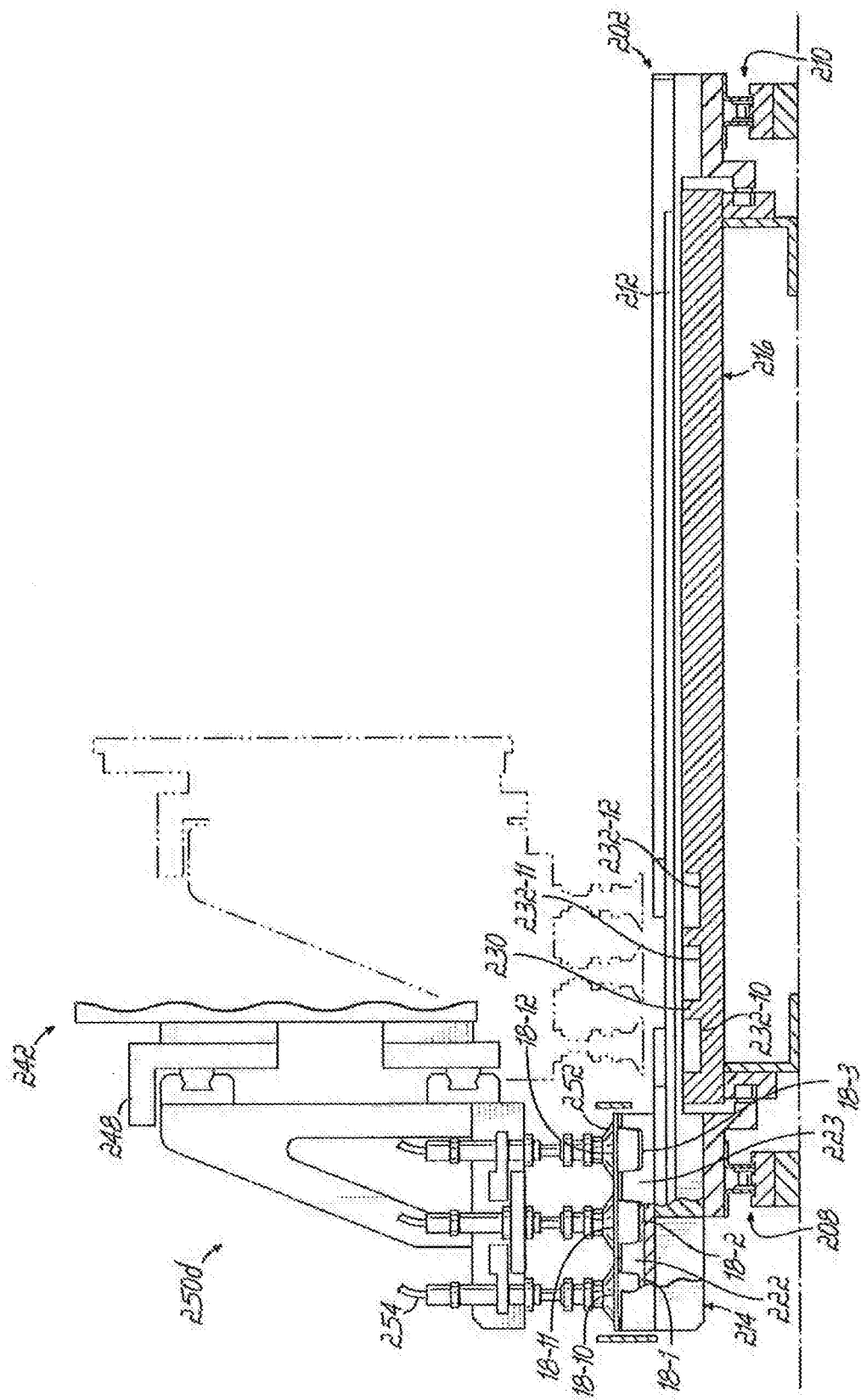
Figure 11C:
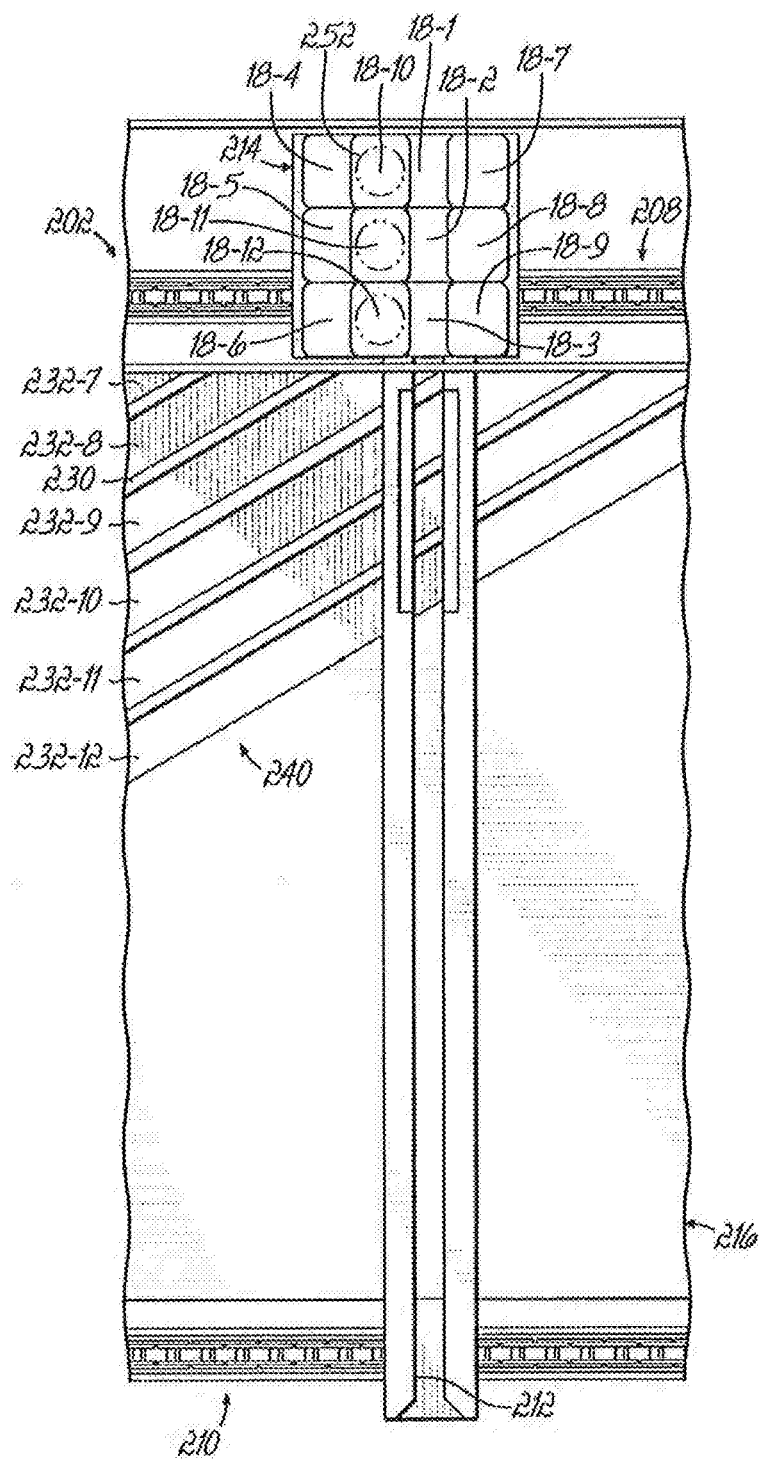

After the seventh, eighth and ninth unit dose packages 18-7, 18-8, 18-9 are deposited onto the nest 214, the channel 212 and collation conveyor 202 advance downstream to be in alignment with line 11A-11A in FIG. 4. The advancement of the channel 212 in this regard likewise shifts the tenth, eleventh and twelfth unit dose packages 18-10, 18-11, 18-12 in the channel 212 toward the near lateral side 208 of the collation table 216 due to the angled orientation of the associated ribs 230 and groove 232 on the collation table 216. As such, the tenth, eleventh and twelfth unit dose packages 18-10, 18-11, 18-12 are positioned as shown in FIG. 11A for retrieval and transfer to the nest 214 by the fourth picker sub-assembly 250d as depicted in FIGS. 11A-11C. The tenth, eleventh and twelfth unit dose packages 18-10, 18-11, 18-12 are deposited by the fourth picker sub-assembly 250d into the second slot 222 on the nest 214 and overlapping on top of the adjacent edges of the panels 24 of the unit dose packages 18 in the first and third slots 221, 223 of the nest 214 as shown in FIG. 11C.

Having described the structure and operation of the accumulation module 200 and the transfer and handling of the unit dose packages 18 from the carrier 30 on the main conveyor 28 to the nest 214 on the collation conveyor 202, one of ordinary skill in the art will appreciate that the description has included twelve unit dose packages 18 in each channel 212; however, any number less than twelve may be present in the channel 212 and, if so, then that number of unit dose packages 18 would be placed in the nest 214 with vacancies in the positions of the non-existent unit dose packages as shown in the nest arrangement of FIG. 11C. Likewise, the description provided herein above follows a single channel 212 in the handling of the associated unit dose packages 18 through the various picker sub-assembly 250a-d operations. It will be appreciated by one of ordinary skill in the art that as the unit dose packages 18 of one channel 212 are being transferred by one of the picker sub-assemblies 250a-d, the other picker sub-assemblies are likewise transferring the associated unit dose packages 18 from other channels 212 onto the nests 214 associated with those channels. In other words, as the first sub-assembly 250a is retrieving unit dose packages one, two and three 18-1, 18-2, 18-3 from a first channel, simultaneously the second picker sub-assembly 250b is likewise retrieving and transferring unit dose packages four, five and six 18-4, 18-5, 18-6 from a channel immediately downstream there from. Likewise, the third and fourth picker sub-assemblies 250c, 250d are retrieving and transferring the appropriate unit dose packages 18 from the associated preceding channels 212 on the collation table 216.

The unit dose package module 300 is seen in FIGS. 1, 2, 2A, 3, 4 and 12. The unit dose package module 300 retrieves the array of unit dose packages 18 from the nest 214 on the collation module 200 and inserts it into a med pass bag 402. As shown particularly in FIG. 12, the collation module 200 includes an offload assembly 256 which controls and offloads the array of unit dose packages 18 from the nest 214 for transfer to the unit dose module 300. The offload assembly 256 includes a laterally extending mounting bar 258 positioned above the collation conveyor 202 proximate a downstream end of the collation module. The mounting bar 258 is supported by a framework 260 of members positioned above the collation conveyor 202 at the downstream end as shown in FIG. 3. The offload assembly 256 is mounted to the mounting bar 258 for translation in a lateral direction toward and away from the unit dose package insert module 300. Mounted on three posts extending downwardly from the offload assembly 256 is an offload comb assembly 262 which includes a rearwardly extending flange 264 to which the offload comb assembly 262 is mounted to the posts on the offload assembly 256. The offload assembly 256 includes four laterally extending and spaced comb members 266 oriented parallel to one another and extending toward the unit dose package insert module 300. A series of four downwardly extending tabs 268-1, 268-2, 268-3, 268-4 are mounted perpendicular to the comb members 266 proximate a root portion of the comb members 266 as shown particularly in FIGS. 12, 12B and 14A. Each of the comb members 266 is aligned with and superimposed above one of the slots 221, 222, 223, 224 of the collation module nest 214. Likewise, each of the tabs 268-1, 268-2, 268-3, 268-4 is aligned with one of the slots of the nest 214 and, as can be seen from FIG. 12, the tab 268-3 aligned with the third slot 223 of the nest 214 is longer than the remaining tabs 268-1, 268-2, 268-4 because the third slot 223 of the nest 214 is deeper or bottomless compared to the remaining slots of the nest 214. The extended length of this tab 268-3 is intended to insure that all of the unit dose packages 18-3 seated in the third slot 223 are offloaded from the nest 214.

The offload assembly 256 operates to push the array of unit dose packages 18 off of the nest 214 and toward the unit dose insert module 300 as shown in FIGS. 12A-14C. Referring to FIGS. 12B and 13B in particular, the comb members 266 are lowered and advanced toward the nest 214 in the direction of arrow E as shown in FIG. 13B. Continued movement of the comb members 266 in this manner places the tabs 268-1, 268-2, 268-3, 268-4 against the array of unit dose packages 18 and the tabs 268 are positioned within the slots on the nest 214. The comb members 266 are positioned atop the four rows of unit dose packages 18 in the array to thereby stabilize and secure them during the offload process from the collation module 200. As such, upon appropriate command and at the appropriate time, the comb assembly 262 advances laterally from the collation module 200 and the tabs 268-1, 268-2, 268-3, 268-4 push the unit dose packages 18 in unison off of the nest 214 while the comb members 266 stabilize and secure them during the offload process. Simultaneously with this operation, one of two insert assemblies 302 on the unit dose package insert module 300 advances toward the nest 214.

Figure 12:
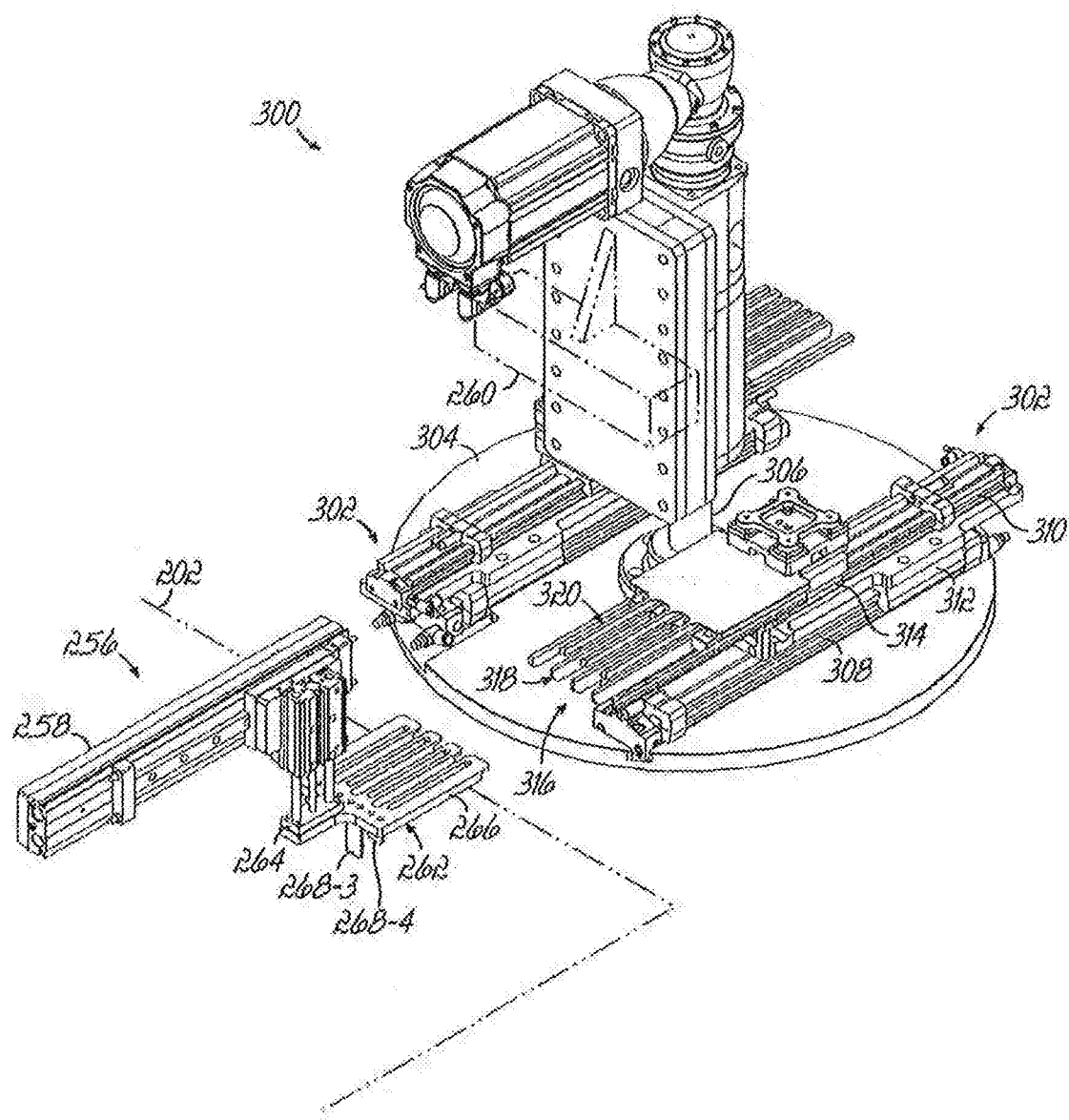
FIG. 12 is a perspective view of a unit dose package insert module positioned to retrieve an array of unit dose packages in the unit dose package nest.
Figure 13A:
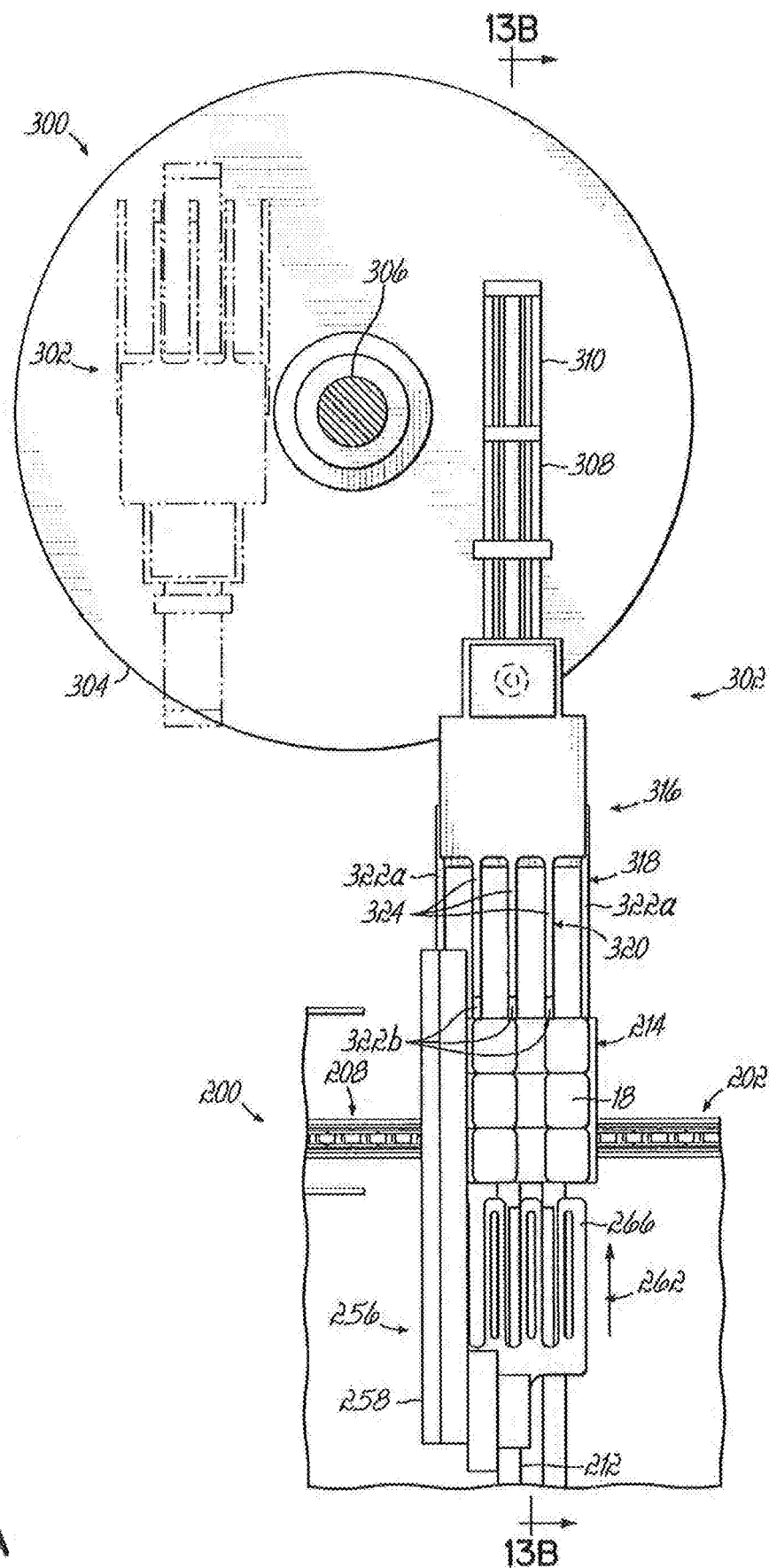
FIGS. 13A and 14A are sequential views similar to FIG. 12A showing fingers on a unit dose package insert assembly retrieving the array of unit dose packages from the unit dose package nest.
Figure 13B:
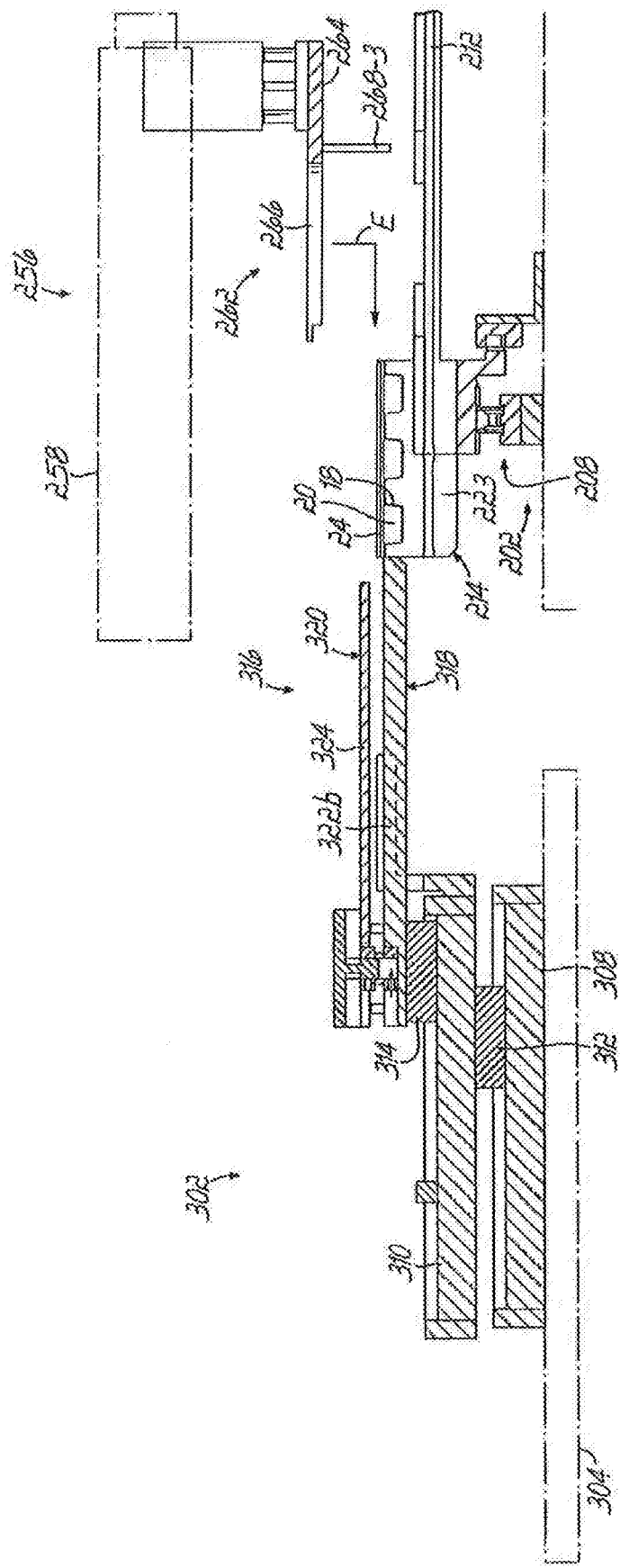
FIGS. 13B and 14B are each cross-sectional views taken along lines 13B-13B and 14B-14B, respectively, of FIGS. 13A and 14A.

The unit dose package insert module 300 as shown particularly in FIG. 12 includes a generally circular turntable 304 mounted for rotation about a central post 306 extending upwardly between a pair of similarly configured, but oppositely oriented insert assemblies 302. Since these two assemblies 302 are identical with one another, only one of them will be described herein and it will be understood that the description is applicable to each of these assemblies 302. Each insert assembly 302 includes a lower mounting block 308 mounted atop the turntable 304 and an upper mounting block 310 mounted on the lower mounting block 308. Each of the mounting blocks 308, 310 includes a pedestal 312, 314 mounted on top of the respective mounting block. The pedestal 312 on the lower mounting block 308 is connected to a lower surface of the upper mounting block 310 and the pedestal 314 on the upper mounting block 310 is connected to a finger arrangement 316. The finger arrangement 316 includes a lower and an upper finger assembly 318, 320, each of which has a number of spaced fingers 322a, 322b, 324 projecting there from and toward the collation module 200 or the med pass bag formation module 400 depending upon the orientation of the insert assembly 302. The upper finger assembly 320 is movable vertically relative to the lower finger assembly 318 to thereby clamp the array of unit dose packages 18 between the respective finger assemblies for secure offloading, manipulation and insertion into the med pass bag 402 as will be described.

The lower finger assembly 318 includes five spaced and generally parallel fingers 322a, 322b which are each designed to be inserted between rows of the blister or base portion 20 of the unit dose packages 18 in the array. This arrangement can be seen in FIGS. 13 and 14A in which the five lower fingers 322*a*, 322*b* are inserted beneath the upper closure panels 24 of the unit dose packages 18 in the array and the outer two fingers 322*a* on the lower finger assembly 318 are positioned on the outboard edges of the first and fourth rows of unit dose packages 18 and the inner three fingers 322*b* are positioned between the adjacent packages 18 in the array as will be appreciated from FIG. 13A.

Figure 14A:
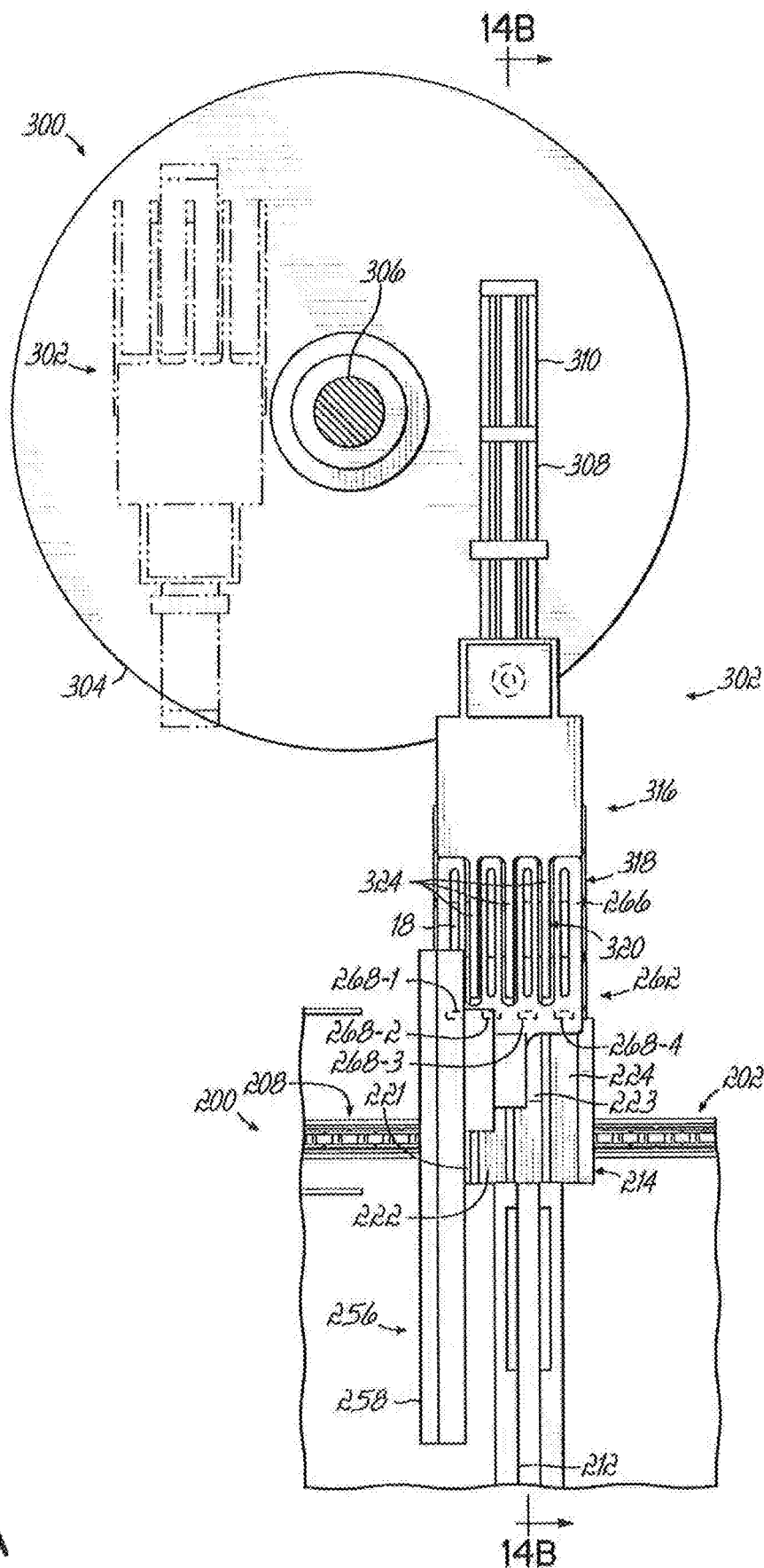
Figure 14B:
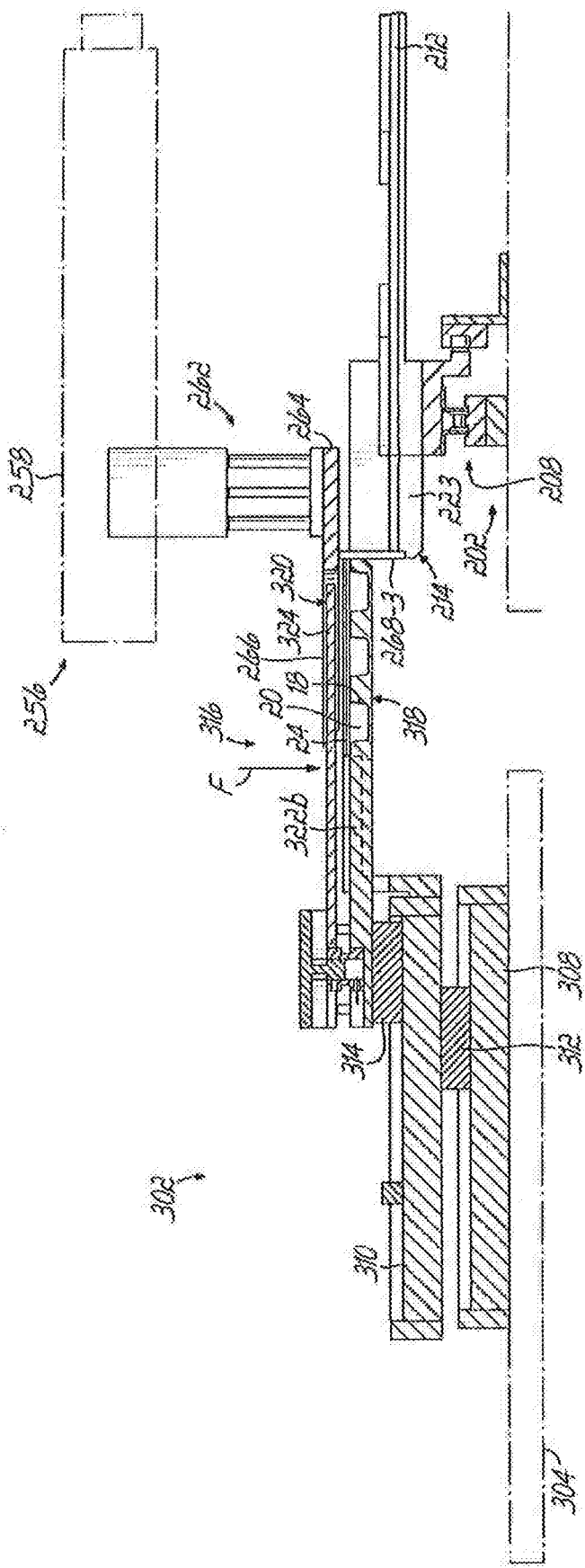
Figure 14C:
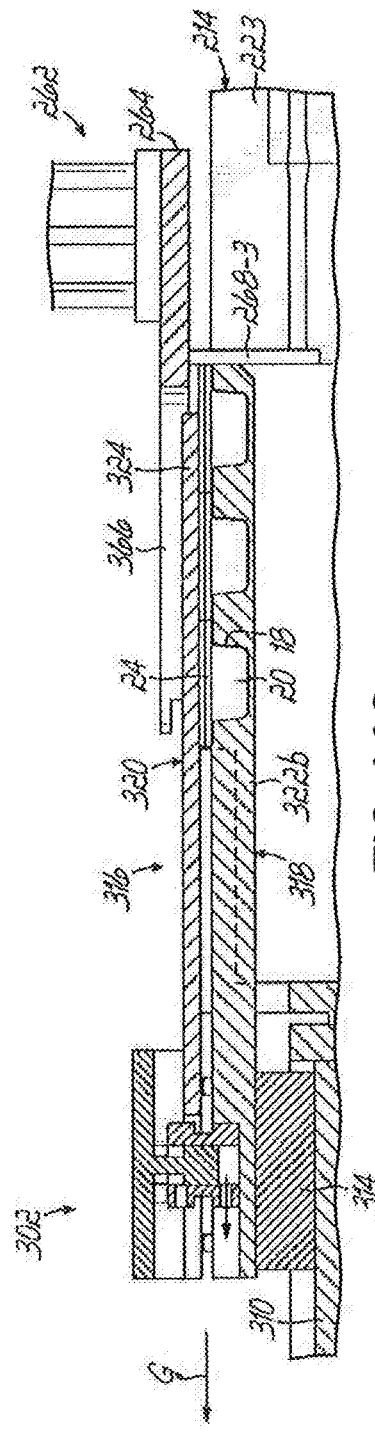
FIG. 14C is a cross-sectional enlarged view of a portion of the unit dose package insert assembly capturing the array of unit dose packages.

The upper finger assembly 320 has three spaced and generally parallel fingers 324 which are aligned with the three interior fingers 322*b* on the lower finger assembly 318 as shown in FIG. 12A. The three fingers 324 on the upper finger assembly 320, when positioned over the array of unit dose packages 18, are superimposed onto the overlapping edges of the panels 24 on the packages 18 in the shingle arrangement of the array as can be seen in FIG. 14A. The three fingers 324 of the upper finger assembly 320, in combination with the fingers 322*a*, 322*b* on the lower finger assembly 318, clamp the unit dose packages 18 there between for secure offloading from the nest 214 and manipulation for insertion into the med pass bag 402. The three fingers 324 in the upper finger assembly 320 are interposed or interleaved between the comb members 266 on the offload assembly 256 as shown in FIG. 14A. As such, during the transfer of the unit dose package array from the nest 214 to the unit dose package insert dial assembly 302, the comb members 266 and the fingers 322*a*, 322*b*, 324 on the upper and lower finger assemblies serve to positively control and move the unit dose packages 18 in the array in an organized and fixed relationship.

The sequential operation of the engagement of the unit dose package array by the upper and lower finger members 322*a*, 322*b*, 324 and the comb members 266 is shown in FIGS. 12A-14C. It is important to note that the upper finger assembly 320 is initially spaced from the lower finger assembly 318 to allow for insertion of the unit dose package array there between as shown generally in FIG. 13B. Once the lower fingers 322*a*, 322*b* are inserted into the array seated on the nest 214, the upper finger assembly 320 pivots downwardly as shown by arrow F in FIG. 14B to thereby clamp the unit dose package array between the upper and lower finger assemblies 318, 320. Subsequently, the comb members 266 are withdrawn from the array and the upper and lower finger assemblies 318, 320 are retracted from the nest 214 as shown by arrow G in FIG. 14C. At this point, the upper mounting block 310 is retracted relative to the lower mounting block 308 with the array of unit dose packages clamped between the upper and lower finger assemblies 318, 320. Once the finger assemblies are retracted, the unit dose package insert module turntable 304 rotates approximately 180° so that the complementary insert assembly 302 is positioned for subsequent retrieval of a succeeding unit dose package array from the collation module 200. Upon the 180° rotation, the unit dose package array which is sandwiched between the upper and lower finger assemblies 318, 320 is in position for insertion into the med pass bag 402 being formed by the bag formation module 400.

Referring to FIGS. 15A-15D, the bag formation module 400 and associated process for forming a med pass bag 402 is shown sequentially in these drawings. The bag formation module 400 is located adjacent to and downstream from the unit dose package module turntable 304 and is adapted to receive the array of unit dose packages held by the upper and lower finger assemblies 318, 320 after the turntable 304 has rotated 180° from the collation module 200 and toward the bag formation module 400. In FIGS. 15A-15D, the array of unit dose packages 18 held by the upper and lower finger assemblies 318, 320 is shown at the far right edge of the drawings. The med pass bag 402 is formed around the array of unit dose packages 18 and the med pass bag 402 includes an upper ply 404 mated with a lower ply 406 forming the back and front faces of the med pass bag 402, respectively.

As previously described, the back face 404 of the med pass bag 402 is a clear plastic layer and is positioned as the upper ply of the med pass bag 402 as processed in the bag formation module 400 as shown in FIGS. 15A-15D. The clear or transparent material of this ply 404 of the med pass bag 402 allows for imaging and tracking of the unit dose packages 18 in the med pass bag 402 at various locations throughout the system. A supply assembly 408 for the upper ply 404 of the med pass bag 402 is shown in the upper regions of FIGS. 15A-15D and includes a supply roll 410 of the upper ply material which is mounted for rotation on a shaft 412. The supply roll 410 is driven by a motor and a sensor is provided to trigger the motor to unwind the supply roll 410 to supply an amount of the upper ply 404 based on input from the sensor. Likewise, a supply roll 414 mounted on an associated shaft 416 is provided for a supply of double-sided tape 418 which passes over an idler roller 420 before passing between a pair of mating rollers 422, 424 at which point the double-sided tape 418 is mated with the back face ply 404 material at the nip between the mating rollers 422, 424. The combined back ply and double-sided tape material passes over a pair of oppositely rotating idler rollers 426, 428 after exiting the mating rollers at which point a take-up roller 430 receives a cover strip 432 pealed from the double-sided tape 418 thereby exposing an adhesive surface of the tape 418 on the upper ply 404 material before the med pass bag 402 is formed. The resulting ply 404 of med pass bag material with the adhered double-sided tape 418 passes over a final idler roller 434 before encountering a suction head 436 which pneumatically applies a suction force to the outer face of the upper ply 404 material to thereby regulate and control the feed and position of the ply into a bag forming assembly 438. An air bar 482 is positioned between the final idler roller 434 and upper suction head 436. The air bar feeds a stream of air to the upper ply 404 material to blow the material inwards in order to add tension and keep the material tight during array loading.

Likewise, a lower suction head 440 is positioned adjacent the bag forming assembly 438 and beneath the array of unit dose packages as shown in FIGS. 15A-15D. The lower suction head 440 operates upon the lower ply 406 of material supplied from a supply roll 442 and which is fed over an idle roller 444 to a print head 446. The supply roll 442 is also driven by a motor and a sensor is provided to trigger the motor to unwind the supply roll 442 to supply an amount of the lower ply 406 based on input from the sensor. As previously described, the material for the front ply 406 of material of the med pass bag 402 is generally opaque and capable of receiving pertinent printed information from the print head 446 as it passes over a print block 448 as shown in FIGS. 15A-15D. After the front ply 406 material exits the print head 446, it passes over an idler roller 450 before being exposed to the lower suction head 440 which regulates, positions and feeds the ply 406 into the med pass bag forming assembly 438.

Figure 15A:
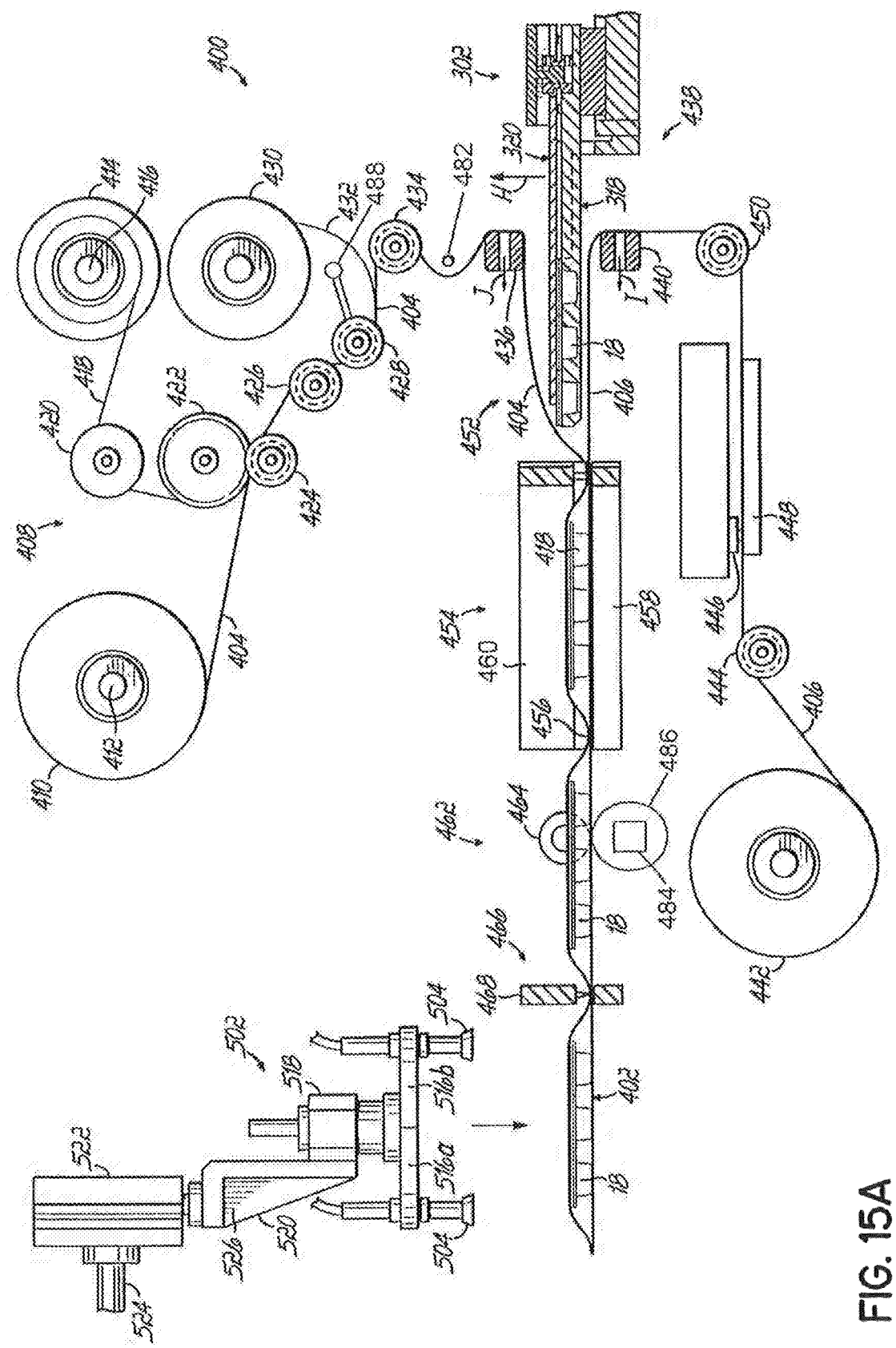
FIGS. 15A-15D are sequential partially cross-sectional views of a medpass bag formation module and unit dose package insert dial assembly according to one embodiment of this invention.

The converging plies 404, 406 of the med pass bag form an entry zone 452 for the upper and lower finger assemblies 318, 320 to horizontally insert the array of unit dose packages 18 held by the finger assemblies. Once the array is positioned in the entry zone 452, the upper finger assembly 320 elevates upwardly in the direction of arrow H as shown in FIG. 15A and the array of unit dose packages 18 is deposited on the lower ply 406 positioned beneath the array while the finger assemblies 318, 320 are retracted back toward the turntable 304 on the unit dose insert module 300.

Figure 15B:
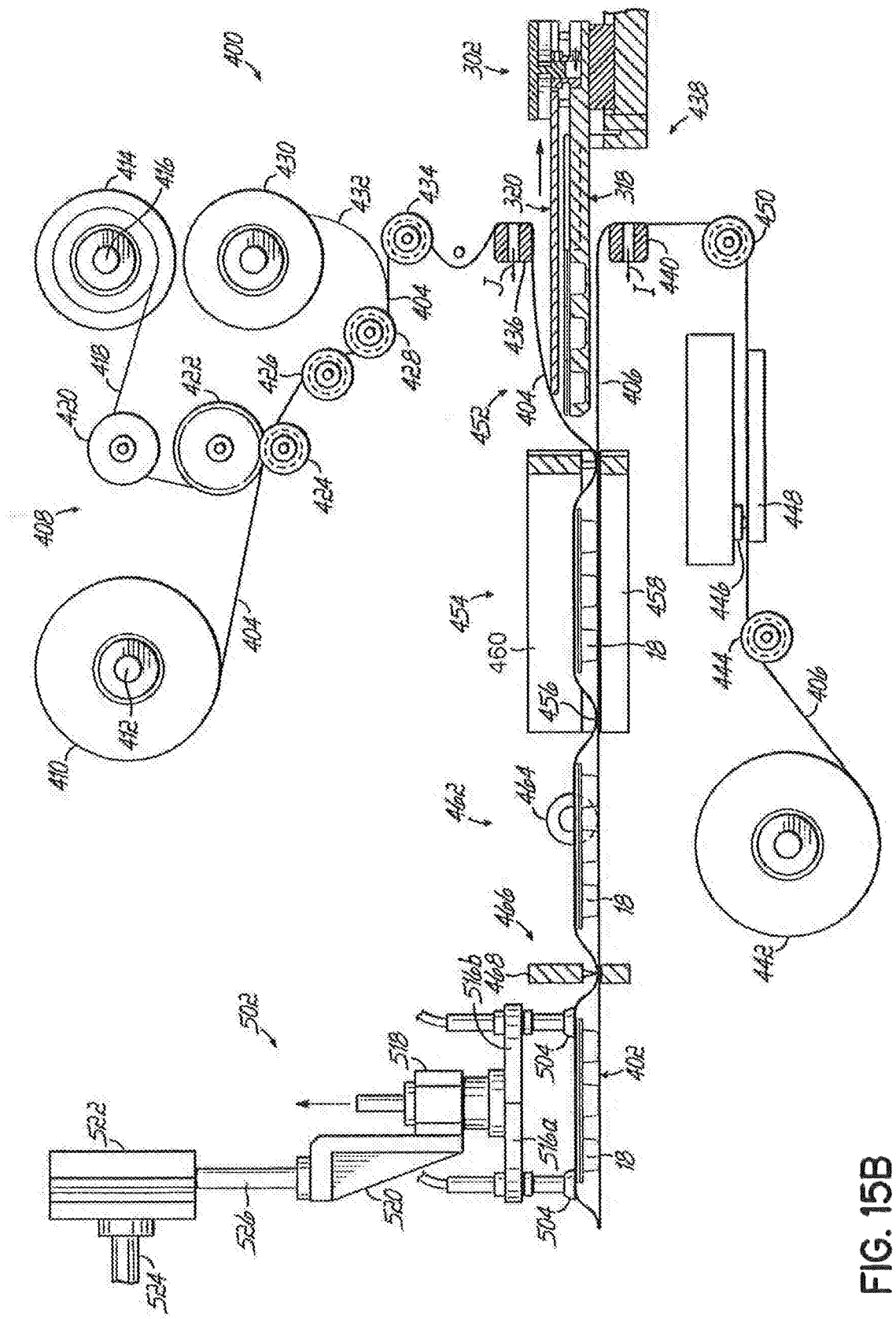

The upper and lower suction heads 436, 440 draw the associated plies 404, 406 of the med pass bag 402 against the adjacent surface of the respective heads as shown by the arrows I and J in FIG. 15B while the upper and lower finger assemblies 318, 320 are retracted to thereby maintain proper positioning of the plies 404, 406 during the insertion and retraction operations. Alternatively, the upper and lower suction heads 436, 440 can be provided as upper and lower closure bars without applying suction to the associated plies 404, 406. The upper and lower closure bars each include a flapper integrated therein to contain the array during indexing of the plies 404, 406. The idler roller 428 is positioned on the end of a weighted dancer arm 488, which pivots about the opposite end to move the idler roller 428 to take up slack in the upper ply 404. Likewise, an idler roller is positioned on the end of another weighted dancer arm, which pivots about the opposite end to move the idler roller to take up slack in the lower ply 406. When the upper and lower closure bars are open for array loading, the combination of the dancer arms and the air bar 482 keep tension on the plies 404, 406 to keep them clear of the array loading mechanism.

Figure 15C:
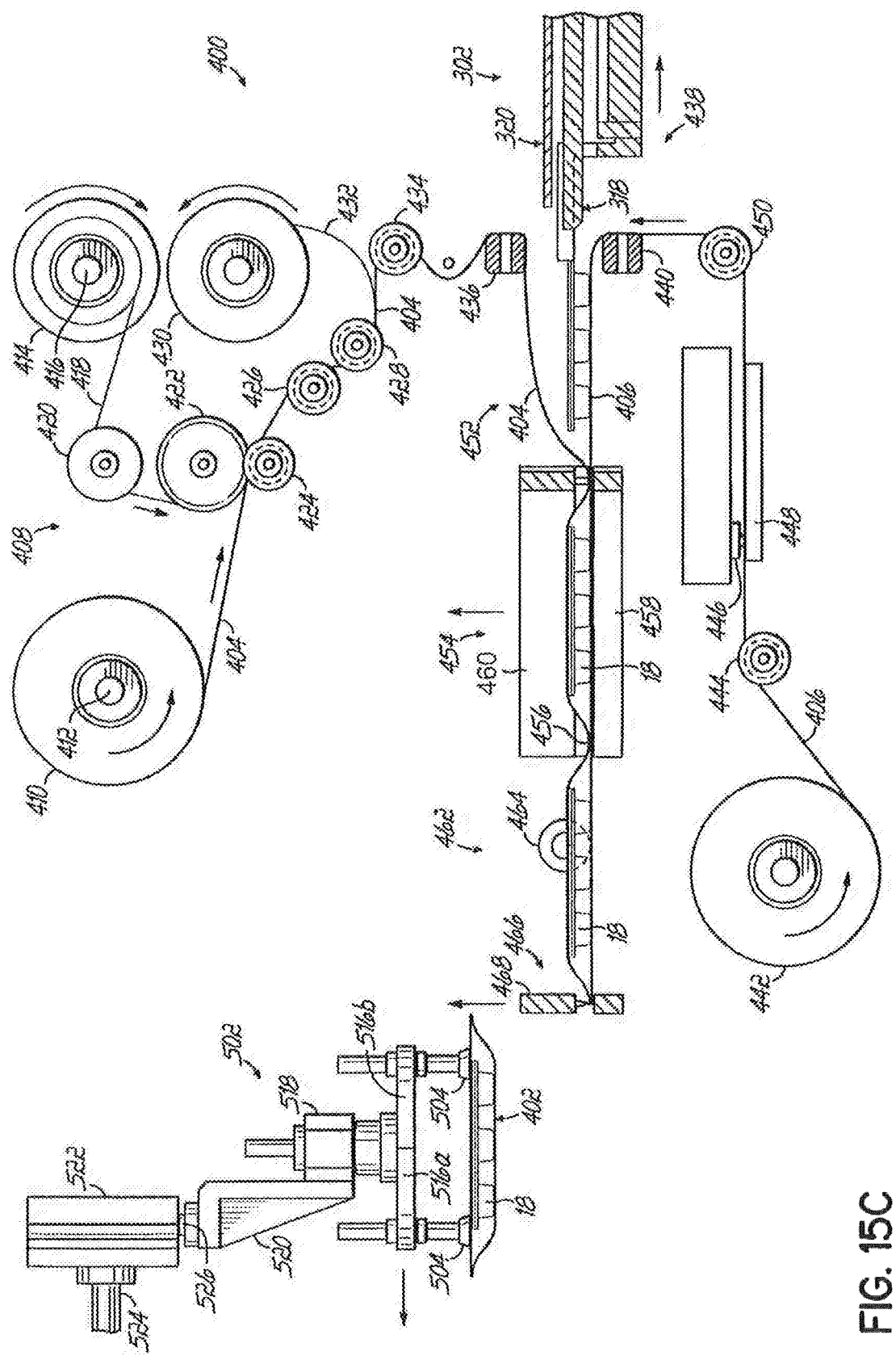
Figure 15D:
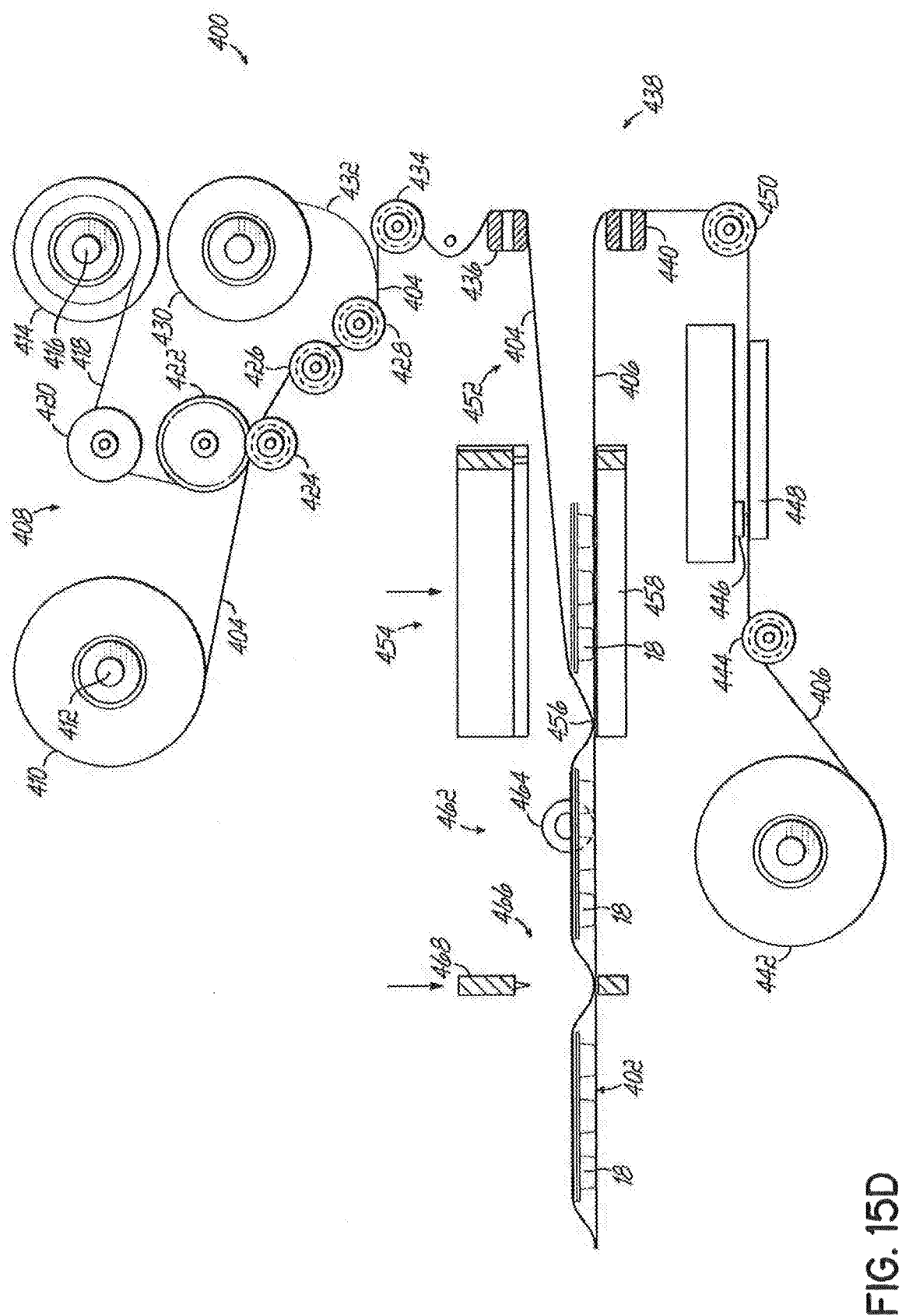

Positioned downstream from the entry zone 452 is a bag forming zone 454 which forms a seam 456 on three edges of the generally rectangular or square med pass bag 402. The three seams 456 are formed on the downstream edge and the two lateral side edges of the bag 402 at the bag forming zone 454. The bag forming zone 454 includes a lower platen 458 and upper die 460 which reciprocate relative to one another to thereby allow for entry of the plies 404, 406 and array of unit dose packages 18 when separated from one another as shown in FIG. 15D and sealed along the three sides of the plies 404, 406 and around the array when mated together as shown in FIGS. 15A-15C.

The fourth edge of the med pass bag 402 is sealed by the downstream edge of the platen 458 and die 460 when the med pass bag 402 is at a perforation zone 462 downstream from the bag forming zone 454. The die can include a rubber seal between the platen 458 and die 460 to provide some variation between the relative positioning of the platen 458 and die 460 during sealing. Alternatively, a spring washer or washers can be positioned between the platen 458 and die 460 to allow for the relative positioning of the platen 458 and die 460 during sealing. The perforation zone 462 includes one or more rotating perforation wheels 464 according to various embodiments of this invention to thereby form tear open perforation lines along the eventual bottom edge and the top edge adjacent the double-sided tape 418 in the med pass bag 402. Only one perforation wheel 464 is shown in FIGS. 15A-15D, but it will be appreciated that other wheels may be provided in the perforation zone 464.

Instead of the perforation wheel 464, the platen 458 and/or the die 460 can include teeth to tear open perforation lines along the eventual bottom edge and/or the top edge adjacent the double-sided tape 418 in the med pass bag 402. A roller downstream of the platen 458 and die 460, for example in the position of the perforation wheel 464, serves as an idler roller driven by a stepper motor 484 via upper and lower spur gears 486 to pull material through the system. A sensor is provided to give feedback to the stepper motor 484 to determine an amount of drive required.

Immediately downstream from the perforation zone 464 is a cutting zone 466 with a cutter 468 which separates the adjacent medpass bags from one another. Downstream from the cutter 468 is located a picker assembly 502 which is lowered into the position of FIG. 15B to remove the med pass bag 402 formed around the array of unit dose packages 18 and transfer it to the downstream bag accumulation module 500. The picker assembly 502 includes four pneumatically actuated suction heads 504 which selectively adhere to the upper ply 404 of the med pass bag 402 as shown in FIG. 15C.

Figure 16A:
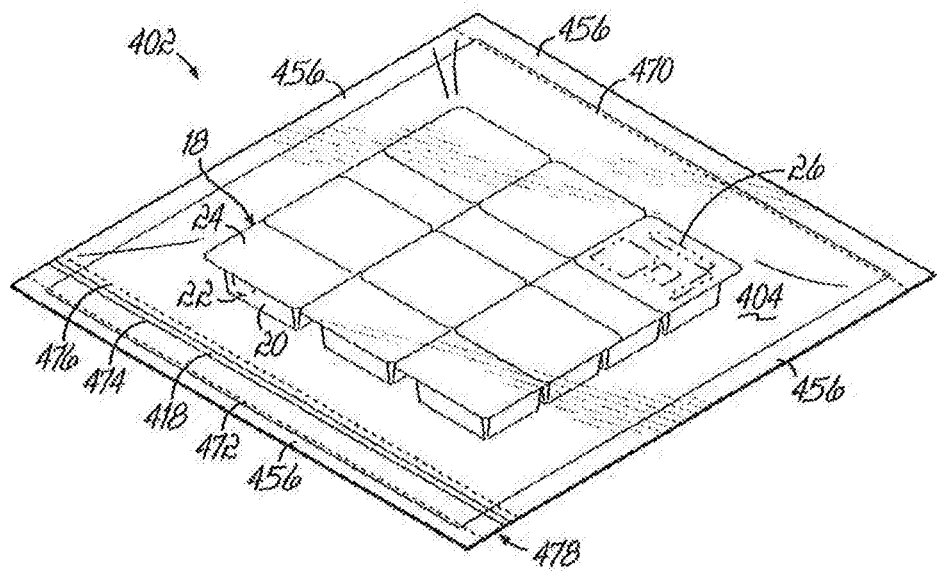
FIG. 16A is a perspective view of one embodiment of a medpass bag according to this invention with an array of unit dose packages contained therein.
Figure 16B:
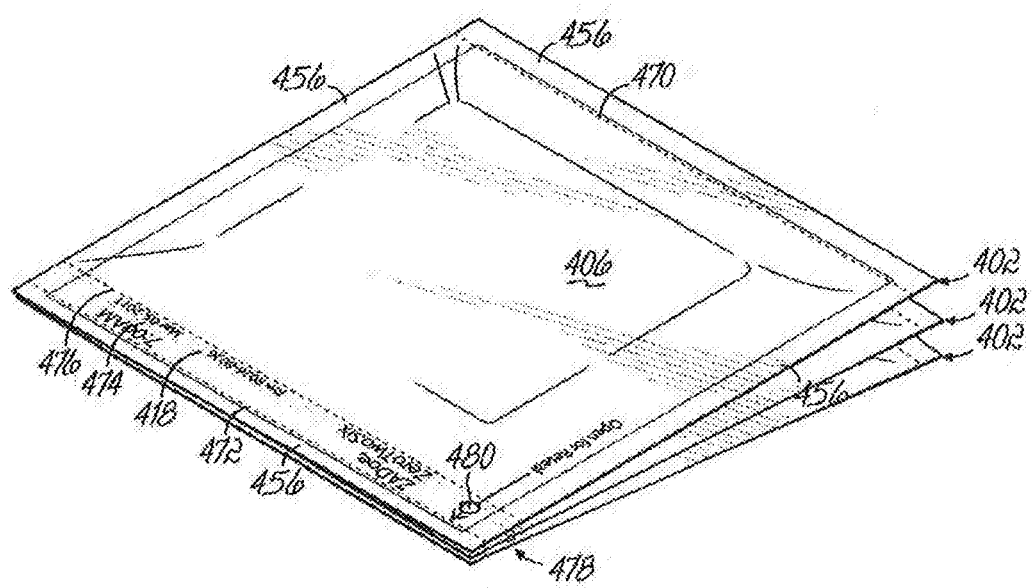
FIG. 16B is a perspective view of multiple medpass bags heat staked together.
Figure 16C:
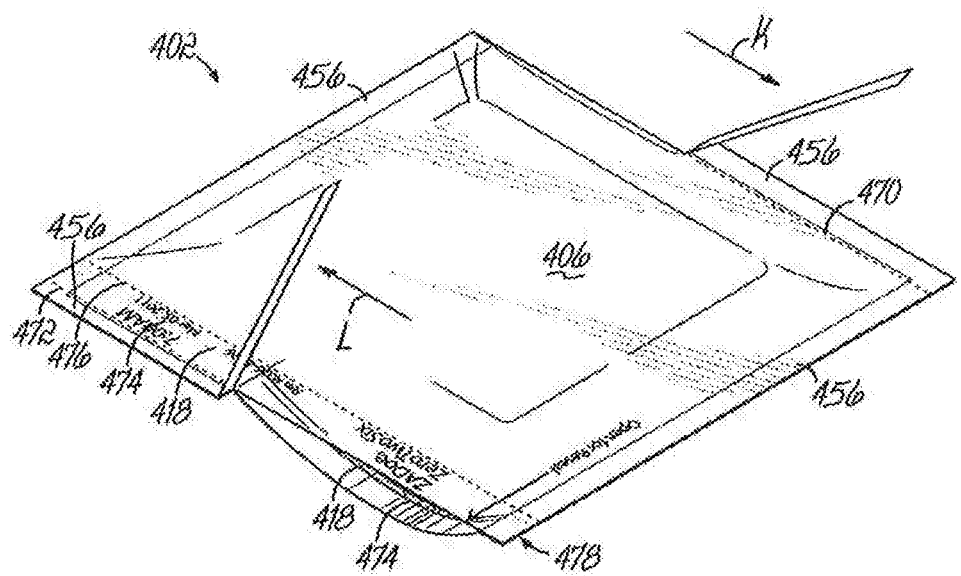
FIGS. 16C and 16D are perspective views showing methods of opening the medpass bag according to various aspects of this invention.
Figure 16D:
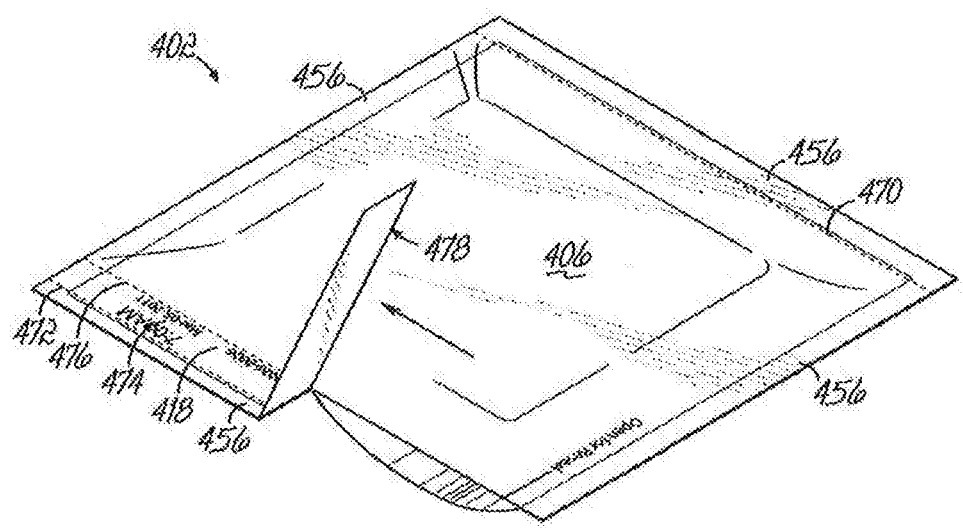

Referring to FIGS. 16A-16D, one embodiment of the med pass bag 402 containing the array of unit dose packages 18 is shown. FIG. 16A is a perspective view of the back face 404 of the bag 402 with the clear ply surface of the bag making the unit dose packages 18 therein visible. FIGS. 16C and 16D are views of the opposite, front face 406 of the med pass bag 402 and show alternatives for opening the bag 402 to retrieve the unit dose packages 18 therein. FIG. 16B is a perspective view of a number of med pass bags 402 shown heat staked together as will be described later herein. Vision inspection of the unit dose package array as it is being enclosed in the med pass bag 402 is included in various embodiments of this invention.

In one embodiment, the med pass bag 402 includes a bottom tear open perforation line 470 along a bottom edge of the bag 402 which allows for retrieval of the entire contents of the med pass bag 402 as shown by arrow K in FIG. 16C. Alternatively, the med pass bag 402 may be opened along a first top perforation line 472 at the top edge of the bag 402 as shown by arrow L in FIG. 16C. This exposes a re-closeable seam 474 at the top edge of the bag 402 which is selectively opened, closed, reopened and reclosed by the double-sided adhesive tape 418 sandwiched between the top and bottom plies 404, 406 of the med pass bag 402. The ability to open and reclose the med pass bag 402 allows for retrieval of some, but not all, of the unit dose packages 18 at various times while still providing an operational and functional med pass bag 402 for the remainder of the contents therein. A second top perforation line 476 is provided adjacent the double-sided tape 418 and opposite from the first top perforation tear line 472. The second top perforation tear line 476 adjacent the double-sided tape allows for complete removal of an upper portion 478 of the bag 402. This offers a number of benefits and advantages, including the opportunity to open the bag 402 and retrieve the contents 18 therein. Likewise, once the contents 18 of the bag 402 are distributed to the patients at the LTC, the upper portion 478 of the bag 402 may be separated from the remainder of the bag 402 and disposed of in a discrete and confidential manner according to HIPAA regulations. The front face 406 of the bag 402 is printed with various information, including the specific medications, the patient's name, the administration time, room number, the facility, the provider and other data. Such information may be printed on the bag 402 as shown in FIG. 16C and outboard of the second top perforation line 476 such that tearing the bag along the second top perforation line 476 removes the sensitive information and this portion 478 of the bag 402 once removed can be shredded or disposed of according to privacy regulations while the remainder of the bag 402 can be disposed of in a standard waste receptacle thereby minimizing the impact of the demands for compliance with HIPAA regulations and privacy and confidentially safeguards. In one embodiment, multiple med pass bags 402 are heat staked together at a location 480 within the portion 478.

Figure 17:
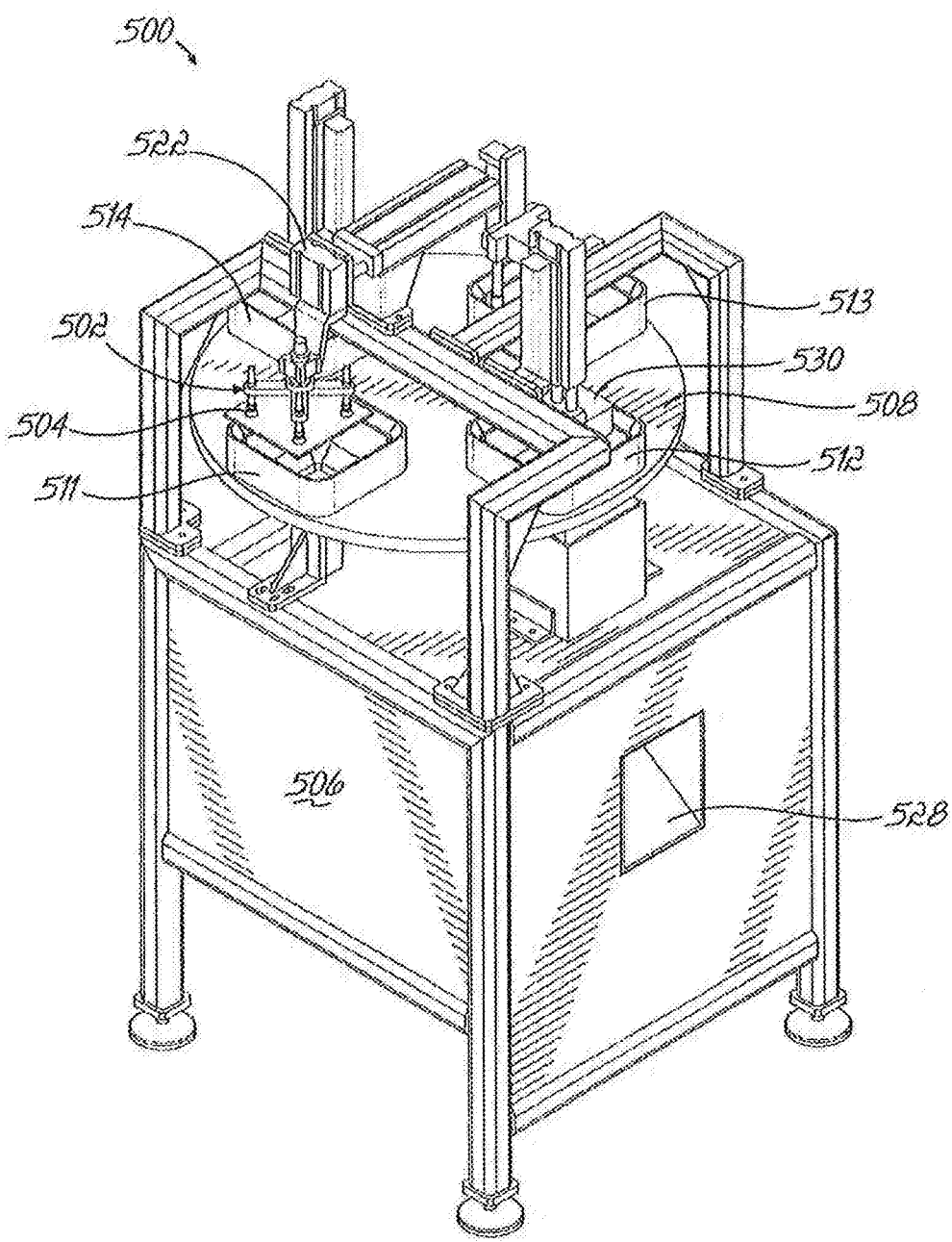
FIG. 17 is a perspective of one embodiment of a bag accumulation module according to this invention.

As shown in FIG. 17, downstream from the bag formation module 400 is the bag accumulation module 500. The bag accumulation module 500 includes a base cabinet 506 upon which is supported an accumulation dial 508 for rotation.

The accumulation dial 508 includes four stations or hoppers 511, 512, 513, 514 positioned approximately 90° relative to one another. The four stations are identified by the three, six, nine and twelve o'clock positions. As shown in FIGS. 17-22, the nine o'clock position includes the picker assembly 502 shown in FIG. 15C which retrieves the med pass bag 402 from the bag formation module 400 and transfers it to the bag accumulation module 500. The picker assembly 502 includes four pneumatically actuated pickers 504 oriented in a cruciform arrangement on two perpendicular mounting arms 516a, 516b. The mounting arms 516a, 516 emanate outwardly from a central rotary hub 518 on the picker assembly 502. The picker assembly hub 518 is coupled to an arm 520 and mounting block 522 which is likewise connected to picker assembly extension bars 524. The extension bars 524 extend outwardly toward the bag formation module 400 to position the pickers 504 over the med pass bag 402 as shown in FIG. 15C. A vertical extension post 526 is coupled between the mounting block 522 and the hub 518 to lower the pickers 504 into contact with the med pass bag 402 at which point the pneumatic pickers 504 engage the bag 402 for transfer in the direction of arrow M in FIG. 15C when the extension bars 524 are retracted and the elevation post 526 is withdrawn into the orientation shown.

Figure 18:
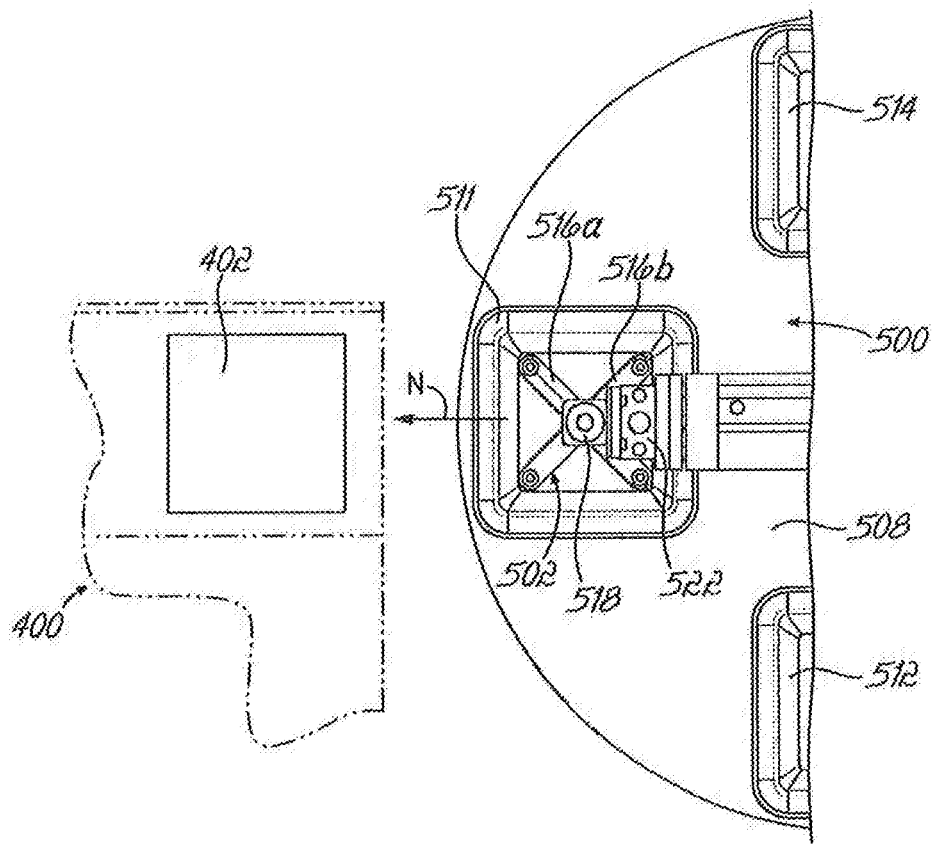
FIGS. 18-21 are sequential top plan views of a portion of the bag accumulation module retrieving medpass bags for processing.
Figure 19:
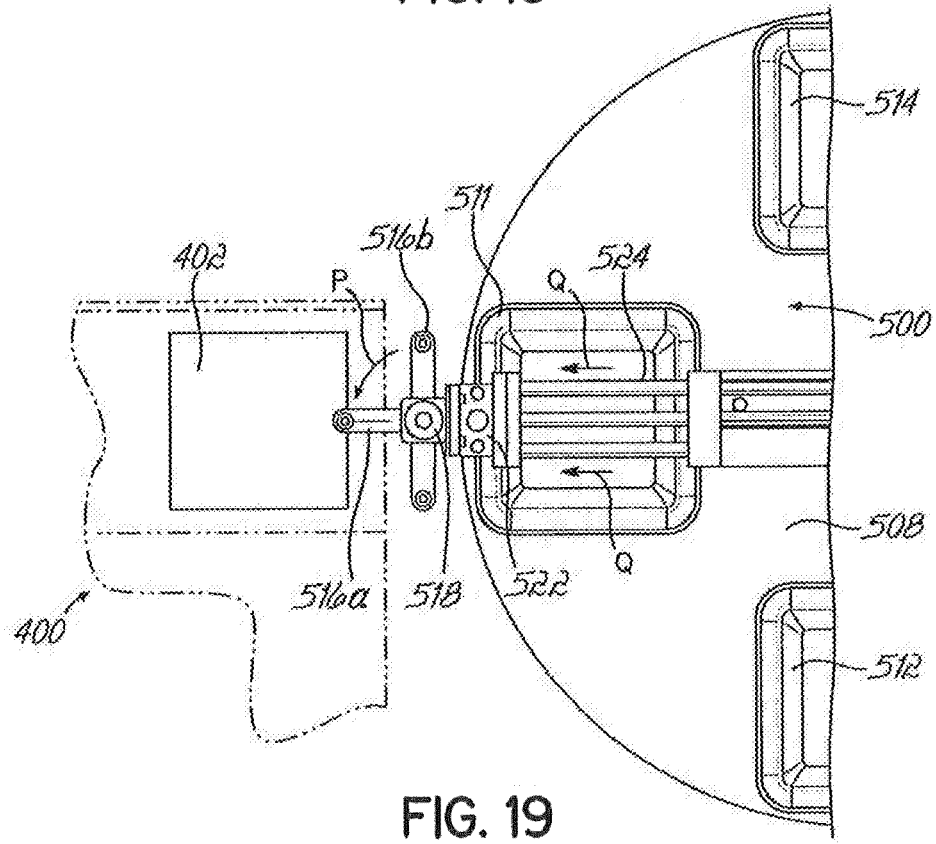
Figure 20:
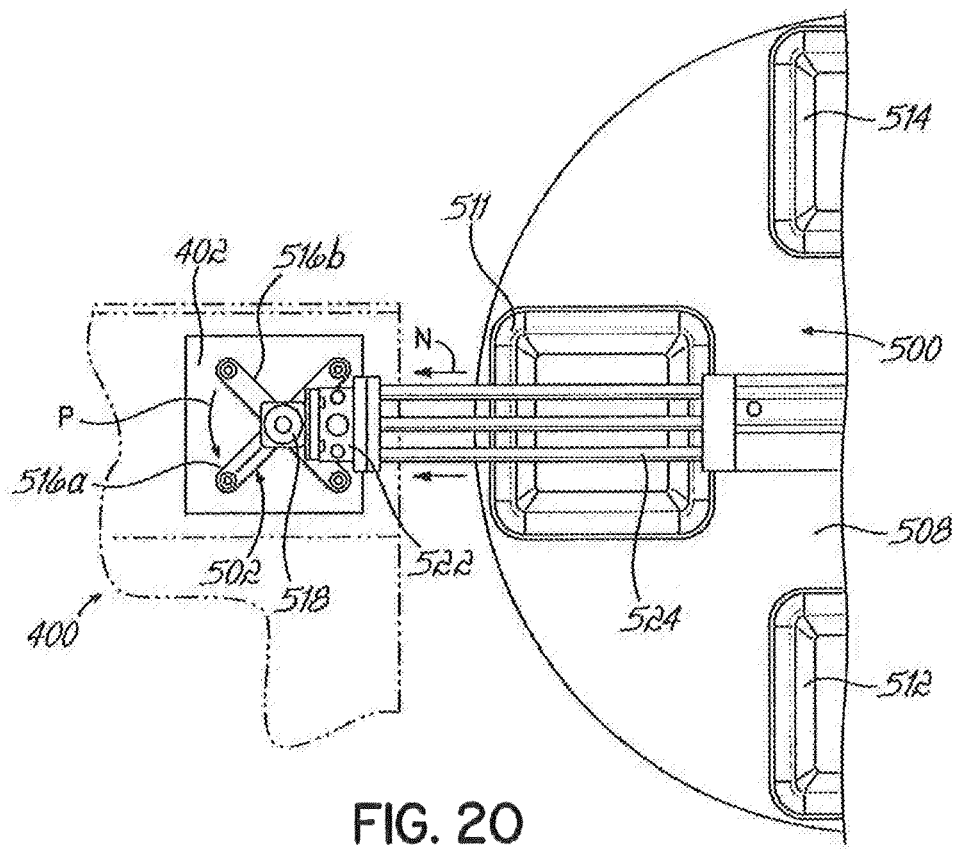
Figure 21:
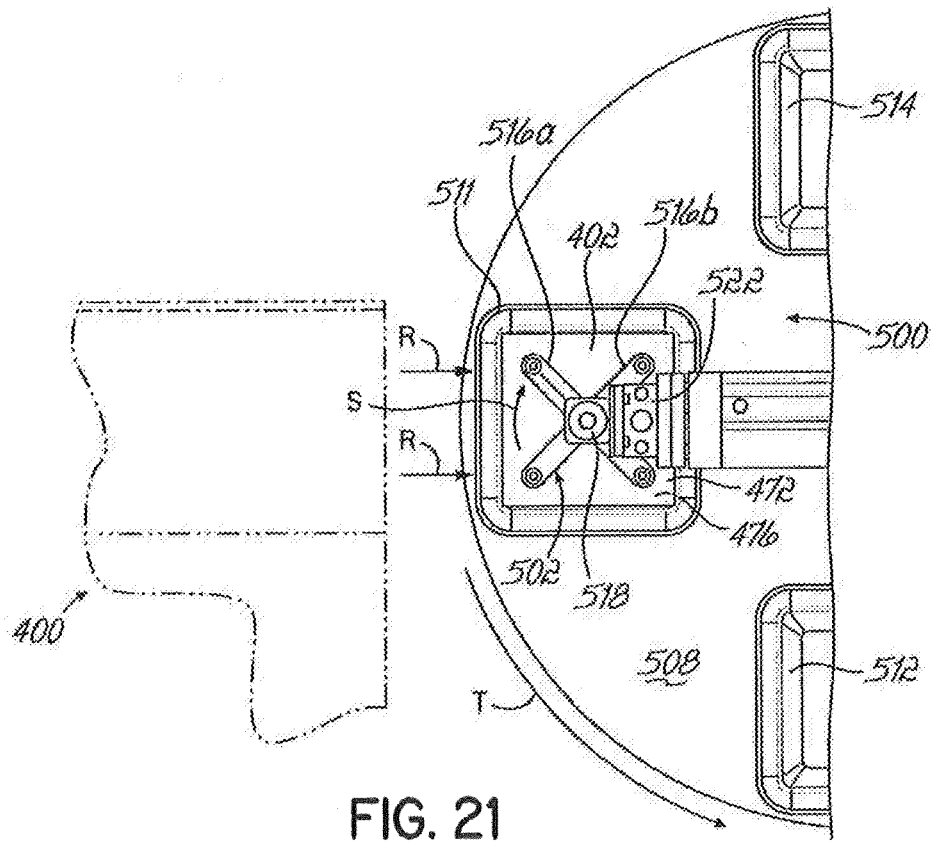
Figure 23:
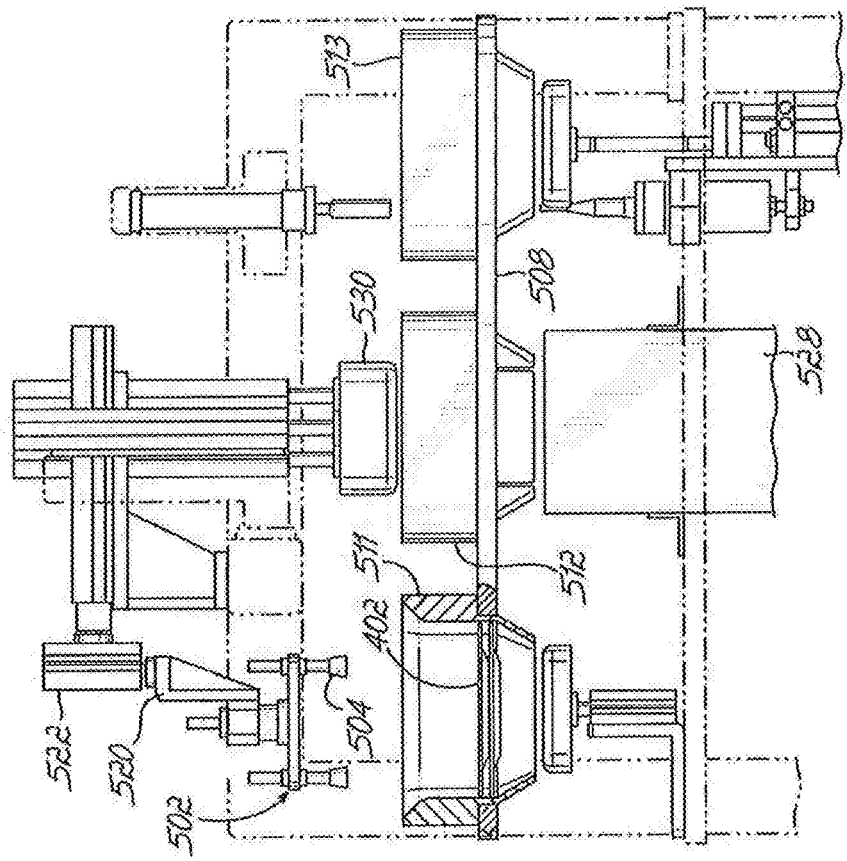
FIGS. 22-23 and 26-28B are side elevational partially cross section sequential views of the module of FIG. 17 processing individual medpass bags together and positioning them within a pre-formed travel pack.

As shown sequentially in FIGS. 18-21, the picker assembly 502 extends in the direction of arrow N in FIG. 18 from its home position on the bag accumulation module 500. Simultaneously, the pickheads 504 are rotated approximately 90° in the direction of arrow P as the extension bars 524 extend as shown by arrows Q in FIG. 19. As shown in FIG. 20, the reoriented pickheads 504 are lowered so that the pickheads 504 come in contact with the med pass bag 402 and through pneumatic actuation engage the med pass bag 402 and the picker assembly 502 returns to the home position on the bag accumulation module 500 as shown by arrows R in FIG. 21. Simultaneously, the picker assembly 502 rotates approximately 90° in the direction of arrow S so as to orient the med pass bag 402 over a collection hopper 511 at the nine o'clock position for repository on the accumulation dial 508. The med pass bag 402 is deposited into the accumulation hopper 511 with the double-sided tape, top edge and top tear-open perforation lines 472, 476 of the med pass bag 402 oriented as shown in FIG. 21. If additional med pass bags 402 are included in this particular order for administration time or patient requirements, subsequent bags 402 are likewise retrieved and deposited into the accumulation hopper similar to the sequence as shown in FIGS. 18 and 20. After all the med pass bags 402 for a particular order, patient, delivery time or other requirements are accumulated in the hopper 511, the accumulation dial 508 rotates approximately 90° as shown by arrow T in FIG. 21.

Figure 22:
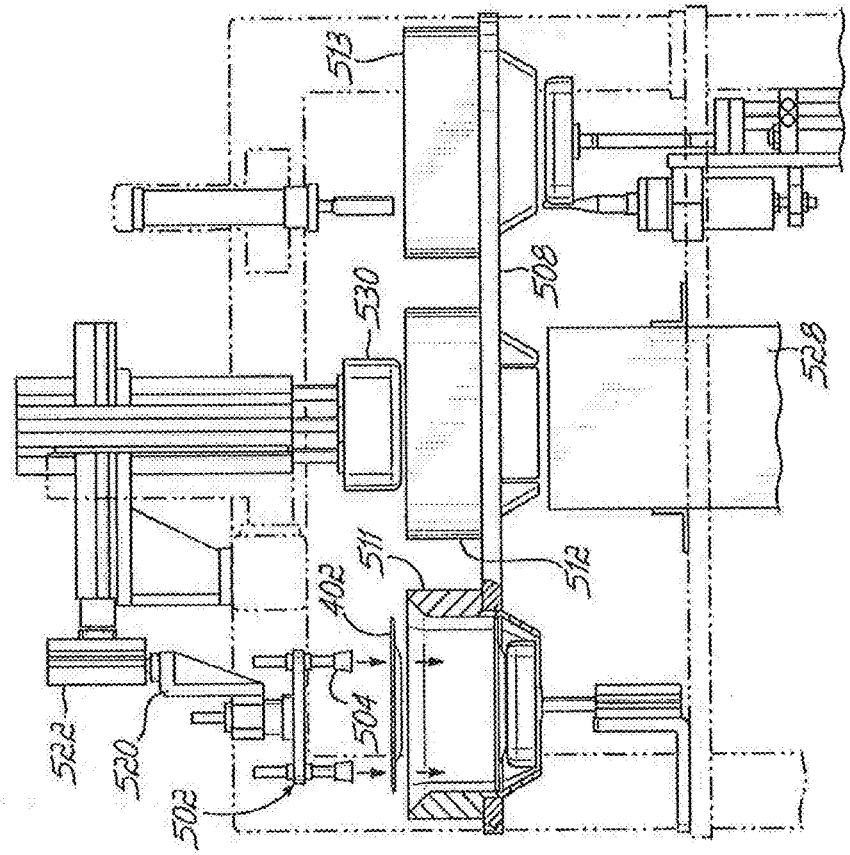
Figure 25:
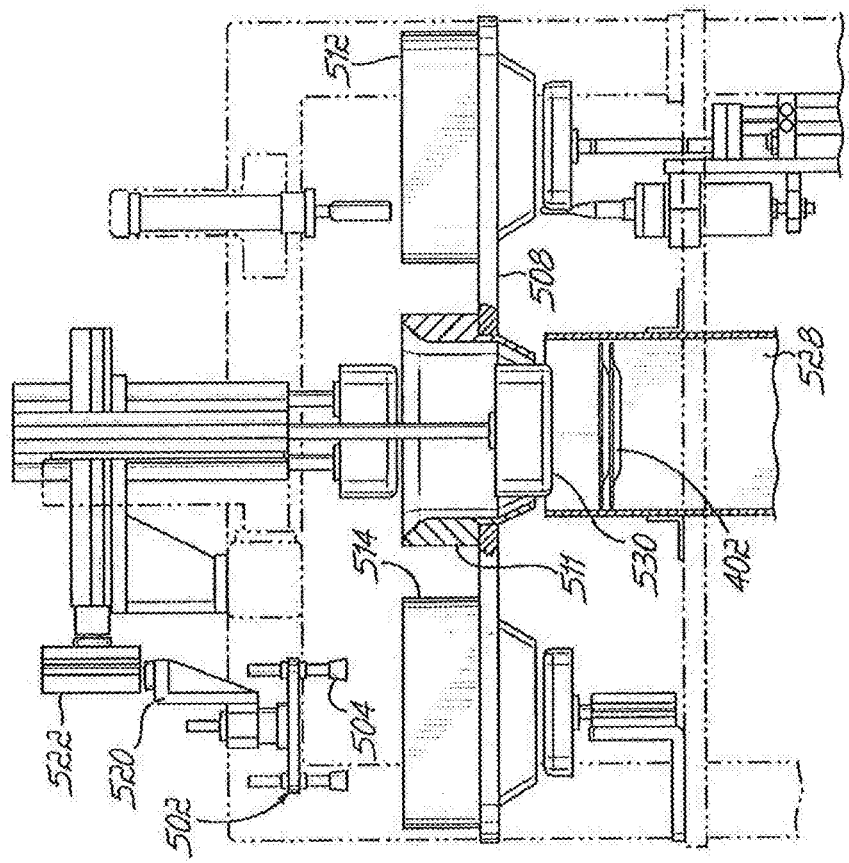
FIGS. 24-25 are views similar to FIG. 23 with selected medpass bags being processed through a rejection chute of the module of FIG. 17.
Figure 24:
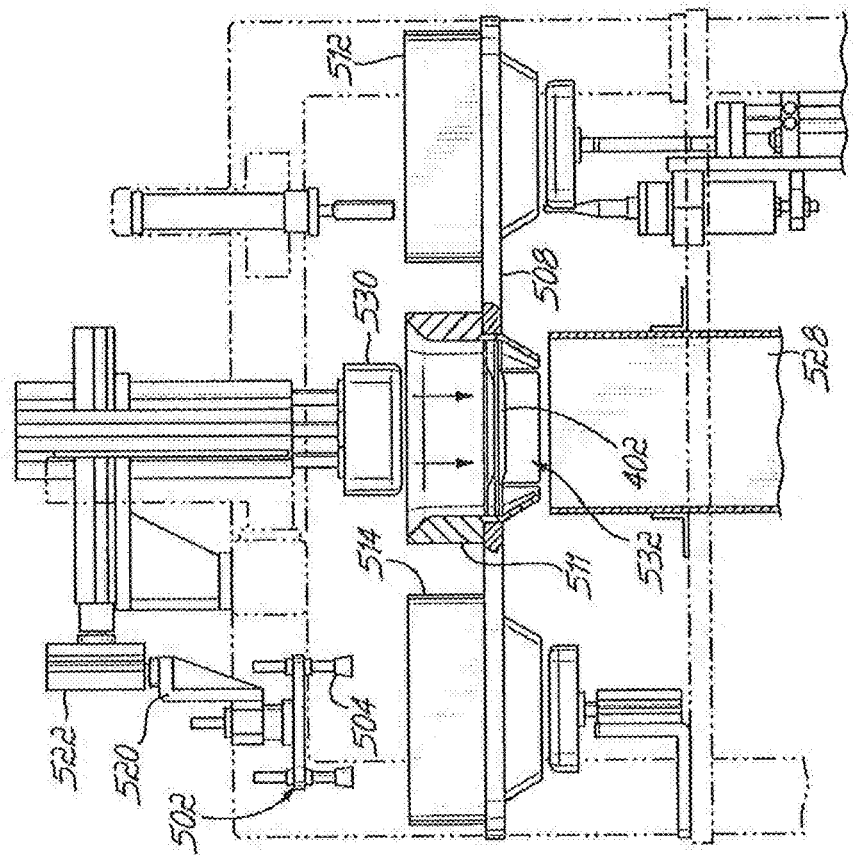

In cross-sectional view, two med pass bags 402 are deposited into the accumulation hopper 511 in FIG. 22 according to the process and sequence of events described previously with respect to FIGS. 18-20. After all the med pass bags 402 are deposited into the accumulation hopper 511, the accumulation dial 508 rotates approximately 90° so that the accumulation hopper 511 is positioned over a discharge chute 528 at the six o'clock position. If the med pass bags 402 in the hopper 511 are for a prescription that has been cancelled, the order is no longer required, the unit dose packages 18 are incorrect in the med pass bags 402 or there is any other problem with the order, a plunger 530 extends downwardly into the hopper 511 to push the med pass bags 402 into the chute 528 which discharges the med pass bags 402 from a reject port 532 in the accumulation dial cabinet 506 as shown in FIG. 17. The indexing of the accumulation dial 508 from the position shown in FIG. 21 to the position of FIG. 24 and the extension of the plunger 530 into the reject chute 528 is shown in FIG. 25.

Figure 27:
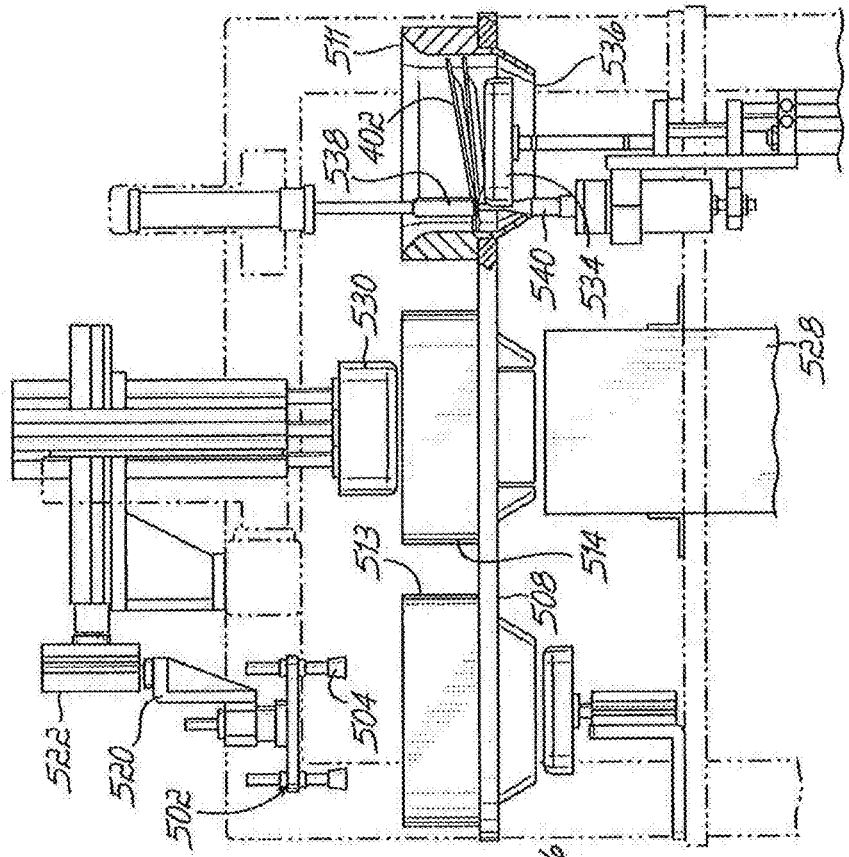
Figure 26:
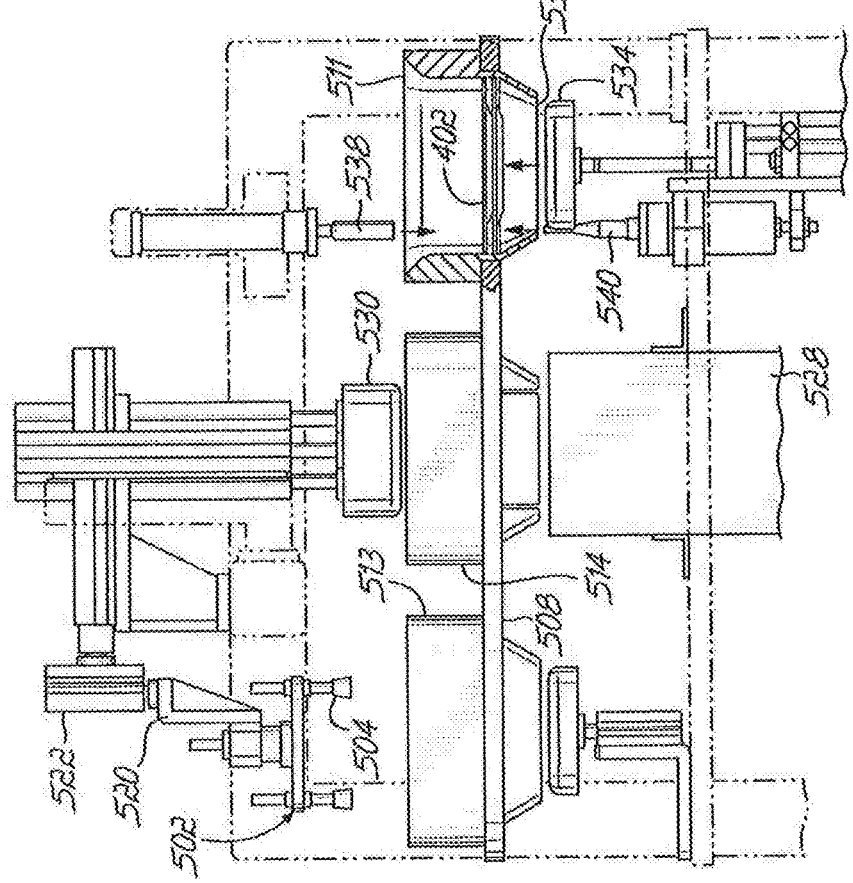

If the med pass bags 402 in the accumulation hopper 511 are correct and accurate, the accumulation dial 508 rotates an additional 90° into the three o'clock position shown in FIG. 26. As such, the med pass bags 402 are positioned approximately 180° and diametrically opposite on the accumulation dial 508 from their original position in the accumulation hopper 511 as shown in FIG. 20. At the position of the med pass bags 402 in the accumulation hopper 511 shown in FIG. 26, the module 500 operates to heat stake together the multiple med pass bags 402 in a given order. In this regard, a stabilizing plunger 534 extends upwardly through the open bottom 536 of the accumulation dial 508 at this position into the hopper 511 to engage the lowermost med pass bag 402. Simultaneously, a heat stake anvil 538 extends downwardly into the hopper 511 to engage the uppermost surface of the top most med pass bag 402 in the hopper 511. A heat stake iron 540 extends upwardly along with the plunger 534 to heat stake the med pass bags 402 together against the anvil 538 as shown in FIG. 27. One advantage of various embodiments of this invention is that the heat stake location is between the first and second top perforated lines 472, 476 on the med pass bags 402 coincident with the double-sided tape 418 as shown in FIG. 16B. After the med pass bags 402 are heat staked together, the anvil 538, plunger 534 and heat stake iron 540 are retracted and the accumulation dial 508 indexes approximately 90° to rotate the hopper 511 into the twelve o'clock position as shown in FIG. 28A.

Figure 28B:
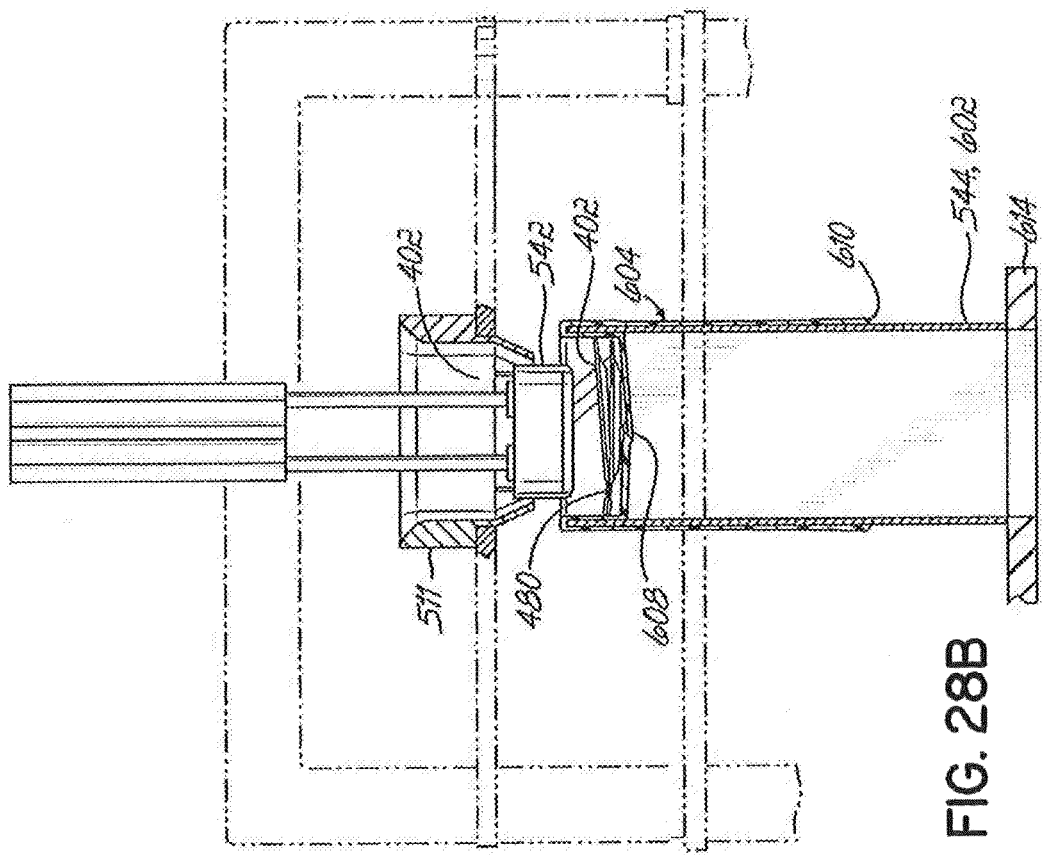
Figure 28A:
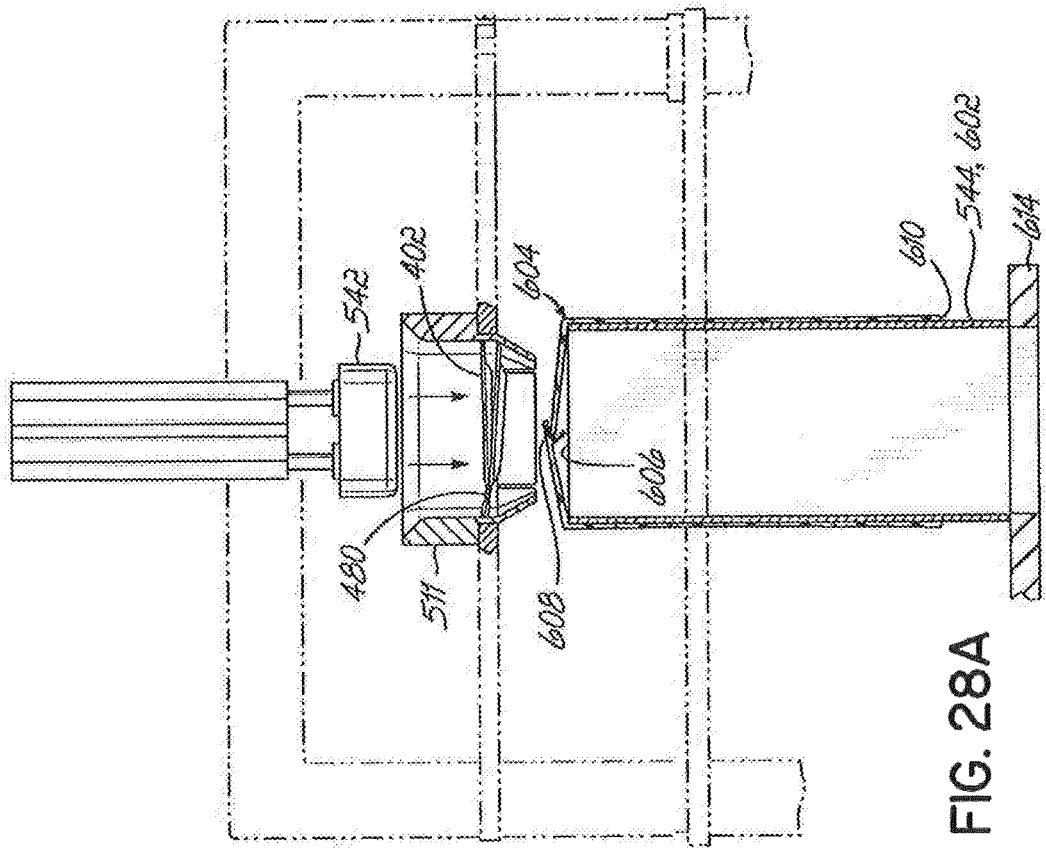

The heat staked med pass bags 402 are then in position in the hopper 511 beneath a plunger 542 at the twelve o'clock position shown in FIG. 28 and above a travel pack shell 602 which has a travel pack 604 fitted over the exterior of the shell 602 as well as the upper open top end 606 of the shell 602. The plunger 542 then extends downwardly as shown in FIG. 28B to force the heat staked med pass bags 402 downwardly through the open bottom of the hopper 511 and onto the travel pack 604 on the shell 602. Continued movement of the plunger 542 downwardly forces the sealed end 608 of the travel pack 604 and the med pass bags 402 downwardly into the interior of the tubular shell 602 thereby pulling the free edge 610 of the travel pack 604 upwardly along the exterior surface of the shell 602 as shown by comparison of the free edges 610 in FIGS. 28A and 28B. After the staked med pass bags 402 are deposited into the travel pack 604 and the tubular shell 602, the plunger 542 retracts upwardly and the accumulation dial 508 rotates 90° to return to the original position shown in FIG. 20 for the processing and packaging of an additional medpass orders and associated bags 402. It will be appreciated by one of ordinary skill in the art that the sequential operations shown in FIGS. 18-28B are happening simultaneously with other such operations which are 90°, 180° or 270° out of phase with the processing sequence for the hopper 511 shown and described with respect to FIGS. 18-288 thereby increasing the efficiency and the decreasing the time required for processing and packaging medpass bag orders according to various embodiments of this invention.

Figure 29:
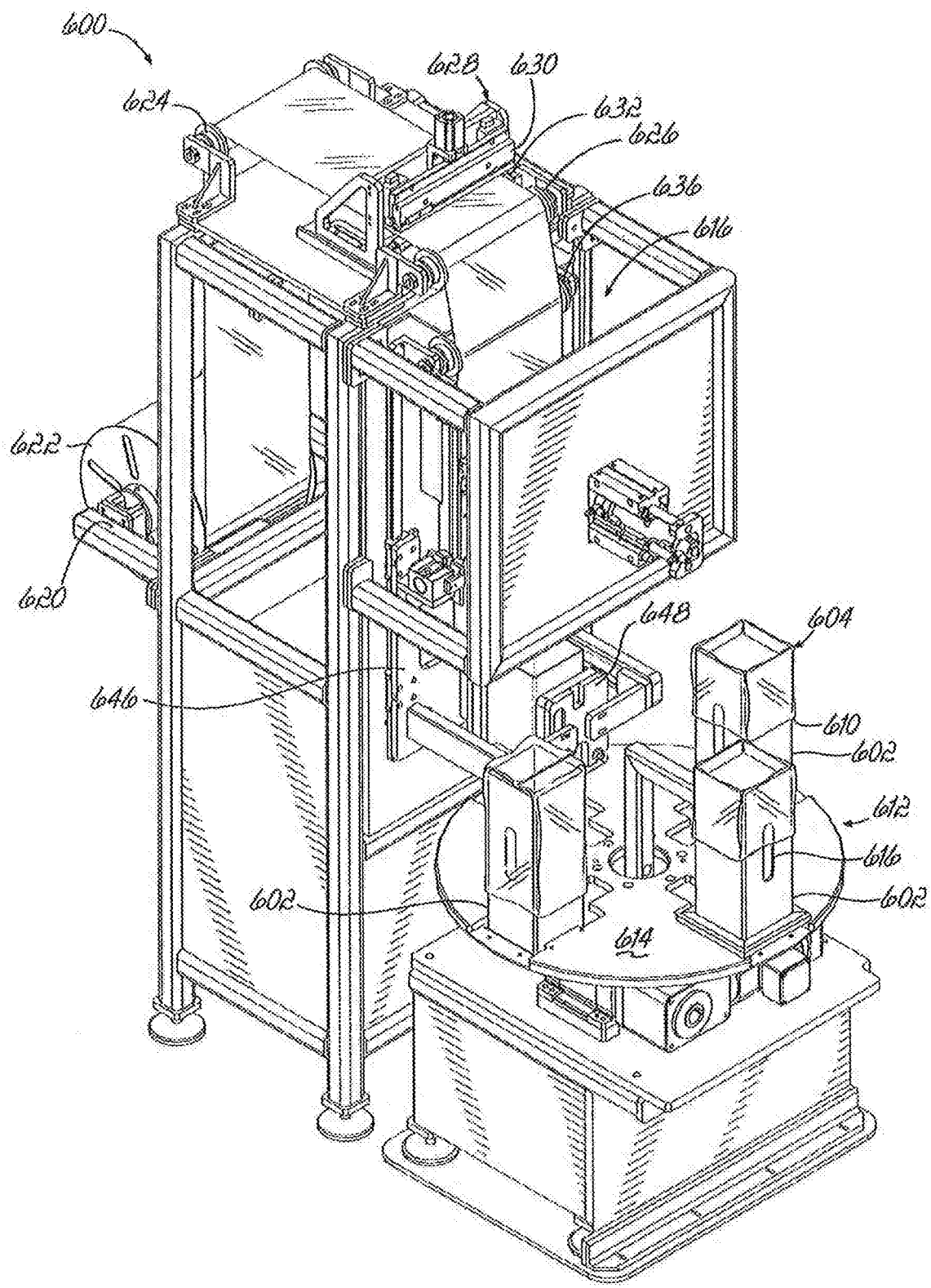
FIG. 29 is a perspective view of a travel pack loader module which forms packs to receive medpass bags therein according to one embodiment of this invention.
Figure 30:
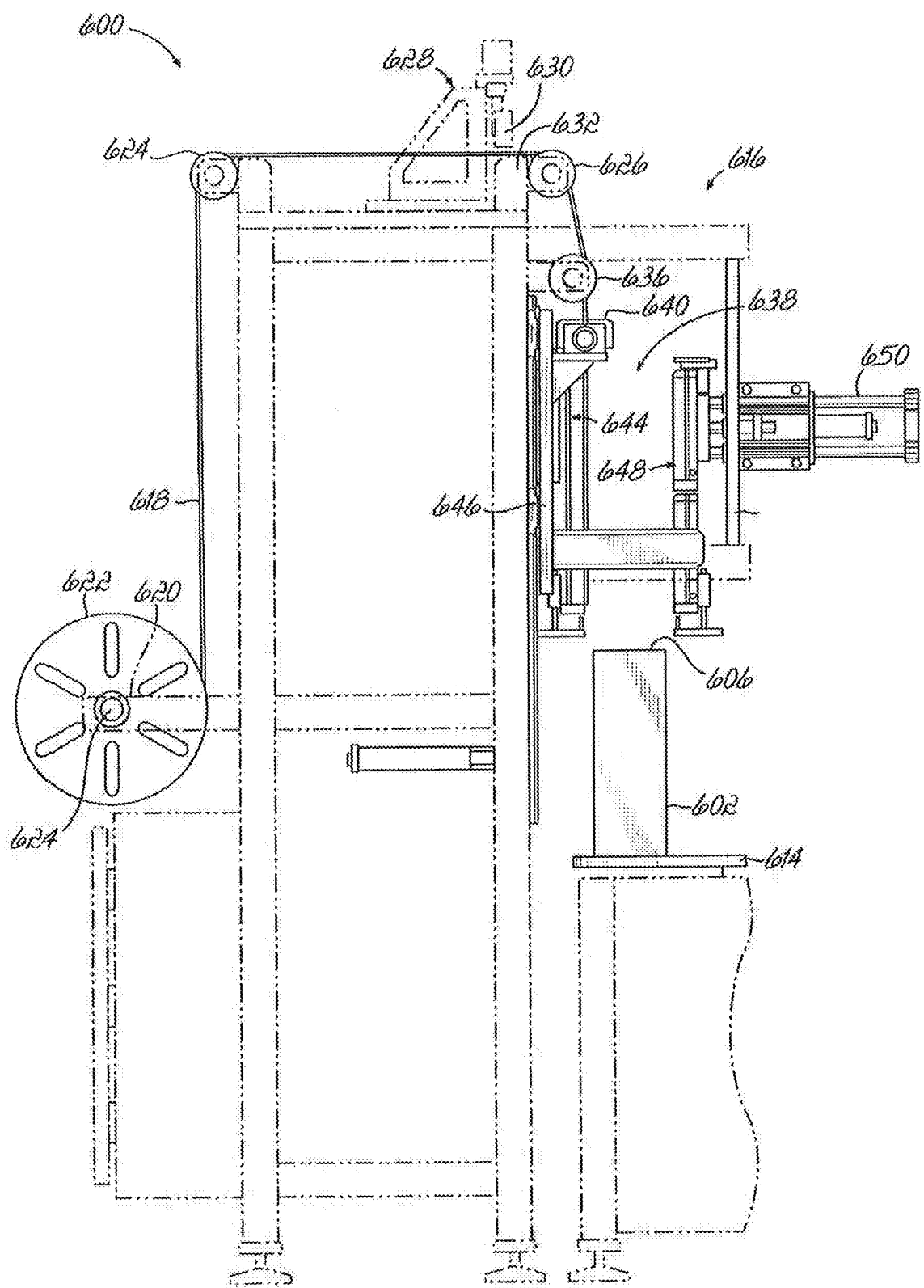
FIGS. 30-32 are cross-sectional side elevational sequential views of the module of FIG. 29 forming a pack according to one embodiment of this invention.

The travel pack module 600 is shown in FIG. 29 and includes a travel pack loader station 612 with a turntable 614 having four tubular shells 602 projecting upwardly and spaced approximately 90° from one another. Each tubular shell 602 has a generally square cross-sectional configuration and may include an oval slot 616 on one or more faces thereof as shown in FIG. 29. The travel pack loader station 612 is located adjacent to a travel pack formation station 616 as shown in FIG. 29. As shown most clearly in FIGS. 29-30, the travel pack formation station 616 includes a spool of travel pack supply material 618 mounted on a bar 620 extending from a back end of the station 616. The pack supply material 618 is a generally flattened elongated tube of thermoplastic material which is generally translucent or transparent LDPE according to various embodiments of this invention. The supply of pack material 618 extends from a supply spool 622 upwardly around a pair of guide rollers 624, 626 mounted atop the station 616. The bag supply material 618 passes through a seam seal assembly 628 mounted atop the station 616 adjacent the downstream roller 626. The seam seal assembly 628 includes a weld head 630 which cooperates with a lower anvil 632 on the assembly 628 to thereby seal the two plies of pack material 618 together and forma seam 634. The weld head and anvil 630, 632 reciprocate relative to one another to weld the plies together and form the lateral seam 634 in the pack material 618.

After the pack supply material 618 passes through the seam seal assembly 628 and over the downstream guide roller 626 and around a positioning roller 636, the pack material 618 is fed into a pack formation assembly 638 on a face of the station 616 adjacent to the turntable 614.

Figure 31:
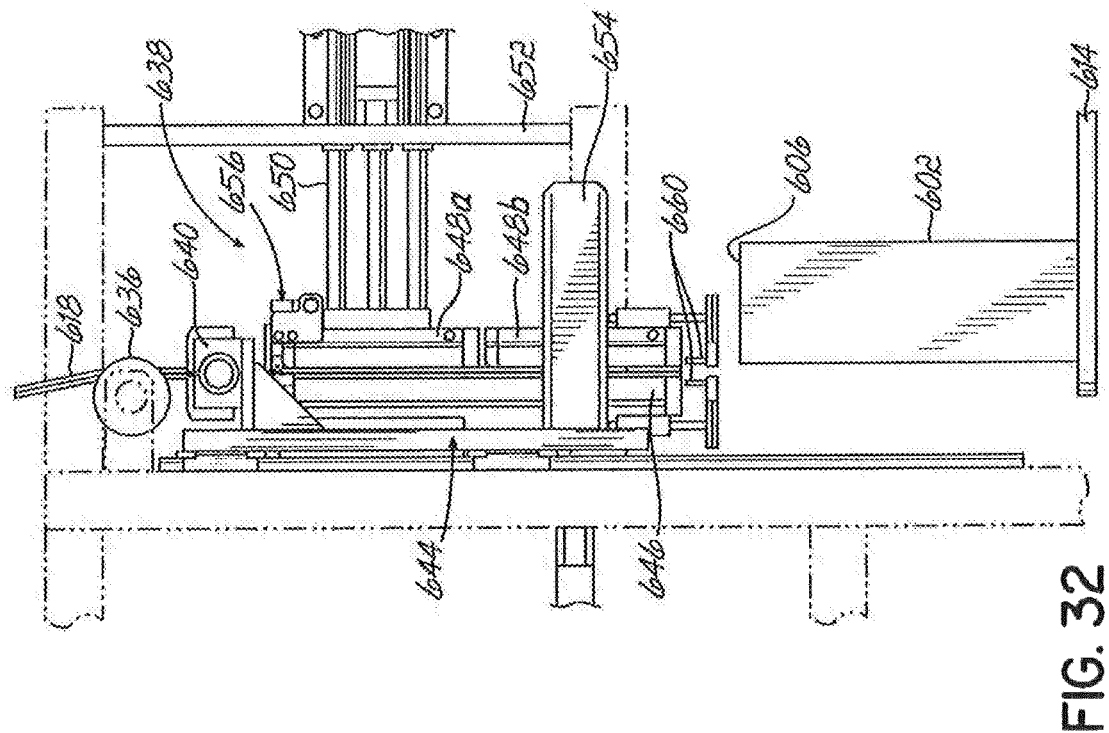
Figure 32:
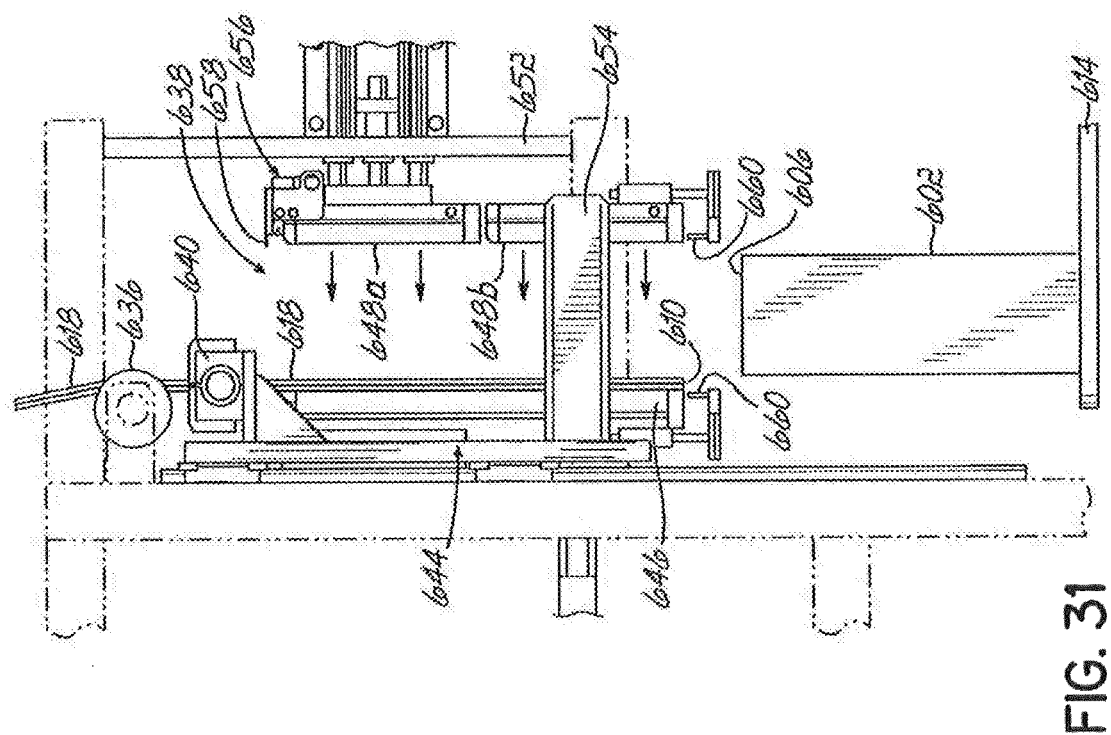

As shown most clearly in FIGS. 31 and 32, the leading free end 610 of the supply of pack material 618 exits the positioning roller 636 and enters the space between a pair of clamp mechanisms 640, each located on a lateral side edge of the pack material 618. The clamp mechanisms 640 each have a pair of opposing clamp members 642 which selectively grip the lateral edge of the pack material 618 therebetween. The clamp mechanisms 640 are mounted on the assembly 638 for reciprocal, vertical movement. When the lateral edges of the pack material 618 are clamped between the clamp members and the clamp mechanisms 640 move downwardly, the pack material 618 is advanced or pulled downstream over the roller 636 and off of the supply spool 622 and in a downward direction as shown FIGS. 37 and 38.

The clamp mechanisms 640 are at the upper end of a carriage assembly 644 which reciprocates vertically to draw the pack material 618 over one of the tubular shells 602 positioned below the carriage assembly 644. The carriage assembly 644 includes opposed and confronting platens 646, 648. One of the platens 646 is located immediately below the clamp mechanisms 640 and the opposing platen 648 is in two sections 648a, 648b and movable toward and away from the first platen 646 on a number of extension rods 650 which extend from a frame 652 of the carriage assembly 644 as shown in FIG. 32. When the extension rods 650 move the two section platen 648 toward the opposing platen 646, it sandwiches there between the pack material 618 in the carriage assembly 644. Each of the platens 646, 648b includes a pneumatic suction face. When the pack material 618 is sandwiched between the platens 646,648 it is folded into a two-ply layer arrangement. The lower platen section 648b is mounted on a carriage arm 654 extending between the opposing platens 646, 648b as shown in FIGS. 31, 32 and 35.

When the pack material 618 is sandwiched between the platens 646, 648 as shown in FIG. 32, a cutter assembly 656 severs the pack material 618 from the supply of pack material downstream from the clamp mechanisms 640. The cutter assembly 656 includes a knife 658 which traverses laterally across the pack material 618 to thereby sever the terminal portion of the pack material 618 as shown in FIG. 35. The pack material 618 is cut by the knife 658 downstream from the clamp mechanisms 640 and upstream from the seam 634 formed in the pack material 618 by the seam seal assembly 628. After the knife 658 severs the pack material 618, the upper platen 648a is retracted on the extension rods 650 as shown in FIG. 35. Likewise, the pneumatic faces of the lower platen 648b and opposing platen 646 are actuated to draw the respective confronting plies of the pack material 618 onto the associated platen 646, 648b as shown in FIG. 35. Once the plies are pneumatically adhered to the respective platens 646, 648b, the lower platen section 648b extends along the carriage arm 654 away from the platen 646 thereby expanding the pack material 618.

Figure 36A:
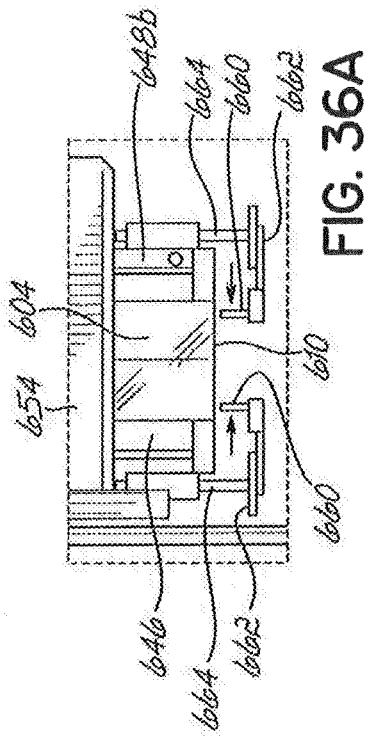
FIGS. 36A-36C are sequential enlarged views of area 36A of FIG. 35 showing a free end of the pack being expanded according to one embodiment of this invention.
Figure 36B:
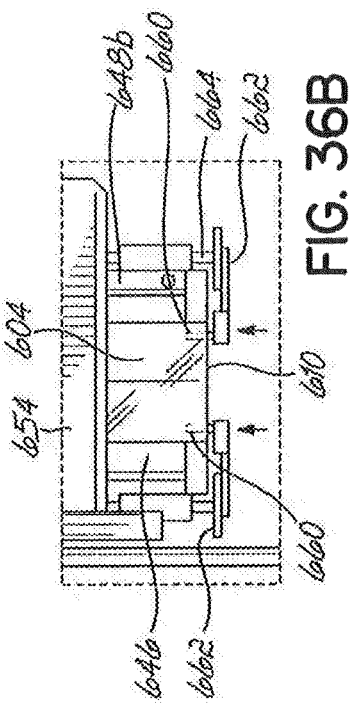
Figure 36C:
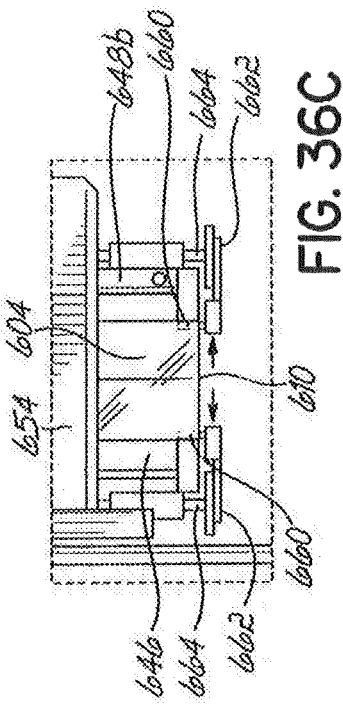
Figure 35:
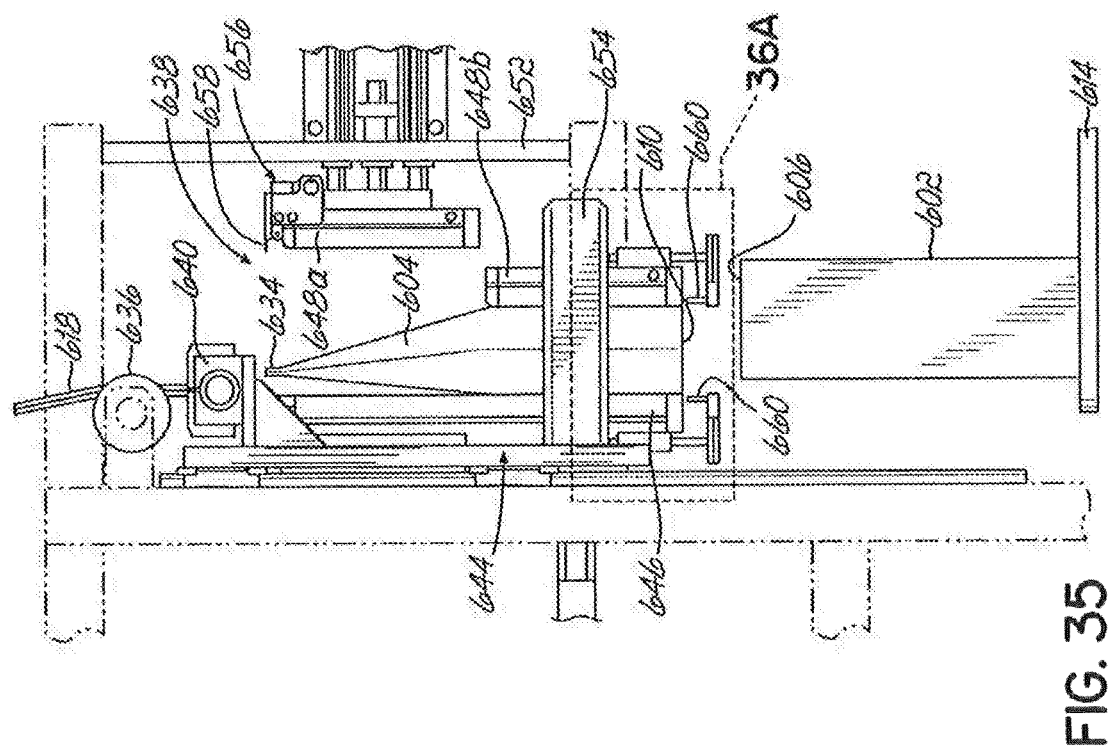
FIG. 35 is a side elevational view showing the severed pack being pulled into an expanded configuration.

As shown in FIGS. 35-36C, as the pack material 618 is expanding between the pneumatic faces of the platens 646, 648b, the lower free edge 610 of the pack material 618 is engaged by two pairs of prongs 660 which extend upwardly. Each pair of prongs 660 is mounted on a mounting bracket 662 which extends generally horizontally and includes an actuation rod 664. As the two plies of pack material 618 are being drawn apart as shown in FIG. 35, the respective prongs 660 are extended toward one another and raised vertically as shown in FIGS. 36A-36B. The prongs 660 are inserted into the open lower end of the pack material 618 as shown in FIG. 36B. Once the prongs 660 are inserted into the open lower end of the pack material, they are retracted outwardly as shown in FIG. 36C to engage and pull the lower open end of a pack material taut around the four spaced prongs 660.

Figure 37:
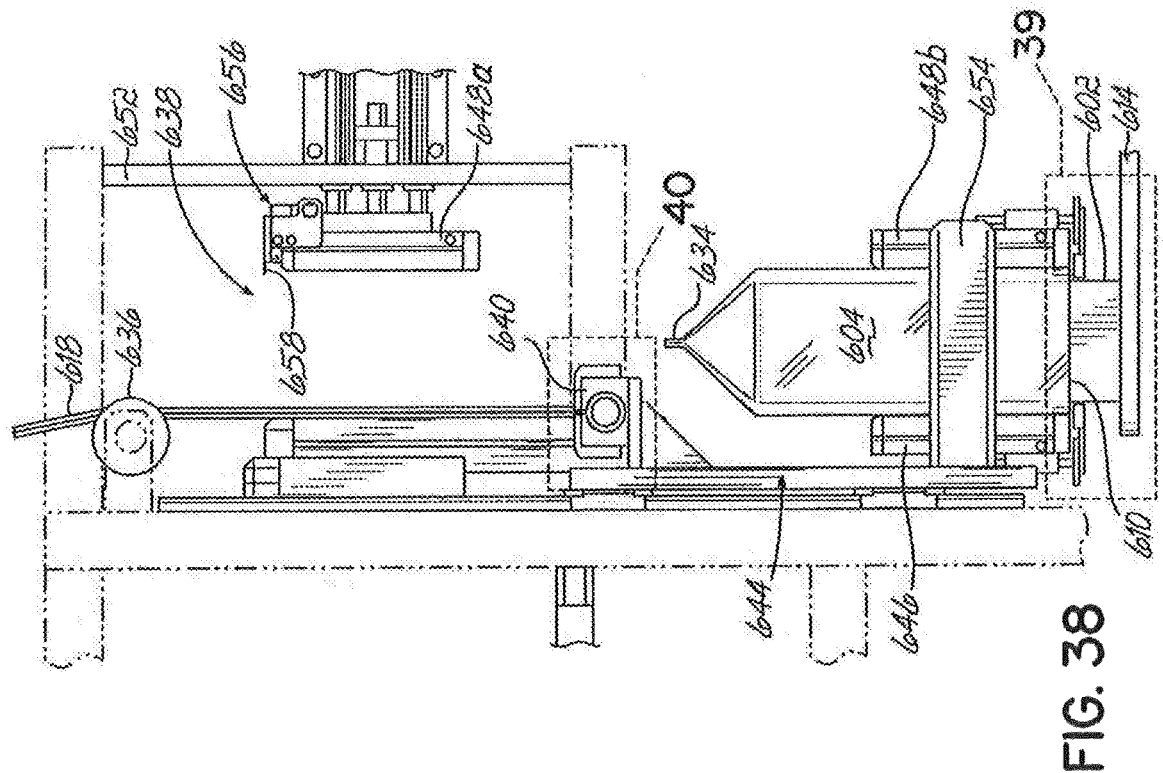
FIGS. 37 and 38 are sequential side elevational views similar to FIG. 35 showing the pack being installed over a tubular shell in preparation for receipt of the medpass bags according to one embodiment of this invention.
Figure 38:
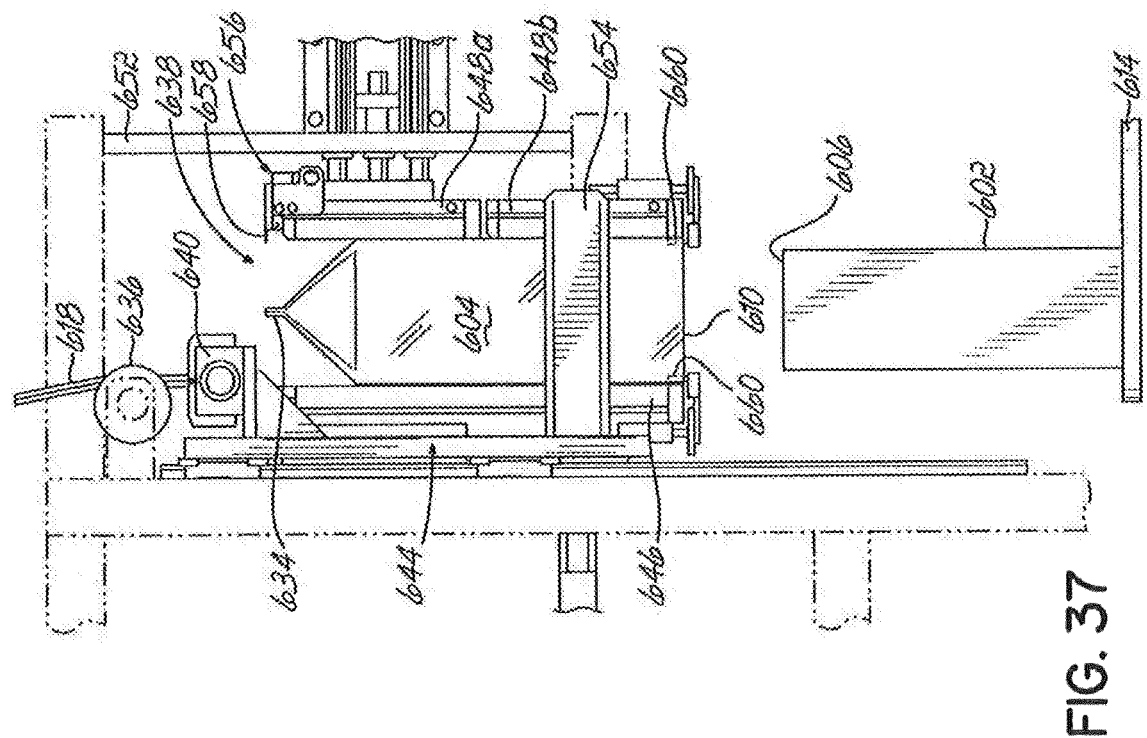

As shown in FIG. 37, the pack material 618 is in an expanded configuration between the opposing platens 646, 648b with the lower free edge 610 is positioned around the prongs 660. At this point, the carriage assembly 644 translates downwardly to pull the pack material over the shell 602 positioned on the turntable 614 beneath the carriage assembly 644 as shown in FIG. 38. As the carriage assembly 644 translates downwardly, the clamp mechanisms 640 have the free edge 610 of the upstream pack material 618 for a subsequent travel pack secured there between and likewise pull the pack material 618 downwardly across the platen 646 for subsequent travel pack formation. The actuation of the clamp mechanisms 640 relative to the pack material 618 is shown sequentially in FIGS. 40A and 40B which are enlarged views of the section 40 shown in FIG. 38.

Once the pack 604 is pulled downwardly and positioned on the shell 602, the prongs 660 retract downwardly and outwardly to disengage the lower free edge 610 of the pack 604 and return to their respective home positions as shown in FIGS. 39A and 39B which are enlarged views of the portion 39 shown in FIG. 38.

Figure 42A:
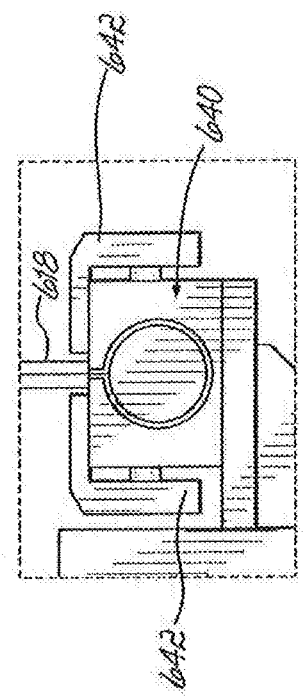
FIGS. 42A and 42B are sequential views of the enlarged section 42 of FIG. 41.
Figure 42B:
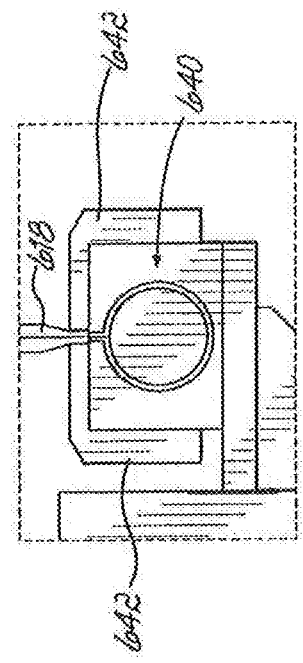
Figure 41:
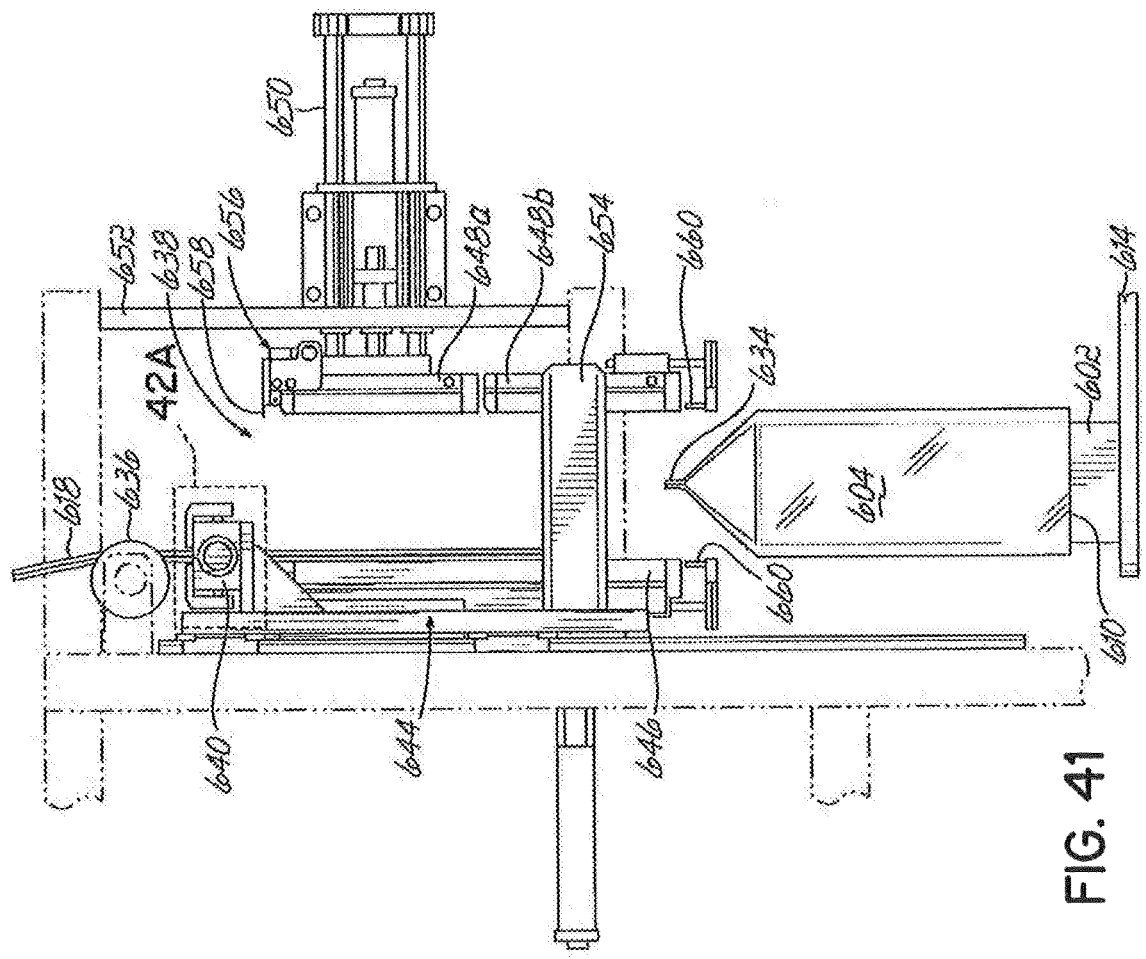
FIG. 41 is a side elevational view similar to FIG. 38 showing a subsequent pack being formed by the module according to one embodiment of this invention.

As shown in FIG. 41, after the pack 604 is installed onto the tubular shell 602, the carriage assembly 644 translates vertically upward with the clamp mechanisms 640 disengaged from the subsequent pack material 618 as shown in FIG. 42A which is an enlarged view of the section 42A shown in FIG. 41. Once the carriage assembly 644 and associated clamp mechanisms 640 return to the upper home position as shown in FIG. 41, the clamps 642 are actuated to reengage the pack material 618 as shown in FIG. 42B and thereby begin the pack formation cycle once again.

Figure 34:
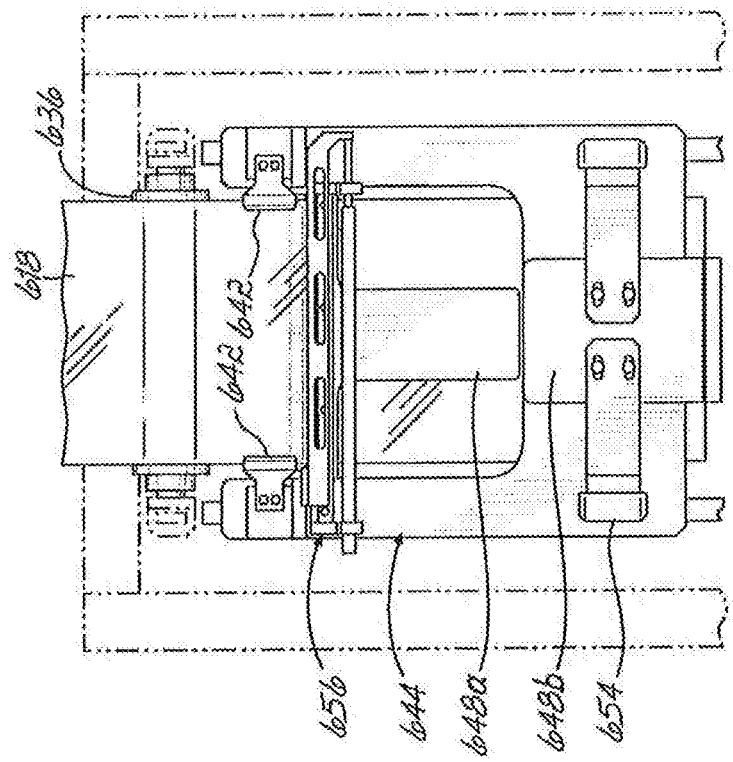
FIGS. 33-34 are sequential top elevational views of the module of FIG. 30 showing a pack being cut from a supply of pack material.
Figure 33:
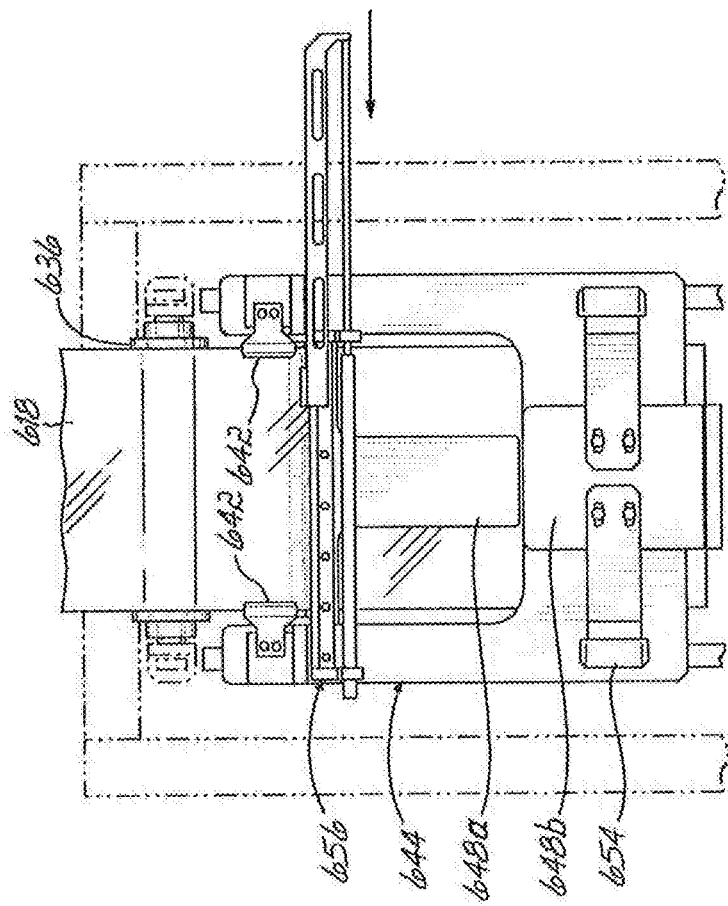

The cutter assembly 656 operation is shown in FIGS. 33 and 34 such that when the platens 646, 648 are pressed together to sandwich the pack material 618 there between as shown in FIG. 32, the cutter assembly 656 translates the knife 658 laterally across the pack material 618 downstream from the clamp mechanisms 640, but upstream from the seam 634 formed in the pack material 618 as shown in FIGS. 33 and 34.

Figure 2A:
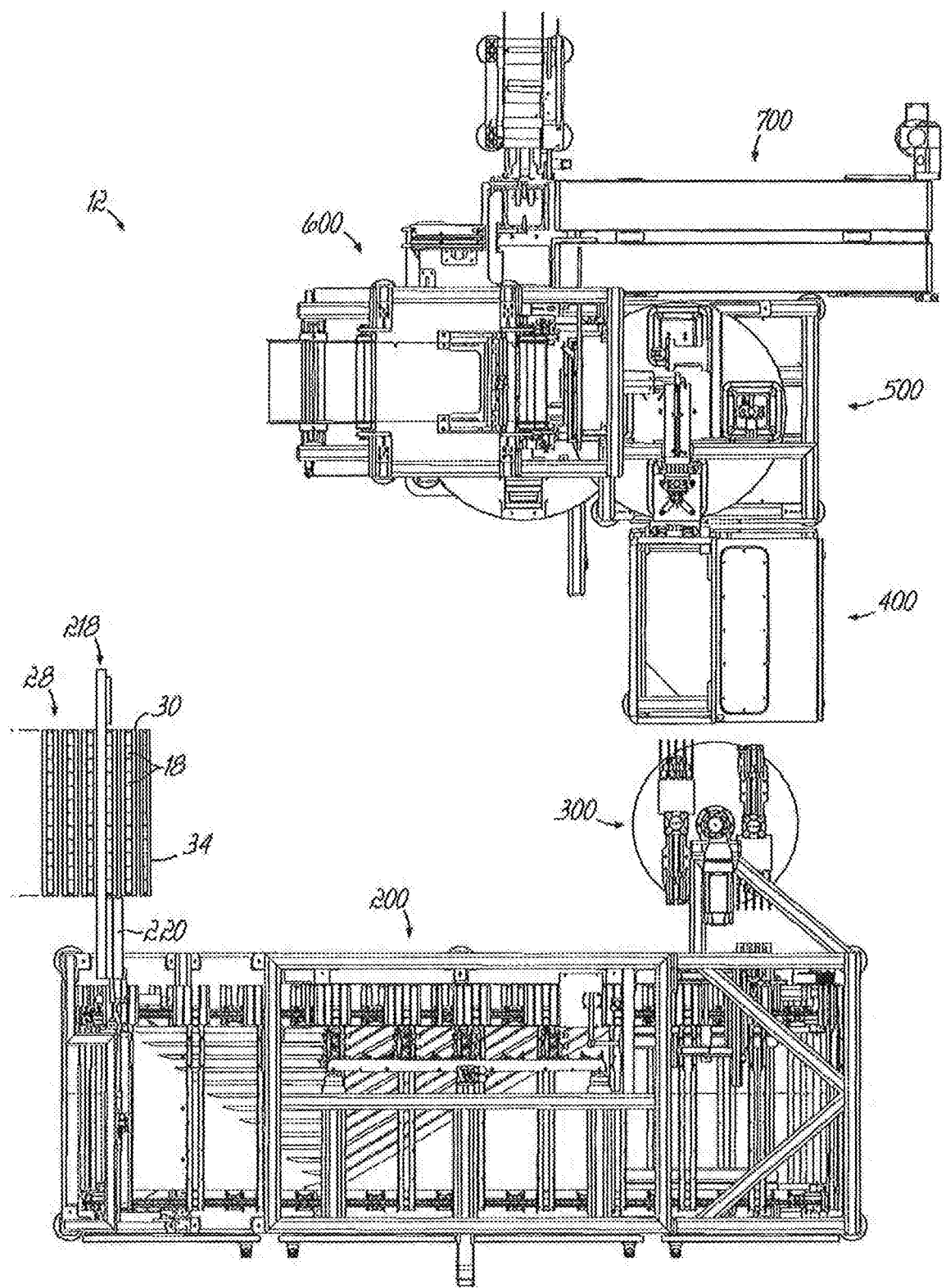
FIG. 2A is a top plan view of the packaging system of FIG. 2.
Figure 43:
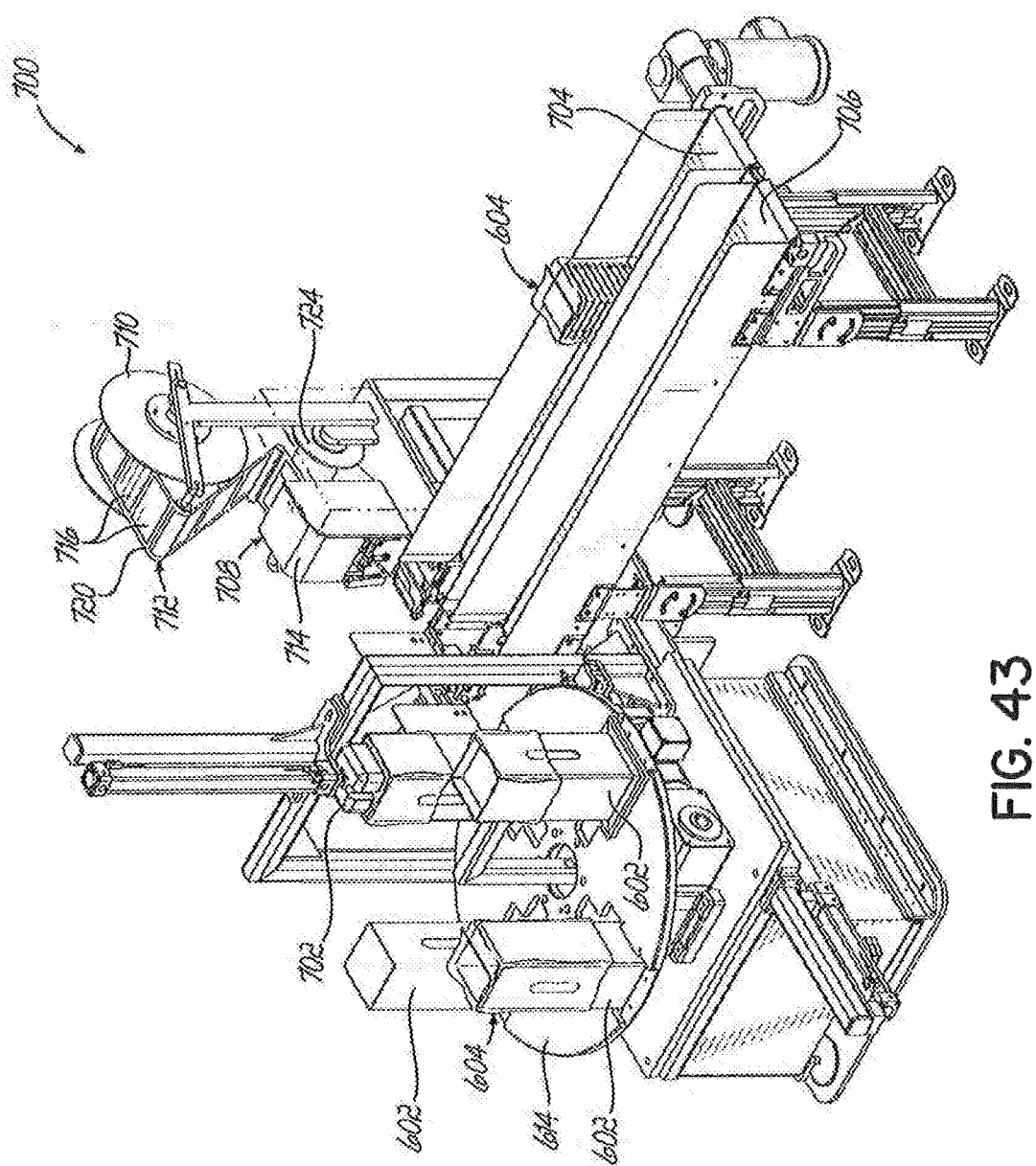
FIG. 43 is a perspective view of a travel pack loader module, label printer assembly and offload conveyors according to one embodiment of this invention.

A label printing and offload module 700 is located adjacent to the travel pack module 600. As is evident from FIG. 2A, the dial 508 on the bag accumulation module 500 overlaps the turntable 614 on the travel pack module such that the tubular shell 602 adjacent to the accumulation dial 508 is positioned beneath the hopper 511 on the accumulation dial 508 so that the plunger 542 extends downwardly to initially seat the heat staked medpass bags 402 into the travel pack 604 and the interior of the tubular shell 602 positioned at the six o'clock position as shown in FIG. 2A. Once the plunger 542 retracts from the shell 602 with the heat staked medpass bags 402 seated in the shell 602, the turntable 614 on the travel pack module 600 rotates approximately 90" until the shell 602 is in the three o'clock position and positioned beneath an offload plunger 702 on the printing and offload module 700 as shown in FIG. 43.

A pair offload conveyors 704, 706, one of which is for processing and offloading travel packs 604 with regularly scheduled medpass bag orders and the other offload conveyor 704 is for processing and offloading stat or special orders of medpass bags 402. A label printing station 708 is located adjacent to the offload conveyors 704, 706 and includes a spool 710 of label material 712 mounted for rotation above a printer 714. The spool 710 of label material 712 has a supply of labels 716 each of which has an adhesive-coated face 718 initially secured to a substrate 720 of the label material 712 and an opposite front face 722 of the label 716.

Figure 44:
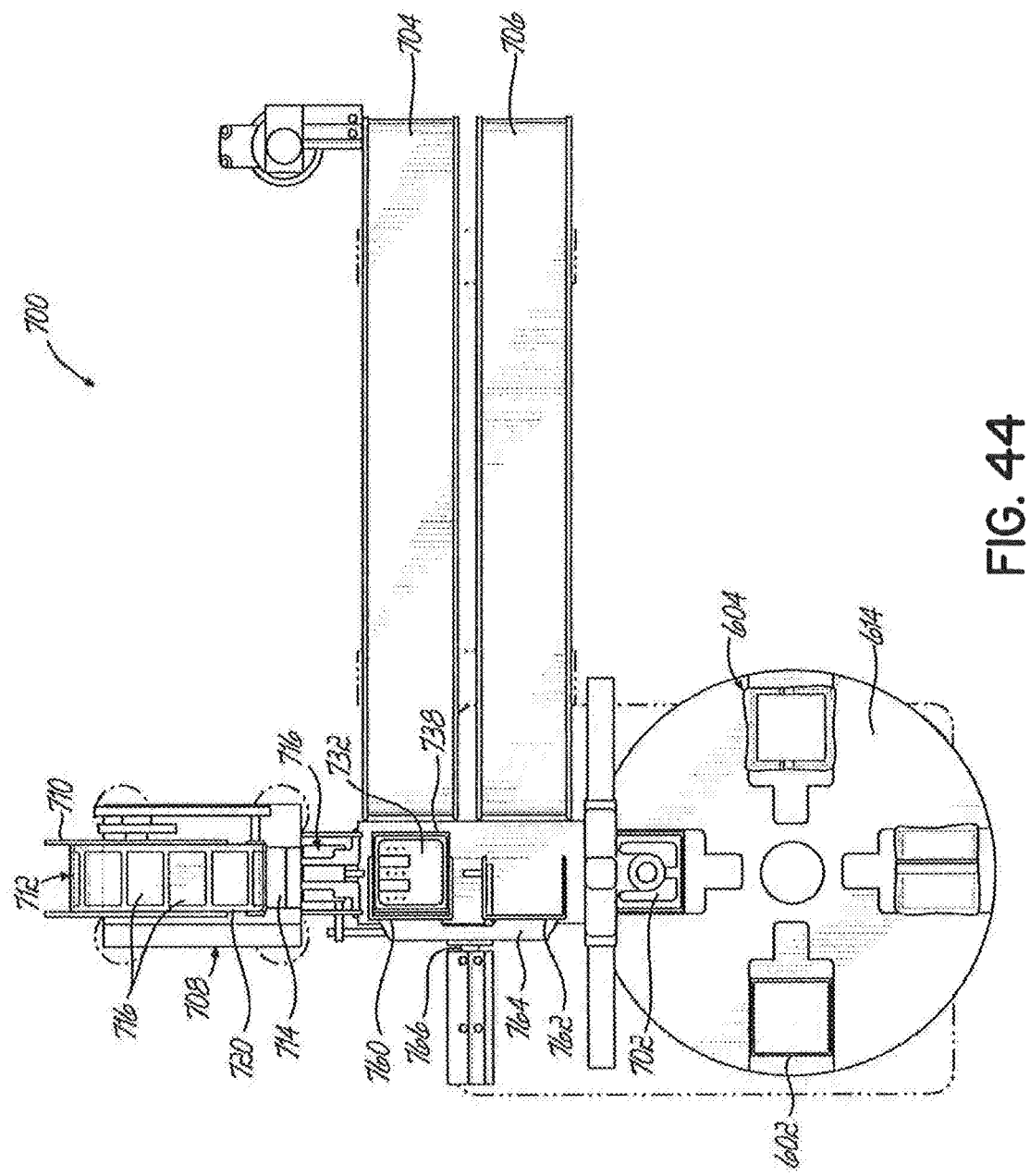
FIG. 44 is a top plan view of the components shown in FIG. 43.
Figure 46:
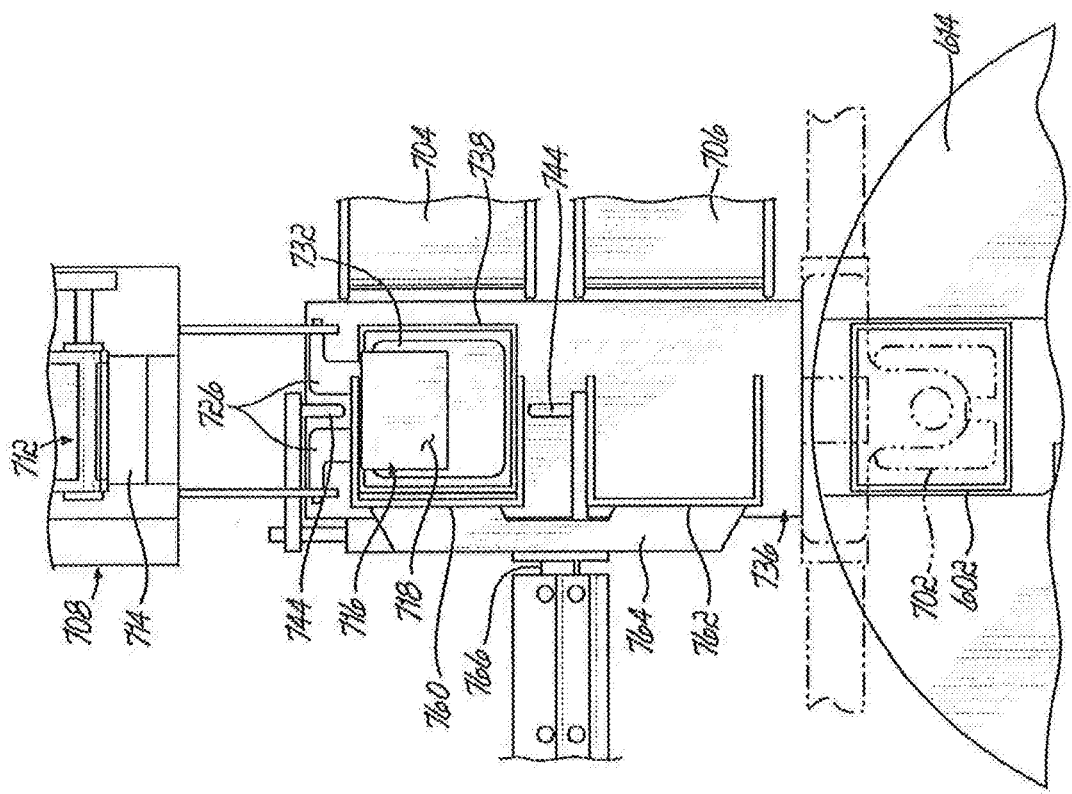
FIGS. 45-47 are sequential views similar to FIG. 44 showing a label being installed on a travel pack.
Figure 45:
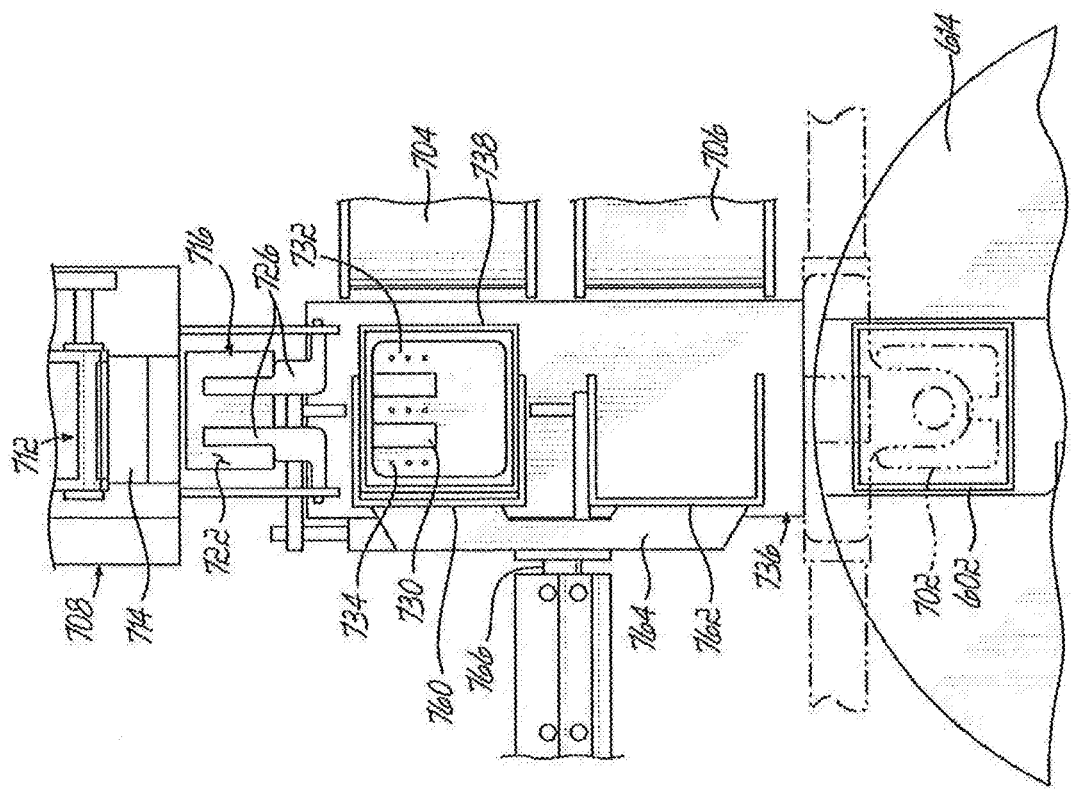

FIG. 44 is a top plan view of the label printing and offload module 700 and the adjacent turntable 614 on the travel pack module 600. The printer 714 prints patient information, medication information, bar codes, QR codes and/or other relevant information on each label 716 for the assigned travel pack 604 containing the appropriate medpass bags 402 and unit dose packages 18. The label 716 is peeled from the substrate 720 and the substrate 720 is accumulated on a substrate accumulation roller 724 contained within the printer station 708. The label 716 is deposited onto a pair of flipper arms 726 in an upward orientation with the print face 722 facing upwardly juxtaposed against the flipper arms 726 as shown in FIG. 45. Each of the flipper arms 726 includes suction ports 728 which is coupled to a pneumatic assembly such that upon actuation of the assembly, the label 716 is temporarily held by the suction force delivered through the ports 728 against the flipper arms 726 which pivot approximately 180° into a position as shown in FIG. 46 while still pneumatically securing the label 716 thereto. The front face 722 of the label 716 as shown in FIG. 46 is facing downwardly with the adhesive surface 718 of the label 716 facing upwardly and which will subsequently be applied to a bottom end of the travel pack 604. When the flipper arms 726 rotate 180° from the orientation shown in FIG. 45 to that shown in FIG. 46, the flipper arms 726 are seated within a pair of correspondingly sized and shaped notches 730 on a label transfer plate 732. The label transfer plate 732 likewise has a number of suction ports 734 to pneumatically retain the label 716 onto the label transfer plate 732.

Figure 47:
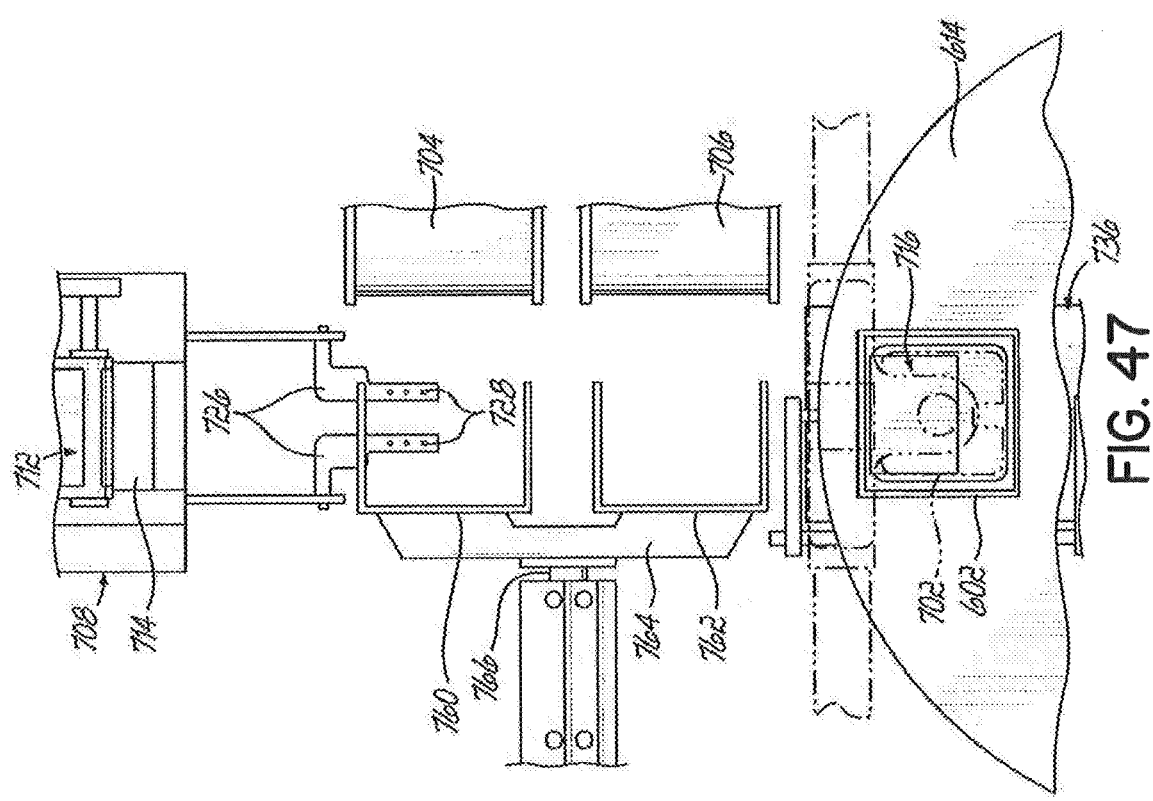
Figure 49:
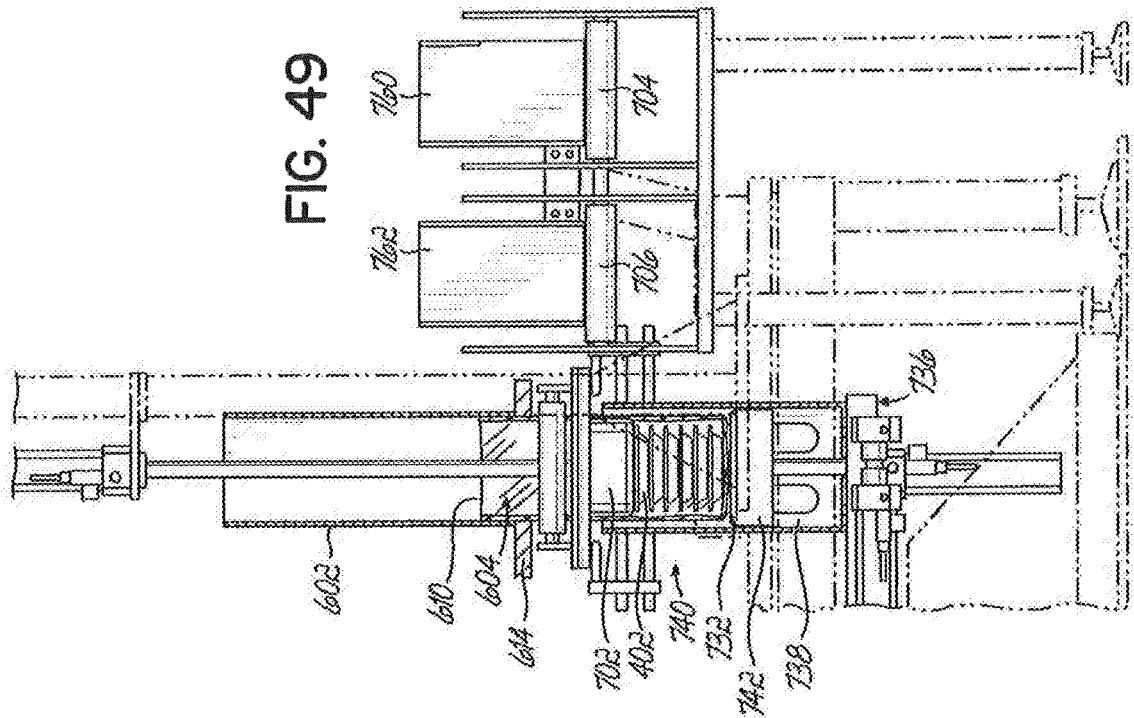
FIGS. 48-49 are side elevational sequential views of medpass bags being inserted into a pack in the shell in preparation for sealing and label application.
Figure 48:
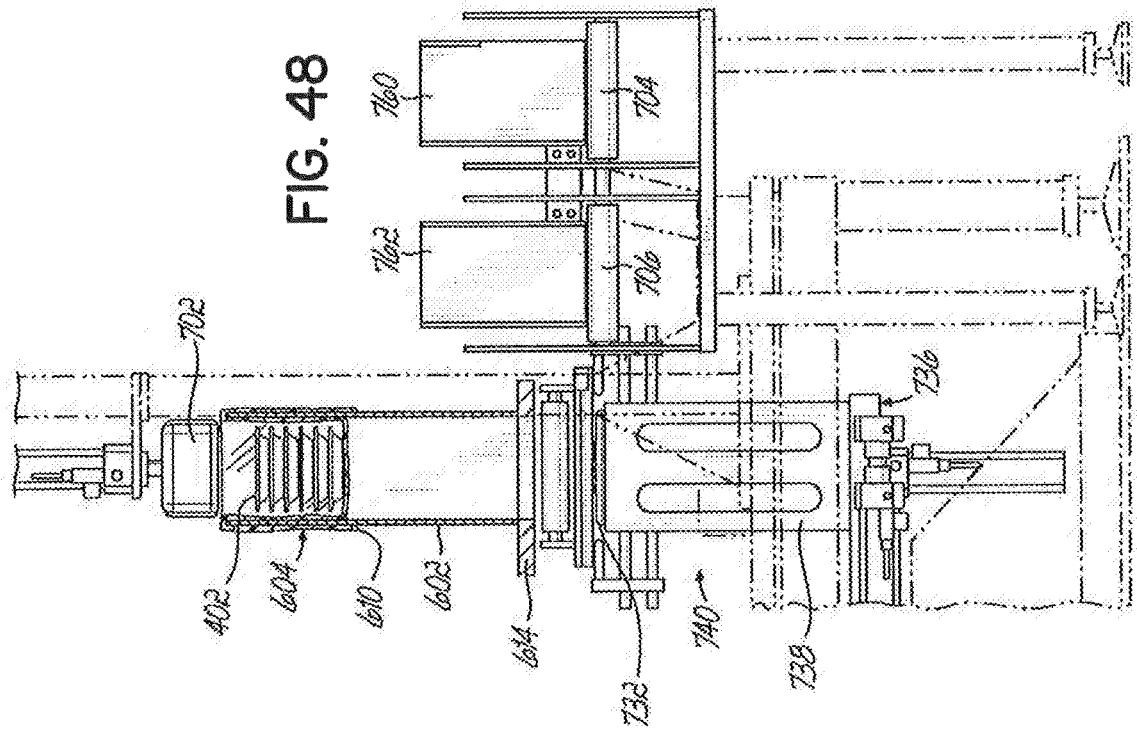

The label transfer plate 732 as shown in FIG. 44 is mounted atop a shuttle assembly 736 which shuttles the label transfer plate 732 from the position shown in FIG. 44 in which it is adapted to receive the flipper arms 726 and label 716 from the printing station 708 to a location in which the label transfer plate 732 is positioned beneath the three o'clock position on the travel pack formation turntable 614 as shown in FIG. 47. As is seen in FIG. 48, the label 716 is transferred to a position beneath the three o'clock position on the travel pack module turntable 614 and above a tubular sleeve 738 beneath the turntable 614. The tubular sleeve 738 beneath the turntable 614 is vertically aligned with the shell 602 at the three o'clock position on the travel pack formation turntable 614. The plunger 702 positioned above the shell 602 on the turntable 614 extends downwardly to push the medpass bags 402 and travel pack 604 toward the bottom of the shell 602 and thereby pulling the free edge 610 of the travel pack 604 upwardly, around the upper edge of the shell 602 and then downwardly into the interior of the shell 602 along with the medpass bags 402 as shown in FIG. 49. As the plunger 702 pushes the medpass bags 402 and travel pack 604 downwardly through the open bottom of the shell 602 on the turntable 614 and into contact with the label 716 on the label transfer plate 732, the label 716 is adhered to the travel pack 604 and the suction via the ports 734 and 728 ceases and the transfer plate 732 retracts back toward the printer 714 via the shuttle assembly 736. Continued downward movement of the plunger 702 seats the medpass bags 402 in the travel pack 604 beneath a pack sealing assembly 740 and within the sleeve 738.

Figure 50:
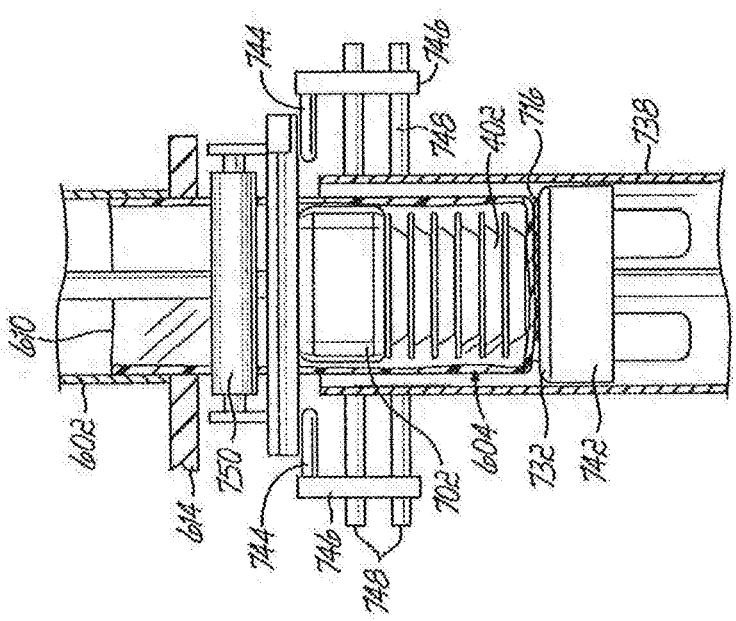
FIGS. 50-52 are side elevational partial cross-sectional views of the pack being sealed around the medpass bags according to one embodiment of this invention.
Figure 51:
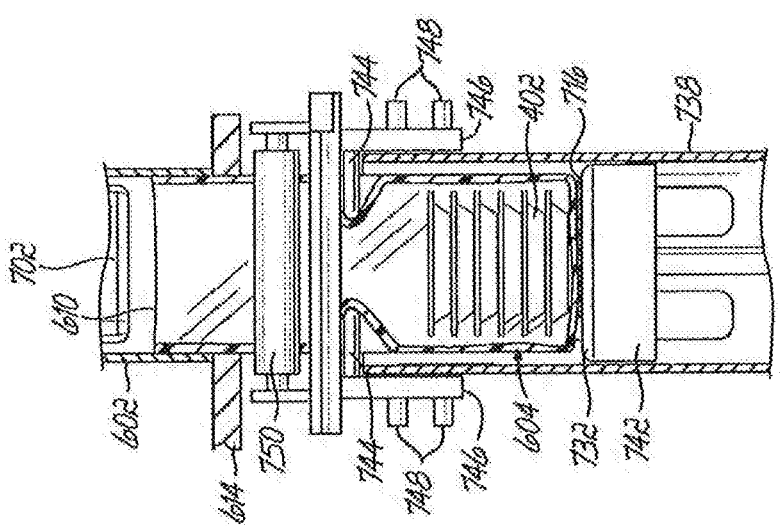
Figure 52:
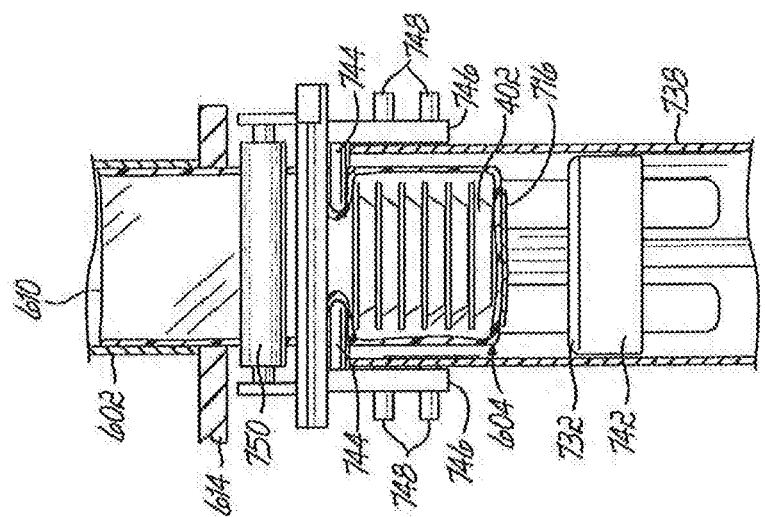

Referring to FIGS. 51-55, the downwardly acting plunger 702 extends into the sleeve 738 and seats the travel pack 604 with medpass bags 402 therein on an upwardly acting plunger 742 seated within the lower sleeve 738 as shown in FIG. 50. At this point, the downwardly acting plunger 702 retracts upwardly and exits from the sleeve 738. The pack sealing assembly 736 includes a pair of opposing lugs 744, each mounted on a mounting bracket 746 on a pair of extension rods 748 as shown in FIG. 50. After the downwardly acting plunger 542 retracts, the lugs 744 are extended inwardly and into contact with the pack 604 and above the upper edge of the sleeve 738 as shown in FIG. 51. As the lugs 744 advance inwardly toward one another, they gather the travel pack material above the medpass bags 402 together thereby drawing up any slack between the lugs 744 and the medpass bags 402 as shown in FIG. 52. As such, the travel pack 604 is uniquely conformed to the volume occupied by and around the medpass bags 402 thereby minimizing any excess pack material 618 around the medpass bags 402.

Figure 53:
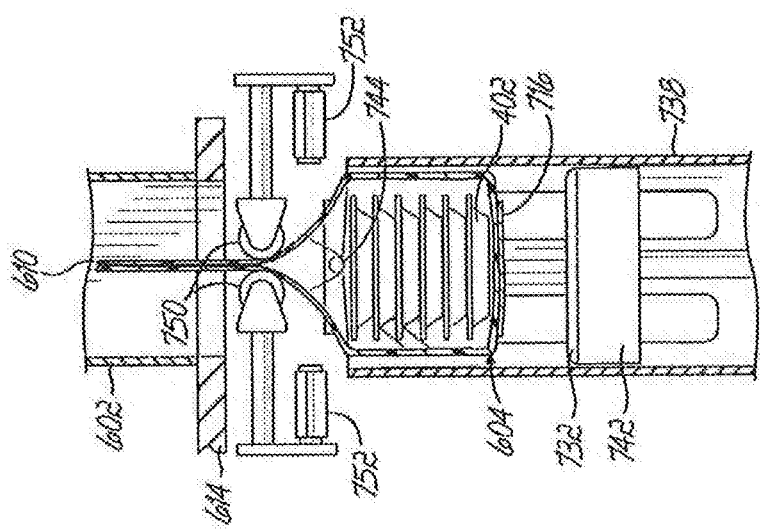
FIGS. 53-55 show an orthogonal cross-sectional view of the arrangement and sequential pack-sealing operation shown in FIGS. 50-52.
Figure 54:
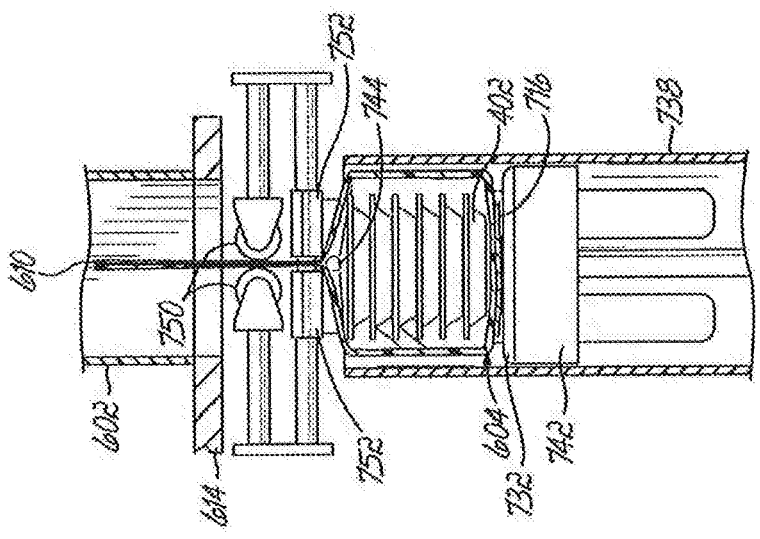
Figure 55:
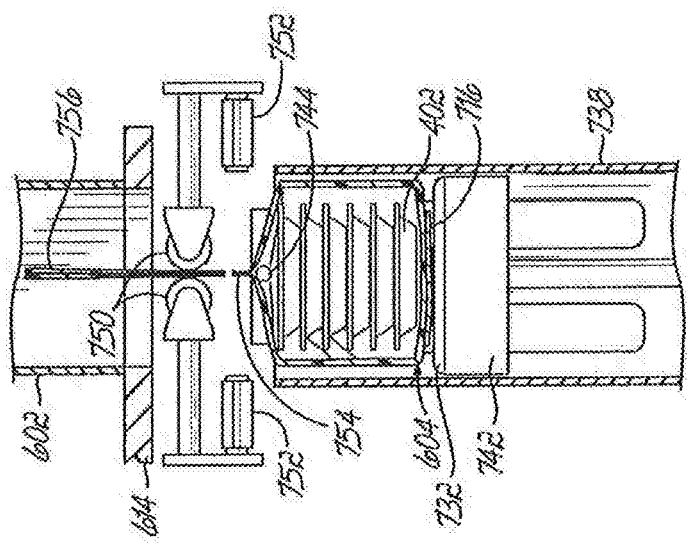

FIGS. 53-55 show an orthogonal cross-sectional view of the arrangement and sequential pack-sealing operation shown in FIGS. 50-52. A pair of oppositely directed pinch rollers 750 extend toward one another thereby pinching the pack material 618 between the rollers 750 and above the lugs 744 after the downwardly acting plunger 702 has retracted. The lugs 744 provide a gusset or fold in each side of the pack material 618 and the folds are completed by the pinch rollers 750 which hold the two plies of the pack material together as shown in FIG. 53. Opposing weld members 752 are positioned beneath the pinch rollers 750 and extend toward one another as shown in FIG. 54 thereby simultaneously forming a seam or weld 754 in the pack 604 and severing excess selvage 756 of the pack material 618 upstream from the weld 754 as shown in FIG. 55. After the weld 754 is formed to close the top end of the travel pack 604, the weld members 752 and lugs 744 retract. After the travel pack 604 is transferred to the offload conveyors 704 or 706, the selvage material 756 is discharged from between the rollers 750 and collected as scrap.

Figure 57:
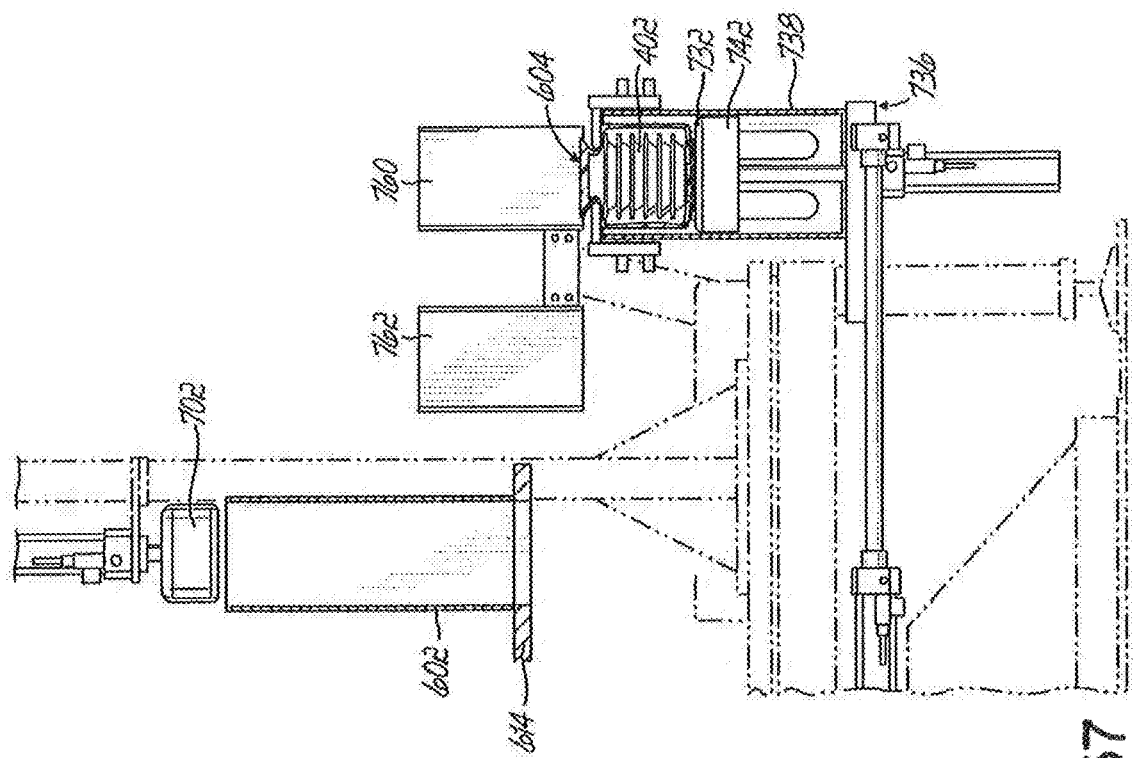
FIGS. 56-58 are side elevational partial cross-sectional sequential views of the sealed and labeled travel pack being transferred to one of two offload conveyors according to one embodiment of this invention.
Figure 56:
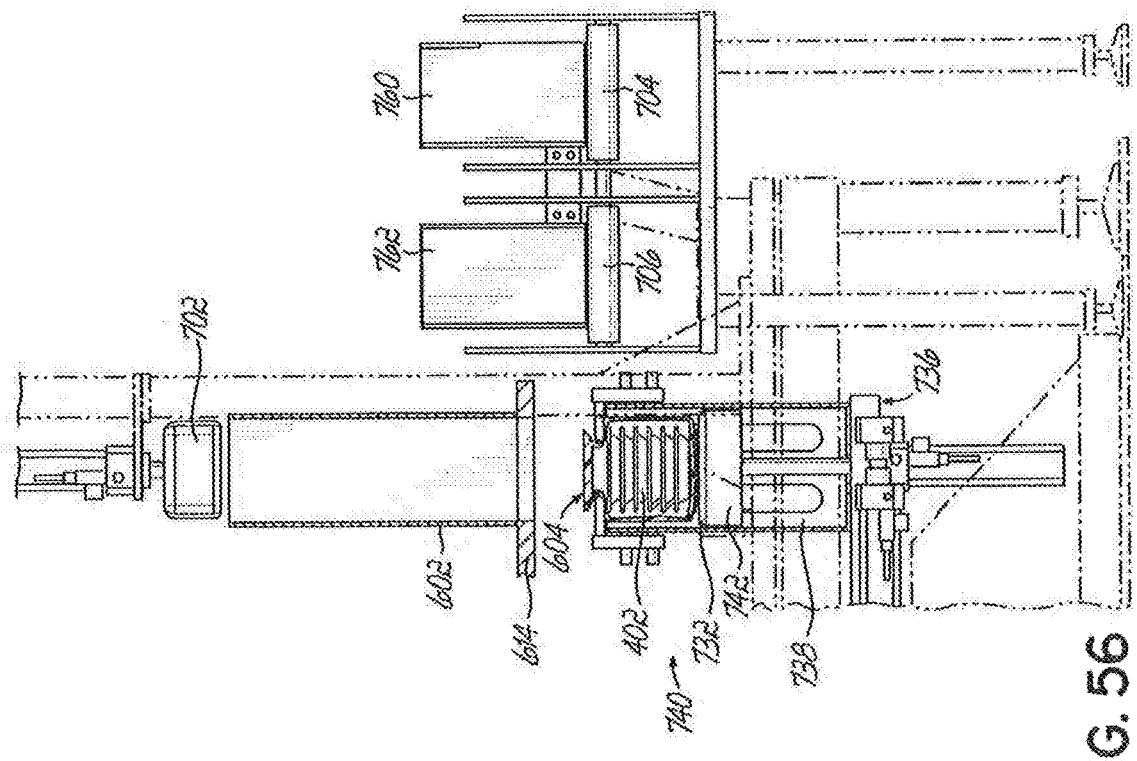
Figure 58:
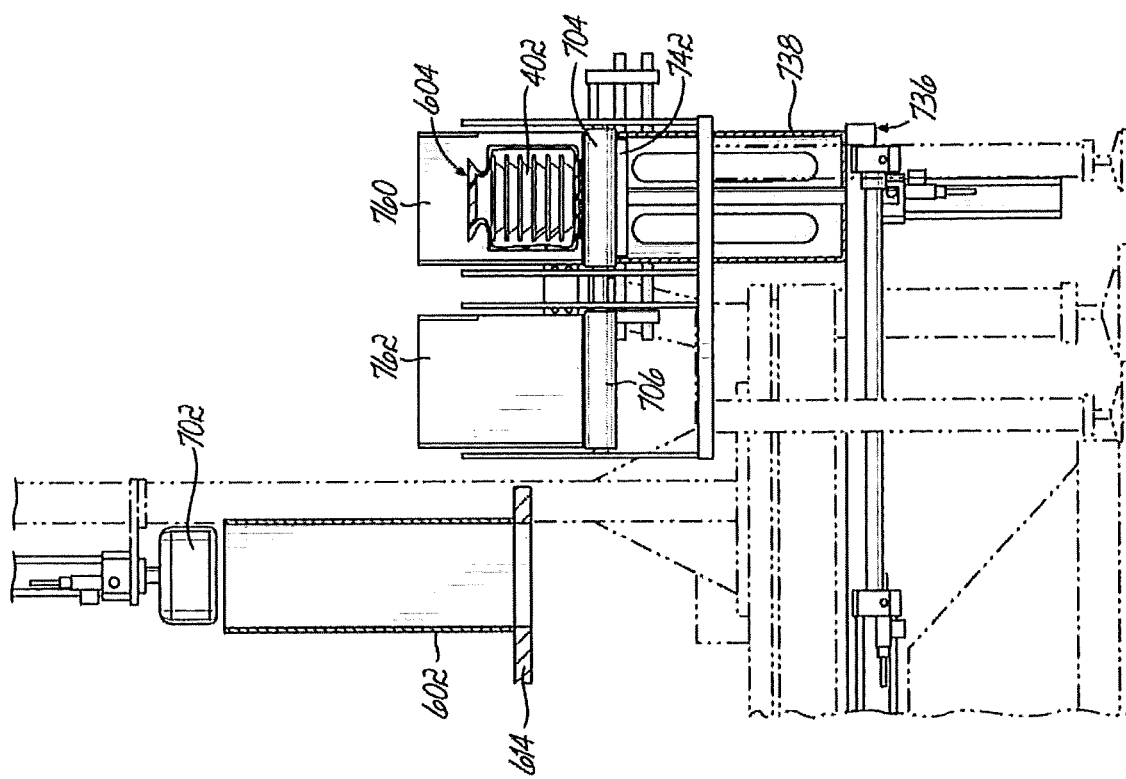
Figure 60:
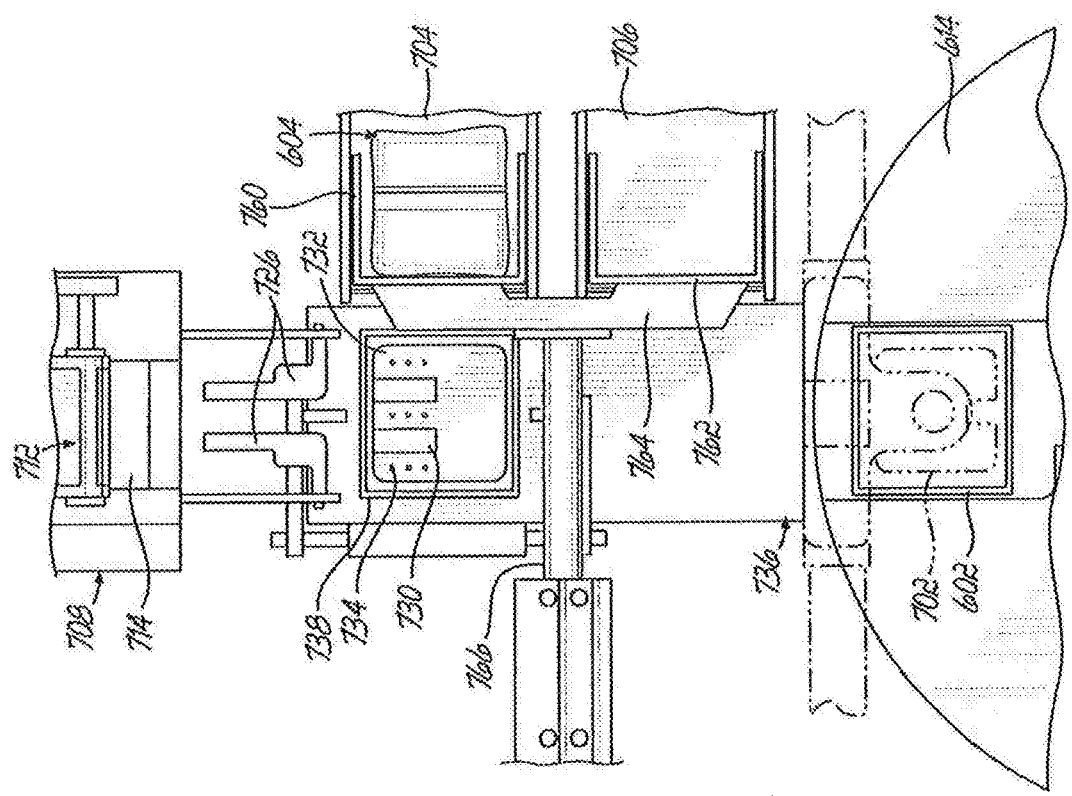
FIGS. 59 and 60 are top partial cross-sectional and sequential views of the travel pack being positioned on one of the offload conveyors.
Figure 59:
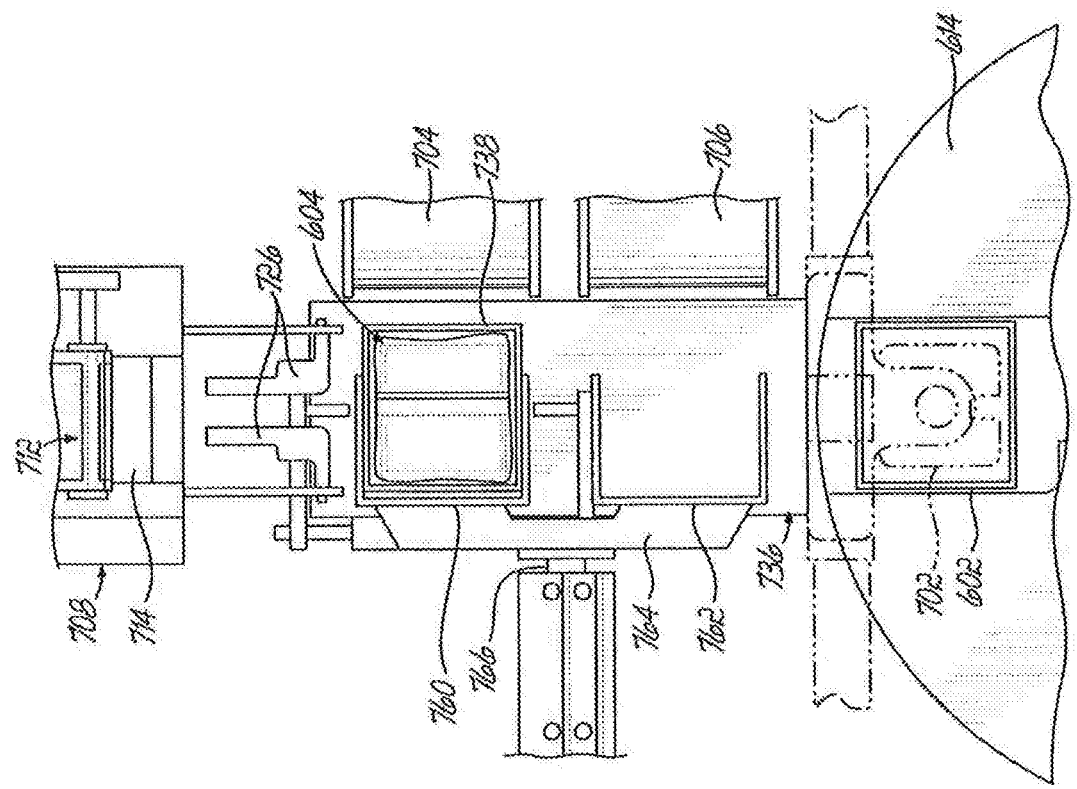

Depending upon whether the travel pack 604 contains standard or stat medpass order medications and supplements, the shuttle assembly 736 aligns the travel pack 604 with the appropriate offload conveyor 704 or 706 as shown in FIG. 57. Once positioned relative to the appropriate offload conveyor, the plunger 742 in the lower sleeve 738 extends upwardly thereby pushing the travel pack 604 into one of two U-shaped members 760,762 as shown in FIG. 58. The two U-shaped members 760, 762 as shown in top plan view of FIGS. 59 and 60 are joined to the opposite ends of a yoke member 764 which is at the end of a pusher bar 766. The pusher bar 766 extends thereby advancing the U-shaped members 760, 762 toward the offload conveyors 704, 706 and likewise the travel pack 604 seated within either of the U-shaped members. Continued extension of the pusher bar 766 into the orientation of FIG. 60 deposits the travel pack 604 onto the upstream end of the appropriate offload conveyor 704 or 706 which then conveys the travel pack 604 to an offload position and deposits it into an appropriate tote, box or other accumulation receptacle (not shown) at the downstream end of the offload conveyor 704 or 706.

Figure 61:
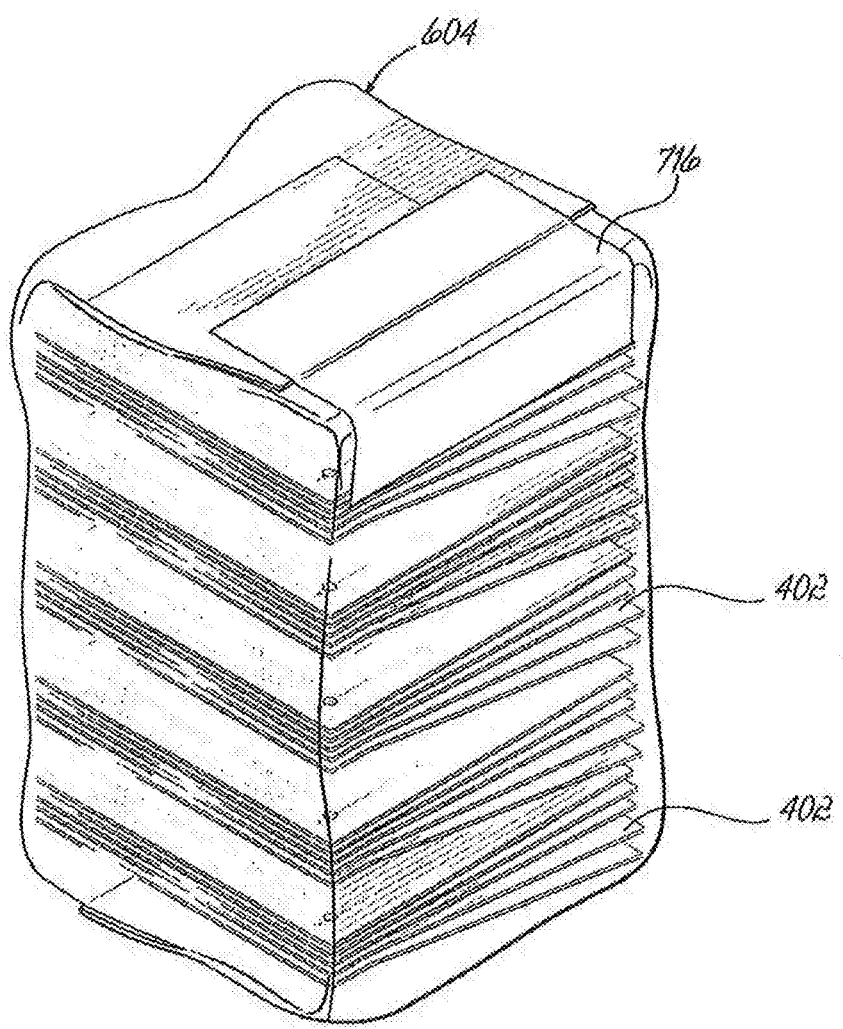
FIG. 61 is a perspective view of the travel pack with attached label containing a number of staked medpass bags with unit dose packages of medications and supplements ready for delivery to the LTC or other healthcare institution according to one embodiment of this invention.

The resulting travel pack 604 and label 716 with the heat staked medpass bags 402 contained therein is shown in FIG. 61. After the appropriate travel packs 604 are deposited into the tote or other receptacle, they can then be shipped or otherwise transported to the LTC or other facility for appropriate administration to the prescribed patients.

The design of the overall system 12 and its individual components according to this invention allows for physical control of each unit dose package 18 from start to finish without any unit dose package "free fall" in the system. This process is automated via appropriate computer operations and does not rely upon manual sorting or handling. The medpass bags 402 are consolidated into the travel packs 604 and a final shipping tote and do not require manual sorting and packing. The fill event server or control 36 interfaces with the system 12 and provides appropriate packing commands according to the orders. It will be appreciated that although it is preferable to separately retain each of the unit doses within individual packages 18 which are assembled with one another in a given medpass bag 402 such as date sequential for a single patient, medpass or by patient number (for multiple patients within an institutional setting); the medications and supplements may be alternatively packaged in any convenient form which allows a set of medications or supplements which was selected via the order to be taken at a given time or medpass to be easily retrieved for use without departing from the invention.

Each individual medpass bag 402 may be configured with an indicia containing information about whom the individualized prescription has been created for, and the time that the dose is to be taken. For example each bag 402 may contain the name of who is to take the order, for example "Jane Doe" and their address, should the packet get misplaced, "1990 Paxit Drive, Columbus, Ohio 43230". Each medpass bag 402 preferably contains the date and time the dose is to be taken, for example a series may appear as: "8:00 AM on Tuesday, Jun. 1, 2009", "2:00 PM on Tuesday, Jun. 1, 2009", "8:00 PM on Tuesday, Jun. 1, 2009", "8:00 AM on Wednesday, Jun. 2, 2009", . . . "8:00 PM on Tuesday, Jun. 29, 2009". The bag 402 may include additional information such as "Take with food" and any other precautions. Inserted instructions or content list may also be included within each bag 402. In addition, the bag 402 may contain information listing information about the medications or supplements contained therein. The heat staked bags are placed in the travel pack 604 and the tote with any other portions of the order, and shipped to the LTC.

Various aspects of this invention include the following which may or may not have been addressed herein above. Each medpass bag 402 may be resident or patient specific. However, the invention offers at least three options of how the medications are included in the medpass bag 402, including:
 a) All meds for the entire day, such that the medpass bag 402 would be resident and administration day specific only.
 b) Meds for a given time grouping. Example: medpass bags 402 would be specific to the resident/admin day/morning, afternoon or evening. All medications to be administered for that time description would be collected for inclusion in the bag 402.
 c) Only medications for one administration time such that the medpass bags 402 are resident/admin day/admin time specific resulting in bags for each resident/admin day/8 AM vs. 9 AM, etc.
 d) The above three options are advantageous in that typical dispensing modes use method c). However, the system may be programmed for disaster planning purposes to immediately switch over to Option a). Option b) may be used for more independent living where residents self medicate. As the system may be used for in-home care, if an adult is truly independent, they start them off receiving bags 402 sorted by Option a). As they need more 'guidance', they could advance to Option b) and ultimately Option c).

Medpass bags 402 are heat staked together at a particular location on the bag 402. One option is to heat stake the medpass bags 402 in the middle of the bags (right on top of the name and room location) which may make it very hard to see such information. Another option is to move the heat stake location to the corner which may make flipping through the stack of staked medpass bags 402 much easier.

Medpass bags 402 may include a message banner. A location is reserved on the medpass bags 402 to communicate to the administration nurses. Typical messages are NEW, STAT, PRN, XD (extra dose), OWE (for a medication that was previously short filled), STAT/NEW, etc. This feature assists the nurses when looking for the medication with that message banner.

The variable print (all resident, admin day/time, medications, location, etc.) is accomplished by thermal transfer printing on the medpass bag 402. This allows one common packaging material to be customized per facility, resident and time, while maintaining the cost leverage of a common packaging material.

From the above disclosure of the general principles of this invention and the preceding detailed description of at least one embodiment, those skilled in the art will readily comprehend the various modifications to which this invention is susceptible. Therefore, we desire to be limited only by the scope of the following claims and equivalents thereof.

We claim:
1. A package insert module, comprising:
 a turntable having a circular surface and rotatable about a turntable axis; and
 an insert assembly mounted on the circular surface of the turntable and off-set from an axis bisecting the circular surface, the insert assembly including a finger arrangement for offloading a plurality of packages, the finger arrangement including a lower finger assembly and an upper finger assembly, wherein
 the upper finger assembly is moveable relative to the lower finger assembly in a direction parallel to the turntable axis to clamp and release the packages between the upper finger assembly and the lower finger assembly, the upper finger assembly and the lower finger assembly is moveable in a direction orthogonal to the turntable axis, and every finger of the upper finger assembly is aligned directly above an inner finger of the lower finger assembly.

2. The package insert module according to claim 1, wherein an array of the plurality of the packages includes at least four parallel rows, and wherein the lower finger assembly includes five spaced and generally parallel fingers such that an outer two of the fingers are positioned on an outside of a first row and a fourth row of the four parallel rows and an inner three of the fingers are positioned between adjacent packages in the array.

3. The package insert module according to claim 2, wherein the upper finger assembly includes three spaced and generally parallel fingers aligned with the inner three of the fingers of the lower finger assembly such that, when the fingers of the upper finger assembly are positioned over the array of the plurality of the packages, the fingers of the upper finger assembly are superimposed onto overlapping edges of the packages.

4. The package insert module according to claim 1, wherein the upper finger assembly is initially spaced from the lower finger assembly to insert the array of the plurality of the packages between the upper finger assembly and lower finger assembly.

5. The package insert module according to claim 1, wherein the insert assembly includes a lower mounting block mounted atop the turntable and an upper mounting block mounted on the lower mounting block, and wherein the finger arrangement is mounted to the upper mounting block.

6. The package insert module according to claim 1, wherein the turntable is configured to rotate the finger arrangement between a first position to offload the plurality of the packages from the nest and a second position to offload the plurality of the packages to a bag formation module.

7. The package insert module according to claim 1, wherein each package of the plurality of the packages includes a unit dose of medicine.

* * * * *